United States Patent
Chen et al.

(10) Patent No.: US 12,043,653 B2
(45) Date of Patent: Jul. 23, 2024

(54) EFFICIENT DELIVERY OF THERAPEUTIC MOLECULES TO CELLS OF THE INNER EAR

(71) Applicants: Massachusetts Eye and Ear Infirmary, Boston, MA (US); President and Fellows of Harvard College, Cambridge, MA (US)

(72) Inventors: Zheng-Yi Chen, Chestnut Hill, MA (US); David R. Liu, Lexington, MA (US); Margie Li, Cambridge, MA (US); David B. Thompson, Cambridge, MA (US); John Zuris, Cambridge, MA (US)

(73) Assignees: Massachusetts Eye and Ear Infirmary, Boston, MA (US); President and Fellows of Harvard College, Cambridge, MA (US)

( * ) Notice: Subject to any disclaimer, the term of this patent is extended or adjusted under 35 U.S.C. 154(b) by 107 days.

(21) Appl. No.: 17/750,530

(22) Filed: May 23, 2022

(65) Prior Publication Data
US 2022/0281941 A1    Sep. 8, 2022

Related U.S. Application Data

(62) Division of application No. 15/523,317, filed as application No. PCT/US2015/058081 on Oct. 29, 2015, now Pat. No. 11,370,823.

(60) Provisional application No. 62/072,220, filed on Oct. 29, 2014.

(51) Int. Cl.
| | |
|---|---|
| *C07K 14/705* | (2006.01) |
| *A61K 9/00* | (2006.01) |
| *A61K 9/50* | (2006.01) |
| *A61K 38/00* | (2006.01) |
| *A61P 27/16* | (2006.01) |
| *C07K 14/435* | (2006.01) |
| *C07K 14/46* | (2006.01) |
| *C07K 14/47* | (2006.01) |
| *C12N 5/071* | (2010.01) |
| *C12N 5/0793* | (2010.01) |

(52) U.S. Cl.
CPC .......... *C07K 14/705* (2013.01); *A61K 9/0046* (2013.01); *A61K 9/5068* (2013.01); *A61P 27/16* (2018.01); *C07K 14/43595* (2013.01); *C07K 14/463* (2013.01); *C07K 14/47* (2013.01); *C12N 5/062* (2013.01); *C12N 5/0627* (2013.01); *A61K 38/00* (2013.01); *C07K 2319/00* (2013.01); *C12N 2501/42* (2013.01); *C12N 2501/60* (2013.01); *C12N 2501/606* (2013.01); *C12N 2501/998* (2013.01); *C12N 2506/00* (2013.01)

(58) Field of Classification Search
None
See application file for complete search history.

(56) References Cited

U.S. PATENT DOCUMENTS

| | | | |
|---|---|---|---|
| 3,645,090 | A | 2/1972 | Mochizuki et al. |
| 3,940,475 | A | 2/1976 | Gross |
| 4,302,204 | A | 11/1981 | Wahl et al. |
| 4,358,535 | A | 11/1982 | Falkow et al. |
| 5,034,506 | A | 7/1991 | Summerton et al. |
| 5,138,045 | A | 8/1992 | Cook et al. |
| 5,218,105 | A | 6/1993 | Cook et al. |
| 5,258,498 | A | 11/1993 | Huston et al. |
| 5,432,272 | A | 7/1995 | Benner |
| 5,459,255 | A | 10/1995 | Cook et al. |
| 6,083,486 | A | 7/2000 | Weissleder et al. |
| 6,417,185 | B1 | 7/2002 | Goff et al. |
| 6,489,344 | B1 | 12/2002 | Nuss et al. |
| 6,541,466 | B2 | 4/2003 | Wu et al. |
| 6,608,063 | B2 | 8/2003 | Nuss et al. |
| 7,026,343 | B2 | 4/2006 | Prochownik et al. |
| 7,206,639 | B2 | 4/2007 | Jacobsen et al. |
| 7,300,951 | B2 | 11/2007 | Kreft et al. |
| 7,468,365 | B2 | 12/2008 | Audia et al. |
| 7,544,511 | B2 | 6/2009 | Yang et al. |
| 7,872,027 | B2 | 1/2011 | Metallo et al. |
| 8,114,422 | B2 | 2/2012 | Fujii et al. |
| 8,188,069 | B2 | 5/2012 | Miller et al. |
| 8,188,131 | B2 | 5/2012 | Edge et al. |

(Continued)

FOREIGN PATENT DOCUMENTS

| | | |
|---|---|---|
| EP | 0063879 | 11/1982 |
| EP | 1949916 | 8/2011 |

(Continued)

OTHER PUBLICATIONS

Li et al. "Discovery and Characterization of a Peptide That Enhances Endosomal Escape of Delivered Proteins in Vitro and in Vivo" J. Am. Chem. Soc. 137:14084-14093. (Year: 2015).*

Aggarwal et al., "Curcumin suppresses the paclitaxel-induced nuclear factor-kappaB pathway in breast cancer cells and inhibits lung metastasis of human breast cancer in nude mice," Clin. Cancer Res., Oct. 2005, 11(20):7490-7498.

(Continued)

*Primary Examiner* — Sudhakar Katakam
*Assistant Examiner* — Zachary J Miknis
(74) *Attorney, Agent, or Firm* — Fish & Richardson P.C.

(57) ABSTRACT

Compositions and provided to induce cells of the inner ear to renter the cell cycle and to proliferate. In particular, hair cells are induced to proliferate by administration of a composition which activates the Myc and Notch. Supporting cells are induced to transdifferentiate to hair cells by inhibition of Myc and Notch activity or the activation of Atoh1. Methods of treatment include the intracellular delivery of these molecules to a specific therapeutic target.

23 Claims, 7 Drawing Sheets

Specification includes a Sequence Listing.

(56) References Cited

U.S. PATENT DOCUMENTS

| | | |
|---|---|---|
| 8,226,943 B2 | 7/2012 | Gurney et al. |
| 8,338,482 B2 | 12/2012 | Chen et al. |
| 2004/0237127 A1 | 11/2004 | Zoghbi et al. |
| 2006/0030837 A1 | 2/2006 | Mckenna et al. |
| 2007/0093878 A1 | 4/2007 | Edge et al. |
| 2009/0181944 A1 | 7/2009 | Boylan et al. |
| 2009/0232780 A1 | 9/2009 | Edge et al. |
| 2009/0258026 A2 | 10/2009 | Siebel et al. |
| 2011/0251120 A1 | 10/2011 | Wang |
| 2011/0263580 A1 | 10/2011 | Miller |
| 2011/0275719 A1 | 11/2011 | Daniels et al. |
| 2011/0305674 A1 | 12/2011 | Edge et al. |
| 2012/0100569 A1 | 4/2012 | Liu et al. |
| 2012/0107317 A1 | 5/2012 | Lau et al. |
| 2015/0071906 A1* | 3/2015 | Liu .................. C07K 14/4702 435/375 |
| 2017/0327557 A1 | 11/2017 | Chen |

FOREIGN PATENT DOCUMENTS

| | | |
|---|---|---|
| EP | 2487156 | 8/2012 |
| GB | 2019404 | 10/1979 |
| GB | 2034323 | 6/1980 |
| RU | 38486 | 6/2004 |
| WO | WO 1998/028268 | 7/1998 |
| WO | WO 2002/047671 | 6/2002 |
| WO | WO 2002/088346 | 11/2002 |
| WO | WO 2004/090110 | 4/2005 |
| WO | WO 2009/005688 | 4/2009 |
| WO | WO 2009/040423 | 4/2009 |
| WO | WO 2011/149762 | 4/2012 |
| WO | WO 2012/080926 | 6/2012 |
| WO | WO 2014/039908 | 3/2014 |
| WO | WO-2014039908 A1 * | 3/2014 ............. A61K 31/65 |
| WO | WO 2016/069906 | 5/2016 |

OTHER PUBLICATIONS

Ahmed et al., "Eya1-Six1 interaction is sufficient to induce hair cell fate in the cochlea by activating Atoh1 expression in cooperation with Sox2," Dev. Cell., Feb. 2012, 22(2):377-390.

Albright et al., "Pharmacodynamics of Selective Inhibition of γ-Secretase by Avagacestat®," J Pharmacol Exp Ther., Mar. 2013, 344(3):686-95.

Ashizawa et al., "Antitumor activity of a novel small molecule STAT3 inhibitor against a human lymphoma cell line with high STAT3 activation," Int. J. Oncol., Feb. 2011, 38(5):1245-1252.

Ausubel et al., "Preparation of a Specific Retrovirus Producer Cell Line", Current Protocols in Molecular Biology, 2001, 13 pages.

Best et al., "In Vivo Characterization of Aβ(40) Changes in Brain and Cerebrospinal Fluid Using the Novel γ-Secretase Inhibitor N-[cis-4-[(4-chlorophenyl)sulfonyl]-4-(2,5-difluorophenyl)cyclohexyl]-1,1,1-trufluoromethanesulfonamide (MRK-560) in the Rat," J Pharmacol Exp Therapeut, May 2006, 317(2):786-90.

Burns et al., "MYC Gene Delivery to Adult Mouse Utricles Stimulates Proliferation of Postmitotic Supporting Cells In Vitro", PLOS One, Oct. 2012, 7(10):e48704, 15 pages.

Christensen et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling", Journal of the American Chemical Society, 1998, 120(22):5458-5463.

Chung et al., "CD19 is a major B cell receptor-independent activator of MYC-driven B-lymphomagenesis," J. Clin. Invest., Jun. 2012, 122(6):2257-2266.

Clausen et al., "In vitro cytotoxicity and in vivo efficacy, pharmacokinetics, and metabolism of 10074-G5, a novel small-molecule inhibitor of c-Myc/Max dimerization," J. Pharmacol. Exp. Ther., Dec. 2010, 335(3):715-727.

CRC's Antisense Research and Applications, 1st ed., Crooke and Lebleu (eds.), 1993, pp. 276-278.

Daudet et al., "Notch Regulation of Progenitor Cell Behavior in Quiescent Regenerating Auditory Epithelium of Mature Birds," Dev Biol, Feb. 2009, 326(1):86-100.

De Mesmaeker et al., "Antisense Oligonucleotides", Accounts of Chemical Research, Sep. 1995, 28(9):366-374.

Engelhard et al., "Inhibitory effects of phenylbutyrate on the proliferation, morphology, migration and invasiveness of malignant glioma cells," J. Neurooncol., Apr. 1998, 37(2):97-108.

Fauq et al., "A Multigram Chemical Synthesis of the γ-Secretase Inhibitor LY411575 and its Diastereoisomers," Bioorg Med Chem Lett, Oct. 2010, 17(22):6392-5.

Fernandez et al., "Membrane Interactions of Antimicrobial Peptides from Australian Frogs," Biochimica et Biophysica Acta (BBA)—Biomembranes, Aug. 2009, 1788(8):1630-1638.

Freier et al., "The Ups and Downs of Nucleic Acid Duplex Stability: Structure-Stability Studies on Chemically-Modified DNA: RNA Duplexes," Nucleic Acids Research, Nov. 1997, 25(22):4429-4443.

Gebeyehu et al., "Novel Biotinylated Nucleotide-Analogs for Labeling and Colorimetric Detection of DNA", Nucleic Acids Research, Jun. 1987, 15(11):4513-4534.

Henikoff & Henikoff, "Amino Acid Substitution Matrices from Protein Blocks," Proc Natl Acad Sci USA, Nov. 1992, 89(22):10915-9.

Herdewin, "Heterocyclic Modifications of Oligonucleotides and Antisense Technology", Antisense & Nucleic Acid Drug Development, Aug. 2000, 10(4):297-310.

Hurley et al., "Modulating the Functional Contributions of c-Myc to the Human Endothelial Cell Cyclic Strain Response," J Vasc Res, Sep. 2009, 47(1):80-90.

Imbimbo, "Therapeutic Potential of γ-Secretase Inhibitors and Modulators," Curr Top Med Chem, 2008, 8(1):54-61.

Ishikawa et al., "Opposing Functions of Fbxw7 in Keratinocyte Growth, Differentiation and Skin Tumorigenesis Mediated Through Negative Regulation of c-Myc and Notch," Oncogene, 2013, 32:1921-32.

Jeon et al., "Notch Signaling Alters Sensory or Neuronal Cell Fate Specification of Inner Ear Stem Cells," J Neurosci, Jun. 2011, 31(23):8351-8.

Kabanov et al., "A New Class of Antivirals: Antisense Oligonucleotides Combined with a Hydrophobic Substituent Effectively Inhibit Influenza Virus Reproduction and Synthesis of Virus-Specific Proteins in MOCK Cells", FEBS Letters, Jan. 1990, 259(2):327-330.

Kaltenbach et al., "'Cisplatin-induced Hyperactivity in the Dorsal Cochlear Nucleus and its Relation to Outer Hair Cell Loss: Relevance to Tinnitus," J Neurophysiol, Aug. 2002, 88(2):699-714.

Karagiannis et al., "Rational Design of a Biomimetic Cell Penetrating Peptide Library," ACS Nano, 2013, 7(10):8616-8626, 20 pages.

Kornberg et al., "DNA Replication," The Journal of Biological Chemistry, Jan. 1988, 263(1):1-4.

Kraft et al., "Atoh1 Induces Auditory Hair Cell Recovery in Mice After Ototoxic Injury," The Laryngoscope, Jul. 2011, 123(4):992-999.

Kujawa & Liberman "Adding Insult to Injury: Cochlear Nerve Degeneration after "Temporary" Noise-Induced Hearing Loss," J Neurosci, Nov. 2009, 29(45):14077-85.

Kwan et al., "Development and Regeneration of Inner Ear," Ann NY Acad Sci, Jul. 2009, 1170:28-33.

Lauber et al., "The Cooked Food Derived Carcinogen 2-amino-1-methyl-6-phenylimidazo [4,5-b] pyridine is a Potent Oestrogen: A Mechanistic Basis for its Tissue-specific Carcinogenicity," Carcinogenesis, Dec. 2004, 25(12):2509-17.

Leary et al., "Rapid and Sensitive Colorimetric Method for Visualizing Biotin-Labeled DNA Probes Hybridized to DNA or RNA Immobilized on Nitrocellulose: Bio-Blots", PNAS, Jul. 1983, 80(13):4045-4049.

Letsinger et al., "Cholesteryl-Conjugated Oligonucleotides: Synthesis, Properties, and Activity as Inhibitors of Replication of Human Immunodeficiency Virus in Cell Culture," PNAS, Sep. 1989, 86(17):6553-6556.

Li et al., "Discovery and Characterization of a Peptide that Enhances Endosomal Escape of Delivered Proteins in vitro and in vivo," Journal of the American Chemical Society, Oct. 2015, 137(44):14084-14093.

(56) References Cited

OTHER PUBLICATIONS

Lowy et al., "Isolation of Transforming DNA: Cloning the Hamster APRT Gene," Cell, Dec. 1980, 22(3):817-23.
Mangi et al., "Mesenchymal Stem Cells Modified with Akt Prevent Remodeling and Restore Performance of Infarcted Hearts," Nat Med, Sep. 2003, 9(9):1195-1201.
Manoharan et al., "Chemical Modifications to Improve Uptake and Bioavailability of Antisense Oligonucleotides," Annals of the New York Academy of Sciences, Oct. 1992, 660(1):306-309.
Manoharan et al., "Cholic Acid-Oligonucleotide Conjugates for Antisense Applications," Bioorganic & Medicinal Chemistry Letters, Apr. 1994, 4(8):1053-1060.
Manoharan et al., "Introduction of a Lipophilic Thioether Tether in the Minor Groove of Nucleic Acids for Antisense Applications," Bioorganic & Medicinal Chemistry Letters, Dec. 1993, 3(12):2765-2770.
Manoharan et al., "Lipidic Nucleic Acids", Tetrahedron Letters, May 1995, 36(21):3651-3654.
Manoharan et al., "Oligonucleotide Conjugates: Alteration of the Pharmacokinetic Properties of Antisense Agents", Nucleosides and Nucleotides, Feb. 2007, 14(3-5):969-973.
Manoharan, "2'-Carbohydrate Modifications in Antisense Oligonucleotide Therapy: Importance of Conformation, Configuration and Conjugation," Biochimica et Biophysica Acta—Gene Structure and Expression, Dec. 1999, 1489(1):117-130.
Meinkoth et al., "Hybridization of Nucleic Acids Immobilized on Solid Supports," Analytical Biochemistry, May 1984, 138(2):267-284.
Melman et al., "hMaxi-K Gene Transfer in Males with Erectile Dysfunction: Results of the First Human Trial," Hum Gene Ther, Jan. 2007, 17(12):1165-76.
Mizuma et al., "The γ-Secretase Inhibitor MRK-003 Attenuates Pancreatic Cancer Growth in Preclinical Models," Mol Cancer Ther, Sep. 2012, 11(9):1999-2009.
Moon et al., "WNT and β-catenin Signalling: Diseases and Therapies," Nat Rev Genet, Sep. 2004, 5(9):689-699.
Mori et al., "Chemoprevention by Naturally Occurring and Synthetic Agents in Oral, Liver, and Large Bowel Carcinogenesis," J Cell Biochem Suppl, 1997, 27:35-41.
Nielsen et al., "Sequence-Selective Recognition of DNA by Strand Displacement with a Thymine-Substituted Polyamide," Science, Dec. 1991, 254(5037):1497-1500.
Oberhauser et al., "Effective Incorporation of 2'-O-Methyl-Oligoribonucleotides into Liposomes and Enhanced Cell Association through Modification with Thiocholesterol," Nucleic Acids Research, Feb. 1992, 20(3):533-538.
Oshima et al., "Differential Distribution of Stem Cells in the Auditory and Vestibular Organs of the Inner Ear," Journal of the Association for Research in Otolaryngology, Mar. 2007, 8:18-31.
Oshima et al., "Mechanosensitive Hair Cell-like Cells from Embryonic and Induced Pluripotent Stem Cells," Cell, May 2010, 141(4):704-S10.
PCT International Preliminary Report on Patentability in International Appln. No. PCT/US2015/058081, mailed on May 11, 2017, 9 pages.
PCT International Search Report and Written Opinion in International Appln. No. PCT/US2015/058081, mailed on Mar. 30, 2016, 12 pages.
Petit et al., "New Protease Inhibitors Prevent γ-Secretase-Mediated Production of Aβ40/42 Without Affecting Notch Cleavage," Nat Cell Biol, May 2001, 3(5):507-511.
Purow, "Notch Inhibition as a Promising New Approach to Cancer Therapy," Adv Exp Med Biol, 2012, 727:305-19.
Rathjen et al., "Properties and Uses of Embryonic Stem Cells: Prospects for Application to Human Biology and Gene Therapy", Reproduction, Fertility and Development, 1998, 10(1):31-47.
Renz et al., "A Colorimetric Method for DNA Hybridization", Nucleic Acids Research, Apr. 1984, 12(8) :3435-3444.
Richardson et al., "Biotin and Fluorescent Labeling of RNA Using T4 Rna Ligase," Nucleic Acids Research, Sep. 1983, 11(18):6167-6184.
Rotman, "Measurement of Activity of Single Molecules of Beta-D-Galactosidase", PNAS, Dec. 1961, 47(12):1981-1991.
Sai et al., "Induction of Cell-cycle Arrest and Apoptosis in Glioblastoma Stem-like Cells by WP1193, a Novel Small Molecule Inhibitor of the JAK2/STAT3 Pathway," J Neurooncol, May 2012, 107(3):487-501.
Saison-Behmoaras et al., "Short Modified Antisense Oligonucleotides Directed Against Ha-ras Point Mutation Induce Selective Cleavage of the mRNA and Inhibit T24 Cells Proliferation", EMBO Journal, May 1991, 10(5):1111-1118.
Samon et al., "Preclinical Analysis of the γ-Secretase Inhibitor PF-03084014 in Combination with Glucocorticoids in T-Cell Acute Lymphoblastic Leukemia," Mol Cancer Ther, Jul. 2012, 11(7):1565-75.
Scheit, "Nucleotide Analogs—Synthesis and Biological Function", FEBS Letters, Dec. 1980, 122(2):328-329.
Shea et al., "Synthesis, Hybridization Properties and Antiviral Activity of Lipid-Oligodeoxynucleotide Conjugates," Nucleic Acids Research, Jul. 1990, 18(13):3777-3783.
Shu et al., "Renewed proliferation in adult mouse cochlea and regeneration of hair cells," Nature Communications, 2019, 10:5530, 15 pages.
Slowik and Bermingham-McDonogh, "Notch signaling in mammalian hair cell regeneration," Trends in Developmental Biology, 2013, 7:73-89.
Smetanina et al., "Ortho-aminoazotoluene Activates Mouse Constitutive Androstane Receptor (mCAR) and Increases Expression of mCAR Target Genes," Toxicol Appl Pharmacol, Aug. 2011, 255(1):76-85.
Smith et al., "The Synthesis of Oligonucleotides Containing an Aliphatic Amino Group at the 5' Terminus: Synthesis of Fluorescent DNA Primers for Use in DNA Sequence Analysis," Nucleic Acids Research, Apr. 1985, 13(7):2399-2412.
Svinarchuk et al., "Inhibition of HIV Proliferation in MT-4 Cells by Antisense Oligonucleotide Conjugated to Lipophilic Groups," Biochimie, 1993, 75(1-2):49-54.
Takahashi et al., "Sulindac Sulfide is a Noncompetitive γ-Secretase Inhibitor that Preferentially Reduces Aβ42 Generation," J Biol Chem, May 2003, 278(20):18664-70.
Takebayashi et al., "Multiple Roles of Notch Signaling in Cochlear Development," Dev Biol, Jul. 2007, 307(1):165-78.
Thompson et al., "Engineering and Identifying Supercharged Proteins for Macromolecule Delivery into Mammalian Cells," Methods in Enzymology, 2012, 503:293-319.
Tolcher et al., "Phase I Study of RO4929097, a Gamma Secretase Inhibitor of Notch Signaling, in Patients with Refractory Metastatic of Locally Advanced Solid Tumors," J Clin Oncol, Jul. 2012, 30(19):2348-53.
Toulme, "New Candidates for True Antisense", Nature Biotechnology, 2001, 19:17-18.
Uhlmann, "Recent Advances in Medicinal Chemistry of Antisense Oligonucleotides," Current Opinion in Drug Discovery & Development, Mar. 2000, 3(2):203-213.
Wigler et al., "Transfer of Purified Herpes Virus Thymidine Kinase Gene to Cultured Mouse Cells," Cell, May 1977, 11(1):223-32.
Wiles, "Embryonic Stem Cell Differentiation In Vitro," Methods in Enzymology, Jan. 1993, 225:900-918.
Wolfe et al., "A Substrate-based Difluoro Ketone Selectively Inhibits Alzheimer's γ-Secretase Activity," J Med Chem, Jan. 1998, 41(1):6-9.
Zhang et al., "Orally Bioavailable Small-molecule Inhibitor of Transcription Factor STAT3 Regresses Human Breast and Lung Cancer Xenografts," Proc Natl Acad Sci USA, Jun. 2012, 109(24):9623-8.
Zheng et al., "Studies on the Pharmacokinetics and Metabolism of γ-Secretase Inhibitor BMS-299897, and Exploratory Investigation of CYP Enzyme Induction," Xenobiotica, Jan. 2009, 39(7):544-55.

* cited by examiner

Oct4/Phal/DAPI

NESTIN/Phal/DAPI

Oct4/Phal/Pax2/DAPI

NF/Myo7a/pan-Cyt/DAPI

NF/Myo7a/pan-Cyt/DAPI

SEQUENCE LISTING

```
<160> NUMBER OF SEQ ID NOS: 59

<210> SEQ ID NO 1
<211> LENGTH: 238
<212> TYPE: PRT
<213> ORGANISM: Aequorea victoria

<400> SEQUENCE: 1

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
```

```
225                 230                 235

<210> SEQ ID NO 2
<211> LENGTH: 13
<212> TYPE: PRT
<213> ORGANISM: Litoria aurea

<400> SEQUENCE: 2

Gly Leu Phe Asp Ile Ile Lys Lys Ile Ala Glu Ser Phe
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Phe Asp Ile Ile Lys Lys Ile Ala Glu Ser Phe
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ala Phe Asp Ile Ile Lys Lys Ile Ala Glu Ser Phe
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Leu Ala Asp Ile Ile Lys Lys Ile Ala Glu Ser Phe
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Leu Phe Ala Ile Ile Lys Lys Ile Ala Glu Ser Phe
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

```
Gly Leu Phe Asp Ala Ile Lys Lys Ile Ala Glu Ser Phe
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Leu Phe Asp Ile Ala Lys Lys Ile Ala Glu Ser Phe
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Leu Phe Asp Ile Ile Ala Lys Ile Ala Glu Ser Phe
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Leu Phe Asp Ile Ile Lys Ala Ile Ala Glu Ser Phe
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Leu Phe Asp Ile Ile Lys Lys Ala Ala Glu Ser Phe
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Leu Phe Asp Ile Ile Lys Lys Ile Ala Ala Ser Phe
1               5                   10

<210> SEQ ID NO 13
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 13

Gly Leu Phe Asp Ile Ile Lys Lys Ile Ala Glu Ala Phe
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Phe Asp Ile Ile Lys Lys Ile Ala Glu Ser Ala
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Leu Phe Asp Ile Ile His Lys Ile Ala Glu Ser Phe
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Leu Phe Asp Ile Ile Lys His Ile Ala Glu Ser Phe
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Leu Phe Asp Ile Ile Lys Lys Ile Ala His Ser Phe
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Leu Phe Asp Ile Ile Arg Lys Ile Ala Glu Ser Phe
1               5                   10
```

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Leu Phe Asp Ile Ile Lys Arg Ile Ala Glu Ser Phe
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Leu Phe Asp Ile Ile Lys Lys Ile Ala Arg Ser Phe
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Leu Phe Asp Ile Ile Lys Lys Ile Ala Asp Ser Phe
1               5                   10

<210> SEQ ID NO 22
<211> LENGTH: 14
<212> TYPE: PRT
<213> ORGANISM: Rana catesbeiana

<400> SEQUENCE: 22

Phe Leu Phe Pro Leu Ile Thr Ser Phe Leu Ser Lys Val Leu
1               5                   10

<210> SEQ ID NO 23
<211> LENGTH: 13
<212> TYPE: PRT
<213> ORGANISM: Rana catesbeiana

<400> SEQUENCE: 23

Phe Ile Ser Ala Ile Ala Ser Met Leu Gly Lys Phe Leu
1               5                   10

<210> SEQ ID NO 24
<211> LENGTH: 13
<212> TYPE: PRT
<213> ORGANISM: Litoria ewingi

<400> SEQUENCE: 24

Gly Trp Phe Asp Val Val Lys His Ile Ala Ser Ala Val
1               5                   10

<210> SEQ ID NO 25
<211> LENGTH: 13
<212> TYPE: PRT

```
<213> ORGANISM: Hylarana picturata

<400> SEQUENCE: 25

Phe Phe Gly Ser Val Leu Lys Leu Ile Pro Lys Ile Leu
1               5                   10

<210> SEQ ID NO 26
<211> LENGTH: 13
<212> TYPE: PRT
<213> ORGANISM: Litoria sp.
<220> FEATURE:
<223> OTHER INFORMATION: Litoria aurea or Litoria raniformis

<400> SEQUENCE: 26

Gly Leu Phe Asp Ile Ile Lys Lys Ile Ala Glu Ser Phe
1               5                   10

<210> SEQ ID NO 27
<211> LENGTH: 13
<212> TYPE: PRT
<213> ORGANISM: Calliphora vicina

<400> SEQUENCE: 27

His Gly Val Ser Gly His Gly Gln His Gly Val His Gly
1               5                   10

<210> SEQ ID NO 28
<211> LENGTH: 13
<212> TYPE: PRT
<213> ORGANISM: Rana temporaria

<400> SEQUENCE: 28

Phe Leu Pro Leu Ile Gly Arg Val Leu Ser Gly Ile Leu
1               5                   10

<210> SEQ ID NO 29
<211> LENGTH: 13
<212> TYPE: PRT
<213> ORGANISM: Litoria sp.
<220> FEATURE:
<223> OTHER INFORMATION: Litoria aurea or Litoria raniformis

<400> SEQUENCE: 29

Gly Leu Phe Asp Ile Ile Lys Lys Ile Ala Glu Ser Ile
1               5                   10

<210> SEQ ID NO 30
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 30

Gly Leu Leu Asp Ile Val Lys Lys Val Val Gly Ala Phe Gly Ser Leu
1               5                   10                  15

<210> SEQ ID NO 31
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 31

Gly Leu Phe Asp Ile Val Lys Lys Val Val Gly Ala Leu Gly Ser Leu
```

-continued

```
<210> SEQ ID NO 32
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 32

Gly Leu Phe Asp Ile Val Lys Lys Val Val Gly Ala Ile Gly Ser Leu
1               5                   10                  15

<210> SEQ ID NO 33
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 33

Gly Leu Phe Asp Ile Val Lys Lys Val Val Gly Thr Leu Ala Gly Leu
1               5                   10                  15

<210> SEQ ID NO 34
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 34

Gly Leu Phe Asp Ile Val Lys Lys Val Val Gly Ala Phe Gly Ser Leu
1               5                   10                  15

<210> SEQ ID NO 35
<211> LENGTH: 16
<212> TYPE: PRT
<213> ORGANISM: Litoria sp.
<220> FEATURE:
<223> OTHER INFORMATION: Litoria aurea or Litoria raniformis

<400> SEQUENCE: 35

Gly Leu Phe Asp Ile Ala Lys Lys Val Ile Gly Val Ile Gly Ser Leu
1               5                   10                  15

<210> SEQ ID NO 36
<211> LENGTH: 17
<212> TYPE: PRT
<213> ORGANISM: Litoria sp.
<220> FEATURE:
<223> OTHER INFORMATION: Litoria aurea or Litoria raniformis

<400> SEQUENCE: 36

Gly Leu Phe Asp Ile Val Lys Lys Ile Ala Gly His Ile Ala Gly Ser
1               5                   10                  15

Ile

<210> SEQ ID NO 37
<211> LENGTH: 17
<212> TYPE: PRT
<213> ORGANISM: Litoria sp.
<220> FEATURE:
<223> OTHER INFORMATION: Litoria aurea or Litoria raniformis

<400> SEQUENCE: 37
```

-continued

```
Gly Leu Phe Asp Ile Val Lys Lys Ile Ala Gly His Ile Ala Ser Ser
1               5                   10                  15

Ile

<210> SEQ ID NO 38
<211> LENGTH: 17
<212> TYPE: PRT
<213> ORGANISM: Litoria sp.
<220> FEATURE:
<223> OTHER INFORMATION: Litoria aurea or Litoria raniformis

<400> SEQUENCE: 38

Gly Leu Phe Asp Ile Val Lys Lys Ile Ala Gly His Ile Val Ser Ser
1               5                   10                  15

Ile

<210> SEQ ID NO 39
<211> LENGTH: 13
<212> TYPE: PRT
<213> ORGANISM: Rana temporaria

<400> SEQUENCE: 39

Phe Val Gln Trp Phe Ser Lys Phe Leu Gly Arg Ile Leu
1               5                   10

<210> SEQ ID NO 40
<211> LENGTH: 16
<212> TYPE: PRT
<213> ORGANISM: Litoria citropa

<400> SEQUENCE: 40

Gly Leu Phe Asp Val Ile Lys Lys Val Ala Ser Val Ile Gly Gly Leu
1               5                   10                  15

<210> SEQ ID NO 41
<211> LENGTH: 16
<212> TYPE: PRT
<213> ORGANISM: Litoria citropa

<400> SEQUENCE: 41

Gly Leu Phe Asp Ile Ile Lys Lys Val Ala Ser Val Val Gly Gly Leu
1               5                   10                  15

<210> SEQ ID NO 42
<211> LENGTH: 16
<212> TYPE: PRT
<213> ORGANISM: Litoria citropa

<400> SEQUENCE: 42

Gly Leu Phe Asp Ile Ile Lys Lys Val Ala Ser Val Ile Gly Gly Leu
1               5                   10                  15

<210> SEQ ID NO 43
<211> LENGTH: 15
<212> TYPE: PRT
<213> ORGANISM: Rana dybowskii

<400> SEQUENCE: 43

Val Trp Pro Leu Gly Leu Val Ile Cys Lys Ala Leu Lys Ile Cys
1               5                   10                  15

<210> SEQ ID NO 44
<211> LENGTH: 14
<212> TYPE: PRT
```

<213> ORGANISM: Rana cascadae

<400> SEQUENCE: 44

Asn Phe Leu Gly Thr Leu Val Asn Leu Ala Lys Lys Ile Leu
1               5                   10

<210> SEQ ID NO 45
<211> LENGTH: 13
<212> TYPE: PRT
<213> ORGANISM: Rana ornativentris

<400> SEQUENCE: 45

Phe Leu Pro Leu Ile Gly Lys Ile Leu Gly Thr Ile Leu
1               5                   10

<210> SEQ ID NO 46
<211> LENGTH: 13
<212> TYPE: PRT
<213> ORGANISM: Rana boylii

<400> SEQUENCE: 46

Phe Leu Pro Ile Ile Ala Lys Val Leu Ser Gly Leu Leu
1               5                   10

<210> SEQ ID NO 47
<211> LENGTH: 13
<212> TYPE: PRT
<213> ORGANISM: Unknown
<220> FEATURE:
<223> OTHER INFORMATION: Description of Unknown: Antimicrobial peptide

<400> SEQUENCE: 47

Phe Leu Pro Ile Val Gly Lys Leu Leu Ser Gly Leu Leu
1               5                   10

<210> SEQ ID NO 48
<211> LENGTH: 13
<212> TYPE: PRT
<213> ORGANISM: Rana virgatipes

<400> SEQUENCE: 48

Phe Leu Ser Ser Ile Gly Lys Ile Leu Gly Asn Leu Leu
1               5                   10

<210> SEQ ID NO 49
<211> LENGTH: 13
<212> TYPE: PRT
<213> ORGANISM: Pelophylax saharica

<400> SEQUENCE: 49

Phe Leu Ser Gly Ile Val Gly Met Leu Gly Lys Leu Phe
1               5                   10

<210> SEQ ID NO 50
<211> LENGTH: 9
<212> TYPE: PRT
<213> ORGANISM: Apis mellifera

<400> SEQUENCE: 50

Thr Pro Phe Lys Leu Ser Leu His Leu
1               5

<210> SEQ ID NO 51
<211> LENGTH: 14
<212> TYPE: PRT

<213> ORGANISM: Hyla punctata

<400> SEQUENCE: 51

Gly Ile Leu Asp Ala Ile Lys Ala Ile Ala Lys Ala Ala Gly
1               5                   10

<210> SEQ ID NO 52
<211> LENGTH: 12
<212> TYPE: PRT
<213> ORGANISM: Litoria sp.
<220> FEATURE:
<223> OTHER INFORMATION: Litoria aurea or Litoria raniformis

<400> SEQUENCE: 52

Leu Phe Asp Ile Ile Lys Lys Ile Ala Glu Ser Phe
1               5                   10

<210> SEQ ID NO 53
<211> LENGTH: 25
<212> TYPE: PRT
<213> ORGANISM: Unknown
<220> FEATURE:
<223> OTHER INFORMATION: Description of Unknown: Antimicrobial peptide

<400> SEQUENCE: 53

Leu Phe Asp Ile Ile Lys Lys Ile Ala Glu Ser Gly Phe Leu Phe Asp
1               5                   10                  15

Ile Ile Lys Lys Ile Ala Glu Ser Phe
            20                  25

<210> SEQ ID NO 54
<211> LENGTH: 24
<212> TYPE: PRT
<213> ORGANISM: Cryptotympana dubia

<400> SEQUENCE: 54

Gly Leu Leu Asn Gly Leu Ala Leu Arg Leu Gly Lys Arg Ala Leu Lys
1               5                   10                  15

Lys Ile Ile Lys Arg Leu Cys Arg
            20

<210> SEQ ID NO 55
<211> LENGTH: 14
<212> TYPE: PRT
<213> ORGANISM: Unknown
<220> FEATURE:
<223> OTHER INFORMATION: Description of Unknown: Antimicrobial peptide

<400> SEQUENCE: 55

Gly His His His His His His His His His His His His His
1               5                   10

<210> SEQ ID NO 56
<211> LENGTH: 10
<212> TYPE: PRT
<213> ORGANISM: Unknown
<220> FEATURE:
<223> OTHER INFORMATION: Description of Unknown: Antimicrobial peptide

<400> SEQUENCE: 56

Phe Lys Cys Arg Arg Trp Gln Trp Arg Met
1               5                   10

<210> SEQ ID NO 57
<211> LENGTH: 10

```
<212> TYPE: PRT
<213> ORGANISM: Vigna sesquipedalis

<400> SEQUENCE: 57

Lys Thr Cys Glu Asn Leu Ala Asp Thr Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phospho-Ser

<400> SEQUENCE: 58

Lys Glu Ala Pro Pro Ala Pro Pro Gln Ser Pro
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Phospho-Ser

<400> SEQUENCE: 59

Gly Lys Glu Ala Pro Pro Ala Pro Pro Gln Ser Pro
1               5                   10
```

EFFICIENT DELIVERY OF THERAPEUTIC MOLECULES TO CELLS OF THE INNER EAR

CROSS REFERENCE TO RELATED APPLICATIONS

This is a divisional application of U.S. patent application Ser. No. 15/523,317, filed Apr. 28, 2017, which is a national stage filing in accordance with 35 U.S.C. § 371 of PCT/US2015/058081, filed Oct. 29, 2015, which claims the benefit of the priority of U.S. provisional patent application No. 62/072,220, filed Oct. 29, 2014, the contents of which are incorporated herein by reference.

SEQUENCE LISTING

This application contains a sequence listing that has been submitted electronically as an ASCII text file named "Sequence_Listing.txt." The ASCII text file, created on May 20, 2022, is 16 kilobytes in size. The material in the ASCII text file is hereby incorporated by reference in its entirety.

FIELD OF THE INVENTION

The present invention relates to protein therapeutics including compositions, methods of treatment and delivery of the therapeutic molecules for inducing inner ear cells to reenter the cell cycle and to proliferate.

BACKGROUND

One of the most common types of hearing loss is sensorineural deafness that is caused by the loss of hair cells or hair cell function. Hair cells are sensory cells in the cochlea responsible for transduction of sound into an electrical signal. The human inner ear contains only about 15,000 hair cells per cochlea at birth, and, although these cells can be lost as a result of various genetic or environmental factors (e.g., noise exposure, ototoxic drug toxicity, viral infection, aging, and genetic defects), the lost or damaged cells cannot be replaced. Hair cells also are found in the utricle of the vestibule, an organ which regulates balance. Therefore, hair cell regeneration is an important approach to restoring hearing and vestibular function.

Studies of regeneration of hair cells in mature mammalian inner ear to date have focused on transdifferentiation of existing supporting cells. Supporting cells underlie, at least partially surround, and physically support sensory hair cells within the inner ear. Examples of supporting cells include inner rod (pillar cells), outer rod (pillar cells), inner phalangeal cells, outer phalangeal cells (of Deiters), cells of Held, cells of Hensen, cells of Claudius, cells of Boettcher, interdental cells and auditory teeth (of Huschke). Transdifferentiation of supporting cells to hair cells by overexpression or activation of Atonal Homolog 1 (Atoh1) in supporting cells or by exposure of supporting cells to Atoh1 agonists is one such approach to generating new hair cells. One limitation to this approach, however, is that transdifferentiation of supporting cells to hair cells diminishes the existing population of supporting cells, which can impair inner ear function. In addition, overexpression of Atoh1 in aged inner ear or flat epithelium, which lacks supporting cells, is not sufficient to induce hair cells. Furthermore, it is not clear if all types of supporting cells can be transdifferentiated into hair cells upon Atoh1 overexpression.

Other studies of hair cell regeneration have examined cell cycle reentry for hair cells in embryonic or neonatal mice by, for example, blocking Rb 1 and p27kip 1. However similar manipulations in the adult inner ear have not induced cell cycle reentry. In addition, the hair cells in embryonic and neonatal mice that reenter the cell cycle, in general, subsequently die.

Over 150 types of genetic deafness are due to mutations in genes that affect both hair cells and supporting cells. For example, mutations in Myosin Vila (Myo7a) cause hair cell stereocilia abnormalities that lead to permanent deafness. Mutations in GJB2 (connexin 26) cause damage to supporting cells that lead to the most common form of genetic deafness.

Approaches (e.g., gene therapy and anti-sense oligonucleotide therapy) have been developed as potential treatments for hereditary deafness. However, most of these defects occur during embryonic development. By birth, affected hair cells and supporting cells already have died or are severely degenerated, making intervention difficult. Therefore, to treat genetic deafness, there is an ongoing need to regenerate hair cells and/or supporting cells in utero and after birth, which can be combined with other approaches to correct the genetic defects underlying the disease.

In addition, inner ear non-sensory cells (e.g., fibrocytes in the ligament) play essential roles in hearing. Inner ear non-sensory cells can be damaged by factors such as noise and aging, which contribute to hearing loss. These cell types, like many of those in the inner ear, lack the capacity to regenerate spontaneously after damage. Because spontaneous regeneration does not occur in the mammalian inner ear, recovery from hearing loss requires intervention to replace any inner ear cell types that are lost or degenerated. Therefore, there is an ongoing need to regenerate hair and/or supporting cells within the mammalian ear, in particular in the inner ear, to replace those lost, for example, by genetic or environmental factors. The regenerated hair and supporting cells may be used to slow the loss of hearing and/or vestibular function and/or partially or fully to restore loss of hearing and/or vestibular function.

SUMMARY

Embodiments of the invention are directed, inter alia, to therapeutic compositions and delivery of these compositions to the inner ear of patients. These compositions activate Myc and Notch in inner ear cells, the hair cells and/or supporting cells which results in the induction of hair cell and/or supporting cell proliferation. Inhibition of Myc and/or Notch in the supporting cells induces transdifferentiation of supporting cells to hair cells. In addition, activating Atoh1 induces transdifferentiation of supporting cells to hair cells. The proliferation and the subsequent differentiation of the cell into hair and/or supporting cells can restore or improve hearing and/or vestibular function.

Activation and subsequent inactivation of Myc and Notch1 can lead to regeneration of cells within the strial vascularis that includes marginal cells, intermediate cells, basal cells and fibrocytes. Degeneration of strial vascularis causes hearing loss. Regeneration of any of the cell types could lead to hearing recovery. Accordingly, embodiments of the invention include all cells and cell types associated with hearing and hearing loss, including neural cells, such as for example, neurites.

In an embodiment, a method of regenerating inner ear cells in vitro or in vivo comprises contacting a cell in vitro or administering to an inner ear of a patient in need of such treatment, a composition comprising an effective amount of a supercharged protein comprising one or more proteins, peptides or variants thereof, which modulate expression or activity of Myc, Notch, Atonal Homolog 1 (Atoh1), Notch Intracellular domain (NICD) proteins, Notch Intracellular domain (NICD) peptides, or combinations thereof within a cell, to induce proliferation or cell cycle re-entry in hair and supporting cells of the inner ear. The method may also include the step of inhibiting Myc and/or Notch expression or activity after proliferation of the hair or supporting cell to induce differentiation or transdifferentiation of the cell and/ or at least one of its daughter cells into a hair cell. The method may also further include the step of activating Atoh1 to induce transdifferentiation of the supporting cells to hair cells. The Myc activity in the hair and/or supporting cells is increased by administering an effective amount of Myc protein, Myc peptides or Myc activators linked to supercharged proteins, such as, for example, green fluorescent proteins (s-GFP) or variants thereof. The Notch activity is increased by administering an effective amount of Notch protein, Notch peptides, Notch activators, Notch Intracellular domain (NICD) proteins, Notch Intracellular domain (NICD) peptides, or combinations thereof, linked to GFP or variants thereof. Inhibition of Myc and/or Notch can be accomplished through administration of inhibitors or once the activator has degraded over time. Activation of Atoh1 is accomplished by the delivery of Atoh1 proteins, Atoh1 peptides, Atoh1 activators, or combinations thereof, linked to s-GFP or variants thereof.

In another embodiment, a method of regenerating inner ear cells in vitro or in vivo comprises contacting a cell in vitro or administering to an inner ear of patient in need of such treatment, a composition comprising an effective amount of a supercharged protein comprising one or more proteins, peptides or variants thereof, which activate Myc, Notch, Atonal Homolog 1 (Atoh1), Notch Intracellular domain (NICD), or combinations thereof within a cell, to induce proliferation or cell cycle re-entry in hair and supporting cells of the inner ear.

In another embodiment, a method of inducing proliferation and transdifferentiation of inner ear cells, in vivo or in vitro, comprises contacting inner ear cells comprising, strial vascularis, hair cells, or supporting cells of the inner ear with a composition which increases expression or activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in hair and supporting cells of the inner ear; administering after a pre-determined period, inhibitors to inhibit Notch and Myc activity followed by a composition that activates Atoh1 and induces the transdifferentiation of the supporting cells. The administration of the Myc and/or Notch inhibitors can be optional. The activity can be measured over time based on the half-life ($t_{1/2}$) of the protein and the Atoh1 activator can be administered once the activity of the Myc and/or Notch has decreased to a desired level.

In another embodiment, a method of preventing or treating deafness or disorders thereof, in a patient in need of such treatment comprises contacting inner ear cells comprising, strial vascularis, hair cells, or supporting cells of the inner ear with a composition which increases activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in hair and supporting cells of the inner ear; administering inhibitors to inhibit Notch and/or Myc activity; administering a composition comprising activators of Atoh1 wherein the Atoh1 composition induces the transdifferentiation of the supporting cells.

In another embodiment, a method of preventing or treating deafness or disorders thereof, in a patient in need of such treatment comprises contacting inner ear cells comprising, strial vascularis, hair cells, or supporting cells of the inner ear with a composition which increases activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in hair and supporting cells of the inner ear; administering inhibitors to inhibit Notch and Myc activity; and, administering an activator of Atoh1, wherein the Atoh1 activator induces the transdifferentiation of the supporting cells to hair cells.

In yet another embodiment, a method of inducing proliferation and transdifferentiation of inner ear cells, in vivo or in vitro, comprises contacting inner ear cells comprising, strial vascularis, hair cells, or supporting cells of the inner ear with a composition which increases activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in hair and supporting cells of the inner ear; wherein after Notch and/or Myc activity is decreased or inhibited, administering an activator of Atoh1, to induce the transdifferentiation of the supporting cells to hair cells.

In yet another embodiment, a method of preventing or treating deafness or disorders thereof, in a patient in need of such treatment comprises contacting inner ear cells comprising, strial vascularis, hair cells, or supporting cells of the inner ear with a composition which increases activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in hair and supporting cells of the inner ear; wherein after Notch and/or Myc activity is decreased or inhibited, administering an activator of Atoh1, to induce the transdifferentiation of the supporting cells to hair cells.

In another embodiment, a method of delivering a therapeutic molecule to cells of the inner ear of a patient, comprises administering to the inner ear of a patient a chimeric molecule comprising at least one protein or peptide fused, complexed or linked to one or more anionic molecules. The chimeric molecule comprises one or more gene editing agents, transcriptional modulators, translational modulators, post-translational modulators, and/or modulators that regulate protein expression, function, activity or combinations thereof. Examples of gene editing agents include, without limitation: transcriptional activators, transcriptional repressors, recombinases, nucleases, DNA-binding proteins or nucleic acids, or combinations thereof. The anionic molecules comprise: oligonucleotides, polynucleotides, proteins, peptides, peptide nucleic acids (PNA), synthetic molecules or combinations thereof. Oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof. The chimeric molecule also comprises a supercharged protein or variants thereof and antimicrobial or membrane destabilizing peptides, for example, aurein, or variants thereof.

In an embodiment, a method of inducing transdifferentiation of inner ear cells comprises contacting an inner ear cell in vitro or in vivo with a composition which transiently increases activity of Myc proteins or peptides, Notch proteins or peptides, Notch Intracellular domain (NICD) proteins, Notch Intracellular domain (NICD) peptides, variants or combinations thereof within a cell, to induce transdifferentiation of supporting cells of the inner ear without proliferation; wherein after Notch activity is decreased or inhibited by a Notch inhibitor, optionally, administering an activator of Atoh1, to induce the transdifferentiation of the supporting cells to hair cells.

In another embodiment, a method of regenerating inner ear cells comprises inducing proliferation or cell cycle reentry of inner ear cells in vitro or in vivo, the method comprising contacting a cell in vitro or administering to an inner ear of a patient in need of such treatment, a composition comprising an effective amount of a supercharged protein comprising one or more proteins, peptides or variants thereof, which modulate expression or activity of Myc, Notch, Atonal Homolog 1 (Atoh1), Notch Intracellular domain (NICD) proteins, Notch Intracellular domain (NICD) peptides, or combinations thereof within a cell, to induce proliferation or cell cycle re-entry in inner ear cells.

In another embodiment, a method for protecting and/or treating hearing loss in a patient in need of such treatment, comprises contacting a cell in vitro or administering to an inner ear of a patient in need of such treatment, a composition comprising an effective amount of a supercharged protein comprising one or more proteins, peptides or variants thereof, which modulate expression or activity of Myc, Notch, Atonal Homolog 1 (Atoh1), Notch Intracellular domain (NICD) proteins, Notch Intracellular domain (NICD) peptides, or combinations thereof within a cell, to induce neurite growth, proliferation or cell cycle re-entry of inner ear cells, proliferation of hair cells, proliferation of supporting cells, and/or transdifferentiation of supporting cells.

Other aspects are described infra.

BRIEF DESCRIPTION OF THE DRAWINGS

FIG. 1A: The scala media (cochlear duct) of P0 floxP-tdTomato mice (n=4) were injected with 0.3 µL of 23 µM (−30)GFP-Cre in 50% RNAiMAX or with RNAiMAX alone (control). After 5 days, tdTomato expression indicative of Cre-mediated recombination was visualized using immunohistology. Red=tdTomato; green=Myo7a; white=Sox2; blue=DAPI. Yellow brackets indicate the outer hair cell (OHC) region. FIG. 1B: Ten days after (−30)GFP-Cre delivery, intact espin (Esp)-expressing stereocilia of tdTomato-positive outer hair cells were present (arrow), similar to stereocilia in control cochlea. Red=tdTomato; green=Esp; white=Sox2; blue=DAPI, Scale bars: 10 µm.

FIG. 2A: At 5 µM, tdT labeling was mainly in some IHC and SC. FIG. 2B: At 22.5 tdT labeling was in most IHC and OHC. FIG. 2C: At 50 µM, tdT was seen in most IHC and OHC, as well as a large number of SC. IHC loss was seen under the condition. FIG. 2D: In mice injected with 50 µM (+36)GFP-Cre, very few IHC and HC were labeled with tdT. FIG. 2E: In Opti-MEM injected control mice, no tdT labeling was detected in any inner ear cells. Scale bars: 10 µm.

FIGS. 6A-6C show that Ad-Atoh1 infection in adult Atoh1-GFP cochlea results in GFP (a readout for Atoh1 expression) in IHCs (arrows), cells in the IHC region (solid arrowheads) and the OHC region (open arrowheads). None of the infected SCs became new HCs. A'-C'. Cross section (along the dashed line in FIG. 6C) shows GFP in MC, inner phalangeal cell (arrow) and outer pillar cell (C', arrowhead). FIGS. 6D-6F show that Dox induction and Ad-Atoh1 infection induced division in adult rtTa/tet-Myc/tet-NICD cochlea in vivo and supernumerary HCs (bracket) in the IHC region. D'-F'. Cross section along the solid line (FIG. 6F) shows two ectopic HCs (eHC) adjacent to an IHC. D"-F". Cross section along the dashed line (FIG. 6F) shows numerous ectopic HCs adjacent to an MC, some of which are EdU$^+$(eHC). Scale bar: 10 µm. FIG. 6G shows that Dox+ ad-Atoh1 significantly increased the number of HCs in the IHC region. FIG. 6H shows that in the limbus region, HCs are regenerated from dividing and non-dividing cells; whereas no HCs are seen in control limbus. Scale bars: 10 µm.

FIGS. 7A-7C show spheres from adult cochleas after 2 (FIG. 7A), 4 (FIG. 7B) and 7 (FIG. 7C) passages. FIGS. 7D-7F show Oct4 labeled undifferentiated spheres (FIG. 7D, solid sphere; FIG. 7E, hollow sphere), and indication of activation of stem cell gene. Phal: Phalloidin labels actin. Nestin, another stem cell gene, labels sphere (FIG. 7F). FIGS. 7G-7I show that under differentiated conditions, Pax2, an early inner ear progenitor gene, is detected in the sphere. Myo7a, a hair cell marker, stains differentiated sphere cells. NF (neurofilament) stains many cells under the condition, an indication that some cells start to become neurons (FIG. 7I). pan-Cyt: pan-cytokeratin.

DETAILED DESCRIPTION

Figure 1A:
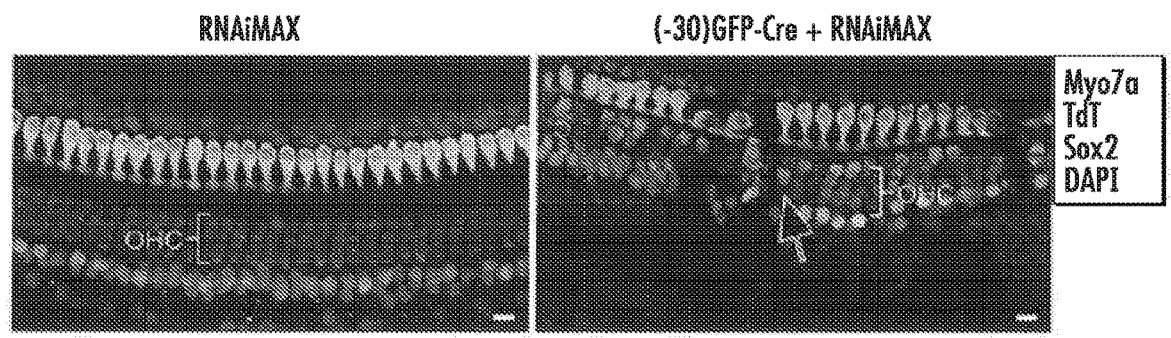
FIGS. 1A and 1B show the in vivo delivery of Cre recombinase to hair cells in the mouse inner ear.

Embodiments of the invention are directed to compositions for the efficient intracellular delivery of therapeutic proteins to the nucleus or cytoplasm, in particular of hair cells and/or supporting cells of the inner ear. Conventional methods of protein delivery typically rely on cationic peptides or proteins to facilitate endocytosis, but suffer from low tolerance for serum proteins, poor endosomal escape, and limited in vivo efficacy. The reagents embodied herein can potently deliver proteins that are fused to polynucleotides, oligonucleotides, negatively supercharged proteins, that contain natural anionic domains, or that natively bind to anionic nucleic acids. The methods and compositions can be used to increase a population of hair cells and/or supporting cells diminished by environmental or genetic factors. Using the methods and compositions described herein, it may be possible to preserve or improve hearing and/or vestibular function in the inner ear.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

"Optional" or "optionally" means that the subsequently described event or circumstance can or cannot occur, and that the description includes instances where the event or circumstance occurs and instances where it does not.

As used herein, a "chimeric" molecule is one which comprises one or more unrelated types of components or contain two or more chemically distinct regions or domains which can be conjugated to each other, fused, linked, translated, attached via a linker, chemically synthesized, expressed from a nucleic acid sequence, etc. For example, an antimicrobial or membrane destabilizing peptide and an unrelated peptide, a peptide and a nucleic acid sequence, a peptide and a detectable label, unrelated peptide sequences, unrelated nucleic acid sequence and the like.

The term "anionic" molecule is one which comprises one or more "anionic" domains which confer an overall net anionic charge to the molecule. Accordingly, the chimeric molecule can be an anionic molecule.

A "supercharged" molecule is a molecule e.g. peptide, having a positive or negative charge and when it is connected to another molecule confers an overall positive or negative charge to the entire molecule.

As used herein, a "membrane destabilizing domain" is one which disrupts a cellular membrane in vitro or in vivo, for example, aurein. The term encompasses proteins, peptides, polynucleotides, oligonucleotides, bacterial or viral molecules, antimicrobial peptides, antibacterial molecules, microtubules, synthetic or natural molecules. A chimeric molecule embodied herein, further comprises one or more membrane destabilizing domains.

As used herein, the terms "associated with," "conjugated," "linked," "attached," and "tethered," when used with respect to two or more moieties, means that the moieties or domains are physically associated or connected with one another, either directly or via one or more additional moieties that serves as a linking agent, to form a structure that is sufficiently stable so that the moieties remain physically associated under the conditions in which the structure is used, e.g., physiological conditions. The term "connected" will be used for the sake of brevity and is meant to include all possible methods of physically associating each domain of the chimeric molecule to each other. For example, a supercharged protein is typically associated with or connected to a nucleic acid by a mechanism that involves non-covalent binding (e.g., electrostatic interactions). In certain embodiments, a positively charged, supercharged protein is associated with a nucleic acid through electrostatic interactions to form a complex. In some embodiments, a sufficient number of weaker interactions can provide sufficient stability for moieties to remain physically associated under a variety of different conditions. In certain embodiments, the agent to be delivered is covalently bound to the supercharged protein.

As used herein, the term, "Notch" refers to the Notch family of signaling proteins, which includes Notch 1, Notch 2, Notch 3 and Notch 4, or notch intracellular domain (NICD). The full length sequence of human Notch1 appears, for example, in the NCBI protein database under accession no. NP_060087.3 (see ncbi.nlm.nih.gov). Members of this Type 1 transmembrane protein family share structural characteristics including an extracellular domain consisting of multiple epidermal growth factor-like (EGF) repeats, and an intracellular domain consisting of multiple, different domain types. Notch family members play a role in a variety of developmental processes by controlling cell fate decisions. Notch 1 is cleaved in the trans-Golgi network, and presented on the cell surface as a heterodimer. Notch 1 functions as a receptor for membrane bound ligands Jagged 1, Jagged 2 and Delta 1 to regulate cell-fate determination. Upon ligand activation through the released notch intracellular domain (NICD) it forms a transcriptional activator complex with RBPJ/RBPSUH and activates genes of the enhancer of split locus. Notch 1 affects the implementation of differentiation, proliferation and apoptotic programs.

As used herein, "Myc" refers to the Myc family of transcription factors. Myc is a multifunctional, nuclear phosphoprotein that plays a role in cell cycle progression, apoptosis and cellular transformation. The full length sequence of human Myc appears, for example, in the NCBI protein database under accession no. NP_002458.2 (see ncbi.nlm.nih.gov). Myc functions as a transcription factor that regulates transcription of specific target genes. Mutations, overexpression, rearrangement and translocation of this gene have been associated with a variety of hematopoietic tumors, leukemias and lymphomas, including Burkitt lymphoma. Myc is also known in the art as MYC, v-myc myelocytomatosis viral oncogene homolog (avian), transcription factor p64, bHLHe39, MRTL, avian myelocytomatosis viral oncogene homolog, v-myc avian myelocytomatosis viral oncogene homolog, myc proto-oncogene protein, class E basic helix-loop-helix protein 39, myc-related translation/localization regulatory factor, and proto-oncogene Myc, and BHLHE39.

As used herein "Atoh1" refers to atonal homolog 1 and family thereof. The Atoh1 belongs to the basic helix-loop-helix (BHLH) family of transcription factors. It activates E-box dependent transcription along with E47. The full-length Atoh1 appears, for example, in the NCBI protein database under accession no. NC_000004.12. See, also, US Publication Nos. US 20040237127 and US 20110251120.

As used herein, the term "green fluorescent protein" (GFP) refers to a protein originally isolated from the jellyfish *Aequorea victoria* that fluoresces green when exposed to blue light or a derivative of such a protein (e.g., a supercharged version of the protein). The amino acid sequence of wild type GFP is as follows: (SEQ ID NO: 1) MSKGEELFTG VVPILVELDG DVNGHKFSVS GEGEGDATYG KLTLKFICTT GKLPVPWPTL VTTFSYGVQC FSRYPDHMKQ HDFFKSAMPE GYVQERTIFF KDDGNYKTRA EVKFEGDTLV NRIELKGIDF KEDGNILGHK LEYNYNSHNV YIMADKQKNG IKVNFKIRHN IEDGSVQLAD HYQQNTPIGD GPVLLPDNHY LSTQSALSKD PNEKRDHMVL LEFVTAAGIT HGMDELYK.

Proteins that are at least 70%, at least 75%, at least 80%, at least 85%, at least 90%, at least 95%, at least 98%, or at least 99% homologous to SEQ ID NO: 1, are also considered to be green fluorescent proteins. In certain embodiments, the green fluorescent protein is supercharged. In certain embodiments, the green fluorescent protein is superpositively charged (e.g., +15 GFP, +25 GFP, and +36 GFP). In certain embodiments, the GFP may be modified to include a polyhistidine tag for ease in purification of the protein. In certain embodiments, the GFP may be fused with another protein or peptide (e.g., hemagglutinin 2 (HA2) peptide). In certain embodiments, the GFP may be further modified biologically or chemically (e.g., post-translational modifications, proteolysis, etc.).

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been modified or derivatized, such as by glycosylation, acetylation, phosphorylation, and the like.

As used herein, a "nucleic acid" or "nucleic acid sequence" or "cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

A "polynucleotide" means a single strand or parallel and anti-parallel strands of a nucleic acid. Thus, a polynucleotide may be either a single-stranded or a double-stranded nucleic acid.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

As used herein, the terms "nucleic acid sequence", "polynucleotide," and "gene" are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like.

The nucleic acid sequences may be "chimeric" that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

The term "target nucleic acid" refers to a nucleic acid (often derived from a biological sample), to which the oligonucleotide is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA) whose expression level it is desired to detect. The difference in usage will be apparent from context.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.*, 1997, 25(22), 4429-4443, Toulmé, J. J., *Nature Biotechnology* 19:17-18 (2001); Manoharan M., *Biochemica et Biophysica Acta* 1489:117-139(1999); Freier S. M., *Nucleic Acid Research*, 25:4429-4443 (1997), Uhlman, E., *Drug Discovery & Development*, 3: 203-213 (2000), Herdewin P., *Antisense & Nucleic Acid Drug Dev.*, 10:297-310 (2000)); 2'-O, 3'-C-linked [3.2.0] bicycloarabinonucleosides (see e.g. N. K Christiensen., et al, *J. Am. Chem. Soc.*, 120: 5458-5463 (1998). Such analogs include synthetic nucleosides designed to enhance binding properties, e.g., duplex or triplex stability, specificity, or the like.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

As defined herein, a "therapeutically effective" amount of a compound or agent (i.e., an effective dosage) means an amount sufficient to produce a therapeutically (e.g., clinically) desirable result, for example, induce cell cycle reentry and/or proliferation of the cells of the inner ear (e.g., a hair cell or a supporting cell). The cells are contacted with amounts of the active agent effective to induce cell cycle reentry and/or proliferation and/or transdifferentiation of supporting cells to hair cells. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

As defined herein, an "effective" amount of a compound or agent (i.e., an effective dosage) means an amount sufficient to produce a (e.g., clinically) desirable result.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. An agent can be assayed in accordance with the methods of the invention at any stage during clinical trials, during pre-trial testing, or following FDA-approval.

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

General Techniques

For further elaboration of general techniques useful in the practice of this invention, the practitioner can refer to standard textbooks and reviews in cell biology, tissue culture, embryology, and physiology.

With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in vitro (M. V. Wiles, *Meth. Enzymol.* 225:900, 1993); Properties and uses of Embryonic Stem Cells: Prospects for Application to Human Biology and Gene Therapy (P. D. Rathj en et al., *Reprod. Fertil. Dev.* 10:31, 1998).

General methods in molecular and cellular biochemistry can be found in such standard textbooks as Molecular Cloning: A Laboratory Manual, $3^{rd}$ Ed. (Sambrook et al., Harbor Laboratory Press 2001); Short Protocols in Molecular Biology, $4^{th}$ Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

The following description of the preferred embodiments is merely exemplary in nature and is in no way intended to limit the invention, its application or uses. Embodiments of the invention may be practiced without the theoretical aspects presented. Moreover, the theoretical aspects are presented with the understanding that Applicants do not seek to be bound by the theory presented.

Supercharged Proteins

Supercharged proteins can be produced by changing non-conserved amino acids on the surface of a protein to more polar or charged amino acid residues. The amino acid residues to be modified may be hydrophobic, hydrophilic, charged, or a combination thereof. Supercharged proteins can also be produced by the attachment of charged moieties to the protein in order to supercharge the protein. Supercharged proteins frequently are resistant to aggregation, have an increased ability to refold, resist improper folding, have improved solubility, and are generally more stable under a wide range of conditions, including denaturing conditions such as heat or the presence of a detergent.

Any protein may be modified using the inventive system to produce a supercharged protein. Natural as well as unnatural proteins (e.g., engineered proteins) may be modified. Example of proteins that may be modified include receptors, membrane bound proteins, transmembrane proteins, enzymes, transcription factors, extracellular proteins, therapeutic proteins, cytokines, messenger proteins, DNA-binding proteins, RNA-binding proteins, proteins involved in signal transduction, structural proteins, cytoplasmic proteins, nuclear proteins, hydrophobic proteins, hydrophilic proteins, etc. A protein to be modified may be derived from any species of plant, animal, and/or microorganism. In certain embodiments, the protein is a mammalian protein. In certain embodiments, the protein is a human protein. In certain embodiments, the protein is derived from an organism typically used in research. For example, the protein to be modified may be from a primate (e.g., ape, monkey), rodent (e.g., rabbit, hamster, gerbil), pig, dog, cat, fish (e.g., *Danio rerio*), nematode (e.g., *C. elegans*), yeast (e.g., *Saccharomyces cerevisiae*), or bacteria (e.g., *E. coli*). In certain embodiments, the protein is non-immunogenic. In certain embodiments, the protein is non-antigenic. In certain embodiments, the protein does not have inherent biological activity or has been modified to have no biological activity. In certain embodiments, the protein is chosen based on its targeting ability. In certain embodiments, the protein is green fluorescent protein.

Compositions and Treatments

Disclosed herein are methods of inducing proliferation or cell cycle reentry of inner ear cells, such as, for example, strial vascularis, hair cells and supporting cells. Methods of transdifferentiation of supporting cells, neurite growth, are also described. In general, the methods comprise increasing Myc, Notch or both Myc activity and Notch activity within the cell sufficient to induce proliferation or cell cycle reentry of the hair cells and/or supporting cells. Inhibition of Myc and/or Notch and/or the activation of Atoh1 induce the transdifferentiation of supporting cells to hair cells.

The compositions, embodied herein, activate Myc and Notch in inner ear cells, such as, hair cells and/or supporting cells which results in the induction of hair cell and/or supporting cell proliferation. In addition, compositions activating Atoh1 induces transdifferentiation of supporting cells to hair cells. The proliferation and the subsequent differentiation of the cell into hair and/or supporting cells can restore or improve hearing and/or vestibular function.

Activation and subsequent inactivation of Myc and Notch1 can lead to regeneration of cells within the strial vascularis that includes marginal cells, intermediate cells, basal cells and fibrocytes. Degeneration of strial vascularis causes hearing loss. Regeneration of any of the cell types could lead to hearing recovery, including neurite growth or other neural cells associated with hearing and hearing loss due to any cause. Hair cells are inner ear sensory cells, including inner hair cells, outer hair cells, and vestibular hair cells. Supporting cells include Deiters cells, Hensen cells, Pillar cells, inner phalangeal cells, inner border cells, Claudius cells, border cells, basal cells, interdental cells, inner sulcus, spiral limbus.

Disclosed herein are compositions for gene editing of cells of the inner ear. In particular, the targeted cells are the hair cells and supporting cells. The compositions, embodied herein, modulate various pathways and associated molecules which contribute to deafness or disorders thereof, in hair cells and supporting cells. Hair cells are inner ear sensory cells, including inner hair cells, outer hair cells, and vestibular hair cells. Supporting cells include Deiters cells, Hensen cells, Pillar cells, inner phalangeal cells, inner border cells, Claudius cells, border cells, basal cells, interdental cells, inner sulcus, spiral limbus.

Hearing loss affects a large portion of population yet no treatment is available beyond hearing aids and cochlear implant, both of which provide limited benefits. In the US alone, over 30 million people suffer from hearing loss. The major cause of hearing loss in humans is due to irreversible loss of the inner ear sensory cells, hair cells, which are responsible for detecting sounds and sensing balance. As the result, regeneration of hair cells has become a focus aiming at developing potential therapy for hearing loss. Further hearing loss can be caused by defective cell types in the inner ear such as strial vascularis and supporting cells, neurites, or any cell type associated with deafness or associated disorders thereof, whose regeneration could lead to restoration of hearing.

Accordingly, embodiments are directed to protein-mediated delivery systems to deliver the biological proteins directly to inner ear cell types with functional consequences. With these methods, the proteins delivered have specific functions, and the effect is transient. Further, delivery of native protein lessens any potential immune response. Such an approach would not only be valuable for inner ear delivery, but has far reaching effects on the delivery of proteins targeting different diseases, achieving specific effects in multiple organs and cell types.

For efficient protein delivery, proteins need to enter cells with sufficient amounts, and are released from endosomes within cells and reach the targets. Improvement in the endosome release could have drastic effects on the amount of protein to reach the target with enhanced biological effect. Antimicrobial or membrane destabilizing peptides, for example, Aurein, combination with s-GFP, can serve as an effective carrier to deliver functional proteins into mouse inner ear cell types with high efficiency.

High-efficiency delivery of functional proteins in the inner ear has tremendous advantage over conventional systems, including (1). It allows the delivery of unlimited combinations of proteins to mammalian inner ear without limitations on the size or localization of proteins delivered; (2). The effect will be specific; (3). The effect will be transient as delivered proteins will be degraded over time, which allows the modification of proteins (e.g., to reduce the response to degradation pathway) and controls the time length of function. The delivery system can be used to study protein functions, inner ear regeneration for hearing recovery, hearing protection, and gene editing to correct genetic deafness by genome-editing proteins.

In one embodiment, a chimeric molecule comprises at least one protein or peptide fused, complexed or linked to one or more anionic molecules, wherein the one or more anionic molecules comprise one or more anionic domains or bind to an anionic nucleic acid domain. In some embodiments, the chimeric molecule comprises an overall net negative charge. The anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof.

In another embodiment, the chimeric molecules are cationic, anionic or are neutrally charged. In another embodiment, the one or more proteins or peptides are cationic, anionic or are neutrally charged. The proteins or peptides comprise: antimicrobial or membrane destabilizing peptides, Myc protein or peptides, Myc modulators, Notch protein or peptides, Notch Intracellular domain (NICD)

proteins or peptides, Atonal Homolog 1 (Atoh1), Atoh1 modulators, transcription factors, transcription modulators, or combinations thereof.

In an embodiment, a chimeric molecule comprises: a supercharged protein, an antimicrobial or membrane destabilizing peptide, Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof.

In another embodiment, a chimeric molecule comprises at least one supercharged protein linked to at least one antimicrobial or membrane destabilizing peptide, and Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof.

In another embodiment, the chimeric molecule comprises a supercharged molecule connected to a membrane destabilization domain which in turn is connected to one or more Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof.

In another embodiment, the chimeric molecule comprises one or more membrane destabilization domains connected to one or more Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof.

In another embodiment, the chimeric molecule comprises a membrane destabilization domain connected to a supercharged molecule which in turn is connected to one or more Myc proteins or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof.

In another embodiment, the chimeric molecule comprises a membrane destabilization domain connected to one or more Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof, which are connected to a supercharged molecule.

One of ordinary skill in the art would understand that there are a multitude of configurations which can be obtained. Accordingly, if the letter "S" represents the supercharged domain, the letter "M" represents the antimicrobial or membrane destabilizing domain, and the letter "X" represents the therapeutic molecules such as, Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof. The molecular structure of the molecule can be S-M-X, or M-X-X, or S-M-M-X, or S-S-M-M-X, etc. In those cases where there are two or more molecules that comprise a domain (e.g. a membrane destabilization domain), these domains can comprise different molecules or they can be the same molecule.

For efficient protein delivery, proteins need to enter cells with sufficient amount, and are released from endosomes within cells and reach the targets. Improvement in the endosome release would have drastic effects on the amount of protein to reach the target with enhanced biological effect. Aurein, an antimicrobial peptide in combination with s-GFP, can serve as an effective carrier to deliver functional proteins into mouse inner ear cell types with high efficiency. Accordingly, in embodiments, the compositions comprise a supercharged protein linked to antimicrobial or membrane destabilizing peptides, for example, aurein, mutants or variants thereof (e.g. (GLFDIIKKIAESF; SEQ ID NO: 2)). Membrane destabilization peptides are known in the art. See, for example, Fernandez, D. I. et al., *Biochim. Biophys. Acta*, 2009 August; 1788(8):1630-8.

Examples of aurein mutants are shown in Table 1.

| Label | Sequence |
| --- | --- |
| Aurein 1.2 | GLFDIIKKIAESF (SEQ ID NO: 2) |
| G1A | ALFDIIKKIAESF (SEQ ID NO: 3) |
| L2A | GAFDIIKKIAESF (SEQ ID NO: 4) |
| F3A | GLADIIKKIAESF (SEQ ID NO: 5) |
| D4A | GLFAIIKKIAESF (SEQ ID NO: 6) |
| I5A | GLFDAIKKIAESF (SEQ ID NO: 7) |
| I6A | GLFDIAKKIAESF (SEQ ID NO: 8) |
| K7A | GLFDIIAKIAESF (SEQ ID NO: 9) |
| K8A | GLFDIIKAIAESF (SEQ ID NO: 10) |
| I9A | GLFDIIKKAAESF (SEQ ID NO: 11) |
| E11A | GLFDIIKKIAASF (SEQ ID NO: 12) |
| S12A | GLFDIIKKIAEAF (SEQ ID NO: 13) |
| F13A | GLFDIIKKIAESA (SEQ ID NO: 14) |
| K7H | GLFDIIHKIAESF (SEQ ID NO: 15) |
| K8H | GLFDIIKHIAESF (SEQ ID NO: 16) |
| E11H | GLFDIIKKIAHSF (SEQ ID NO: 17) |
| K7R | GLFDIIRKIAESF (SEQ ID NO: 18) |
| K8R | GLFDIIKRIAESF (SEQ ID NO: 19) |
| E11R | GLFDIIKKIARSF (SEQ ID NO: 20) |
| E11D | GLFDIIKKIADSF (SEQ ID NO: 21) |

In an embodiment, a membrane destabilizing domain comprises one or more of: antimicrobial or membrane destabilizing proteins or peptides, polynucleotides, oligonucleotides, bacterial or viral (e.g. reovirus outer capsid protein or peptide, μl; papilloma virus capsid protein or peptide L2; etc.), antibacterial molecules, antimicrobial peptides, microtubules, lipids, synthetic or natural molecules, or combinations thereof. Antimicrobial peptides (AMPS) are a class of membrane-active peptides that penetrate microbial membranes to provide defense against bacteria, fungi, and viruses, often with high selectivity (Zasloff, M. *Nature* 2002, 415, 389). Table 2 shows non-limiting examples of antimicrobial peptides.

TABLE 2

List of peptides from the Antimicrobial Peptide Database (APD)

| APD number | Sequence |
|---|---|
| AP00408 | FLFPLITSFLSKVL (SEQ ID NO: 22) |
| AP00405-11 | FISAIASMLGKFL (SEQ ID NO: 23) |
| AP00327 | GWFDVVKHIASAV (SEQ ID NO: 24) |
| AP01434 | FFGSVLKLIPKIL (SEQ ID NO: 25) |
| AP00013 | GLFDIIKKIAESF (SEQ ID NO: 26) |
| AP00025 | HGVSGHGQHGVHG (SEQ ID NO: 27) |
| AP00094 | FLPLIGRVLSGIL (SEQ ID NO: 28) |
| AP00012 | GLFDIIKKIAESI (SEQ ID NO: 29) |
| AP00014 | GLLDIVKKVVGAFGSL (SEQ ID NO: 30) |
| AP00015 | GLFDIVKKVVGALGSL (SEQ ID NO: 31) |
| AP00016 | GLFDIVKKVVGAIGSL (SEQ ID NO: 32) |
| AP00017 | GLFDIVKKVVGTLAGL (SEQ ID NO: 33) |
| AP00018 | GLFDIVKKVVGAFGSL (SEQ ID NO: 34) |
| AP00019 | GLFDIAKKVIGVIGSL (SEQ ID NO: 35) |
| AP00020 | GLFDIVKKIAGHIAGSI (SEQ ID NO: 36) |
| AP00021 | GLFDIVKKIAGHIASSI (SEQ ID NO: 37) |
| AP00022 | GLFDIVKKIAGHIVSSI (SEQ ID NO: 38) |
| AP00101 | FVQWFSKFLGRIL (SEQ ID NO: 39) |
| AP00351 | GLFDVIKKVASVIGGL (SEQ ID NO: 40) |
| AP00352 | GLFDIIKKVASVVGGL (SEQ ID NO: 41) |
| AP00353 | GLFDIIKKVASVIGGL (SEQ ID NO: 42) |
| AP00567 | VWPLGLVICKALKIC (SEQ ID NO: 43) |
| AP00597 | NFLGTLVNLAKKIL (SEQ ID NO: 44) |
| AP00818 | FLPLIGKILGTIL (SEQ ID NO: 45) |
| AP00866 | FLPIIAKVLSGLL (SEQ ID NO: 46) |
| AP00870 | FLPIVGKLLSGLL (SEQ ID NO: 47) |
| AP00875 | FLSSIGKILGNLL (SEQ ID NO: 48) |
| AP00898 | FLSGIVGMLGKLF (SEQ ID NO: 49) |
| AP01211 | TPFKLSLHL (SEQ ID NO: 50) |
| AP01249 | GILDAIKAIAKAAG (SEQ ID NO: 51) |
| AP00013-G | LFDIIKKIAESF (SEQ ID NO: 52) |
| AP00013-2x | LFDIIKKIAESGFLFDIIKKIAESF (SEQ ID NO: 53) |
| AP00722-75 | GLLNGLALRLGKRALKKIIKRLCR (SEQ ID NO: 54) |
| His13 | GHHHHHHHHHHHHH (SEQ ID NO: 55) |
| AP00512 | FKCRRWQWRM (SEQ ID NO: 56) |
| AP00553 | KTCENLADTY (SEQ ID NO: 57) |

In an embodiment, the chimeric molecules embodied herein are encapsulated in a liposome. In one embodiment, the liposome is a cationic liposome.

In an embodiment, a method of regenerating inner ear cells in vitro or in vivo comprises contacting a cell in vitro or administering to an inner ear of a patient in need of such treatment, a composition comprising an effective amount of a chimeric molecule comprising an antimicrobial or membrane destabilizing domain connected to one or more Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof, which modulate activity of Myc, Notch, Atonal Homolog 1 (Atoh1), Notch Intracellular domain (NICD) proteins, Notch Intracellular domain (NICD) peptides, or combinations thereof within a cell, to induce proliferation or cell cycle re-entry in inner ear cells comprising, strial vascularis, hair cells, or supporting cells of the inner ear. The method may also include the step of inhibiting Myc and/or Notch activity after proliferation of the inner ear cells, such as, strial vascularis, hair or supporting cell to induce differentiation or transdifferentiation of the cell and/or at least one of its daughter cells into a hair cell. The method may also further include the step of activating Atoh1 to induce transdifferentiation of the supporting cells to hair cells. The Myc activity in the hair and/or supporting cells is increased by administering an effective amount of Myc protein, Myc peptides or Myc activators linked to supercharged proteins, such as, for example, green fluorescent proteins (s-GFP) or variants thereof. The Notch activity is increased by administering an effective amount of Notch protein, Notch peptides, Notch activators, Notch Intracellular domain (NICD) proteins, Notch Intracellular domain (NICD) peptides, or combinations thereof, linked to GFP or variants thereof. Inhibition of Myc and/or Notch can be accomplished through administration of inhibitors or once the activator has degraded over time. Activation of Atoh1 is accomplished by the delivery of Atoh1 proteins, Atoh1 peptides, Atoh1 activators, or combinations thereof, linked to s-GFP or variants thereof.

In an embodiment, a method of regenerating inner ear cells in vitro or in vivo comprises contacting a cell in vitro or administering to an inner ear of a patient in need of such treatment, a composition comprising an effective amount of a chimeric molecule comprising an antimicrobial or membrane destabilizing domain connected to one or more Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof, which modulate activity of Myc, Notch, Atonal Homolog 1 (Atoh1), Notch Intracellular domain (NICD) proteins, Notch Intracellular domain (NICD) peptides, or combinations thereof within a cell, to induce proliferation or cell cycle re-entry in inner ear cells comprising, strial vascularis, hair cells, or supporting cells of the inner ear.

In embodiments, the chimeric molecule further comprises a supercharged protein, such as, for example, a fluorescent protein or variants thereof. In one embodiment, the supercharged protein is green fluorescent protein (s-GFP), or variants thereof. In one embodiment, the supercharged protein comprises green fluorescent protein (s-GFP) linked to one or more proteins or peptides, or modified variants thereof, comprising: Myc protein or peptides, Myc modulators, Notch protein or peptides, Notch Intracellular domain (NICD) proteins or peptides, Protein Atonal Homolog 1 (Atoh1), transcription factors, transcription modulators, or combinations thereof. In some embodiments these supercharged proteins further comprise antimicrobial or membrane destabilizing peptides, for example, aurein, or variants thereof linked to the GFP or variants thereof.

When the chimeric molecule comprising Myc and/or Notch activators are administered to a patient, or, contact a cell, the activation of Myc and/or Notch activity induces proliferation of the inner ear cells comprising, strial vascularis, hair cells, or supporting cells of the inner ear. Furthermore, inhibition of Myc activity, Notch activity, NICD activity or combinations thereof, in supporting cells induces transdifferentiation of the supporting cells into functional hair cells. Once the Myc activity and/or Notch activity is inhibited or reaches a pre-determined level of activity due to the normal degradation of the protein, the activity of which can be measured by any one or more conventional assays, a composition comprising activators of Atoh1 is administered to the inner ear, wherein activation of Atoh1 induces transdifferentiation of the supporting cells into functional hair cells.

Myc activity is increased by administering an effective amount of Myc protein, Myc peptides or Myc activators linked to GFP or variants thereof. Notch activity is increased by administering an effective amount of Notch protein, Notch peptides, Notch activators, Notch Intracellular domain (NICD) proteins, Notch Intracellular domain (NICD) peptides, or combinations thereof, linked to GFP or variants thereof.

In another embodiment, a method of regenerating inner ear cells in vitro or in vivo comprises contacting a cell in vitro or administering to an inner ear of patient in need of such treatment, a composition comprising an effective amount of a chimeric molecule comprising one or more proteins, peptides or variants thereof, which activate Myc, Notch, Atonal Homolog 1 (Atoh1), Notch Intracellular domain (NICD), or combinations thereof within a cell, to induce proliferation or cell cycle re-entry in hair and supporting cells of the inner ear. The method further comprises contacting the supporting cells with a composition comprising Atoh1 modulators or variants thereof, wherein the Atoh1 modulates induce transdifferentiation of the supporting cells into functional hair cells. In embodiments, the Atoh1 composition comprises a supercharged protein linked to one or more polypeptides or variants thereof comprising: antimicrobial or membrane destabilizing peptides, aurein, Atoh1 proteins, Atoh1 peptides, activators of Atoh1, variants or combinations thereof. In other embodiments, the Atoh1 composition comprises a vector encoding for Atoh1 proteins, Atoh1 peptides, Atoh1 activators, variants or combinations thereof. In another embodiment, the composition comprises an effective amount of a chimeric protein comprising a supercharged protein or variants thereof linked to an antimicrobial or membrane destabilizing peptide, and the antimicrobial or membrane destabilizing peptide being linked to one or more Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof.

In another embodiment, a method of inducing proliferation and transdifferentiation of inner ear cells, in vivo or in vitro, comprises contacting a hair cell and/or a supporting cell with a composition which increases activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in hair and supporting cells of the inner ear; administering inhibitors to inhibit Notch and Myc activity; and, administering a composition which activates Atoh1 in the supporting cells, inducing the transdifferentiation of the supporting cells to hair cells. In another embodiment, the composition comprises an effective amount of a chimeric protein comprising a supercharged protein or variants thereof linked to an antimicrobial or membrane destabilizing peptide, and the antimicrobial or membrane destabilizing peptide being linked to one or more Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof.

In another embodiment, a method of preventing or treating deafness or disorders thereof, in a patient in need of such treatment comprises contacting a hair cell and/or a supporting cell with a composition which increases activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in inner ear cells comprising, strial vascularis, hair cells, or supporting cells of the inner ear; administering inhibitors to inhibit Notch and Myc activity; and, administering an activator of Atoh1, wherein the Atoh1 activator induces the transdifferentiation of the supporting cells to hair cells. In another embodiment, the composition comprises an effective amount of a chimeric protein comprising a supercharged protein or variants thereof linked to an antimicrobial or membrane destabilizing peptide, and the antimicrobial or membrane destabilizing peptide being linked to one or more Myc protein or peptides, Myc modulators, Notch protein or peptides, Notch Intracellular domain (NICD) proteins or peptides, Atonal Homolog 1 (Atoh1), Atoh1 modulators, transcription factors, transcription modulators, or combinations thereof.

In another embodiment, a method of inducing proliferation and transdifferentiation of inner ear cells, in vivo or in vitro, comprises contacting a hair cell and/or a supporting cell with a composition which increases activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in inner ear cells comprising, strial vascularis, hair cells, or supporting cells of the inner ear; wherein after Notch and/or Myc activity is decreased or inhibited, administering an activator of Atoh1, to induce the transdifferentiation of the supporting cells to hair cells.

In another embodiment, a method of preventing or treating deafness or disorders thereof, in a patient in need of such treatment comprises contacting a hair cell and/or a supporting cell with a composition which increases activity of Myc proteins or peptides, Notch proteins or peptides, Notch Intracellular domain (NICD) proteins, Notch Intracellular domain (NICD) peptides, variants or combinations thereof within a cell, to induce proliferation or cell cycle re-entry in inner ear cells comprising, strial vascularis, hair cells, or supporting cells of the inner ear; wherein after Notch and/or Myc activity is decreased or inhibited, administering an activator of Atoh1, to induce the transdifferentiation of the supporting cells to hair cells.

In another embodiment, a method of delivering a therapeutic molecule to cells of an inner ear of a patient, comprising: administering to the inner ear of a patient a chimeric molecule comprising at least one protein or peptide fused, complexed or linked to one or more anionic molecules. The cells or the inner ear comprise hair cells, supporting cells, or combinations thereof. The chimeric molecule comprises one or more gene editing agents, transcriptional modulators, translational modulators, post-translational modulators, and/or modulators that regulate protein expression, function, activity or combinations thereof. In some embodiments, the gene editing agents comprise: transcriptional activators, transcriptional repressors, recombinases, nucleases, DNA-binding proteins or nucleic acids, or combinations thereof. The anionic molecules comprise: oligonucleotides, polynucleotides, proteins, peptides, peptide nucleic acids (PNA), synthetic molecules or combinations thereof. The oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof. The chimeric molecule further comprises a supercharged protein or variants thereof, such as, for example, a fluorescent protein, or variants thereof. In some embodiments the chimeric molecule comprises antimicrobial or membrane destabilizing peptides, for example, aurein, or variants thereof. In some embodiments, the chimeric molecule is encapsulated in a cationic lipid formulation.

In an embodiment, a method of inducing transdifferentiation of inner ear cells comprises contacting an inner ear cell in vitro or in vivo with a composition which transiently increases activity of Myc proteins or peptides, Notch proteins or peptides, Notch Intracellular domain (NICD) proteins, Notch Intracellular domain (NICD) peptides, variants or combinations thereof within a cell, to induce transdifferentiation of supporting cells of the inner ear without proliferation; wherein after Notch activity is decreased or inhibited by a Notch inhibitor, optionally, administering an activator of Atoh1, to induce the transdifferentiation of the supporting cells to hair cells.

In another embodiment, a method of regenerating inner ear cells comprises inducing proliferation or cell cycle reentry of inner ear cells in vitro or in vivo, the method comprising contacting a cell in vitro or administering to an inner ear of a patient in need of such treatment, a composition comprising an effective amount of a supercharged protein comprising one or more proteins, peptides or variants thereof, which modulate activity of Myc, Notch, Atonal Homolog 1 (Atoh1), Notch Intracellular domain (NICD) proteins, Notch Intracellular domain (NICD) peptides, or combinations thereof within a cell, to induce proliferation or cell cycle re-entry in inner ear cells.

In another embodiment, a method protecting and/or treating hearing loss in a patient in need of such treatment, comprising: contacting a cell in vitro or administering to an inner ear of a patient in need of such treatment, a composition comprising an effective amount of a supercharged protein comprising one or more proteins, peptides or variants thereof, which modulate activity of Myc, Notch, Atonal Homolog 1 (Atoh1), Notch Intracellular domain (NICD) proteins, Notch Intracellular domain (NICD) peptides, or combinations thereof within a cell, to induce neurite growth, proliferation or cell cycle re-entry of inner ear cells, proliferation of hair cells, proliferation of supporting cells, and/or transdifferentiation of supporting cells.

As discussed above, after Myc activity, Notch activity, or both Myc and Notch activities, as appropriate, is or are increased, Myc and/or Notch activity may be inhibited according to methods known in the art and/or described herein to cause proliferating supporting cells to transdifferentiate into hair cells. Alternatively, or in addition, after Myc activity, Notch activity, or both Myc and Notch activity is or are increased, as appropriate, Atoh1 activity can be increased to cause proliferating supporting cells to transdifferentiate into hair cells. Atoh1 activity can be increased according to the compositions embodied herein, or, in conjunction with or alternatively with the use of one or more conventional compounds or methods of increasing Atoh1 activity (including use of Atoh1 agonists) known in the art (see, for example, U.S. Pat. No. 8,188,131; U.S. Patent Publication No. 20110305674; U.S. Patent Publication No. 20090232780; Kwan et al. (2009) Int'l Symposium on Olfaction and Taste: *Ann. N.Y. Acad. Sci.* 170:28-33; Daudet et al. (2009) *Dev. Bio.* 326:86-100; Takebayashi et al. (2007) *Dev. Bio.* 307: 165-178; and Ahmed et al. (2012) *Dev. Cell* 22(2):377-390.)

The process described herein can occur in vivo or ex vivo. In one embodiment, Notch activity is decreased in a cell that originated from a supporting cell to cause the supporting cell to transdifferentiate into a hair cell. In another embodiment, Atoh1 activity is increased in a cell that originated from a supporting cell to cause the supporting cell to transdifferentiate into a hair cell. In certain embodiments, after Myc and Notch induce proliferation within a hair cell or supporting cell, Myc activity is decreased to induce differentiation of at least one of the cell and the daughter cell to produce a differentiated cochlear or utricular hair cell. Activation of Myc/NICD increases the response of supporting cells to Atoh1 to transdifferentiate to hair cells, without proliferation or cell cycle re-entry. After Myc/NICD activation, both dividing and non-dividing supporting cells can transdifferentiate to hair cells in response to Atoh1 overexpression or Notch inhibition by gamma-secretase inhibitor.

Also disclosed is a method for reducing the loss of, maintaining, or promoting hearing in a subject. The method comprises increasing Myc activity, Notch activity, or both Myc activity and Notch activity, as appropriate, within a hair cell and/or a supporting cell of the inner ear thereby to induce cell proliferation to produce daughter cells, and, after cell proliferation, decreasing Myc and/or Notch activity, and administering a composition embodied herein, comprising Atoh1 activators to induce daughter cells of hair cell origin to differentiate into hair cells or permitting daughter cells of supporting cell origin to transdifferentiate into hair cells thereby to reduce the loss of, maintain or promote hearing in the subject. The daughter cells of supporting cell origin can be induced to transdifferentiate into hair cells by activating Atoh1 activity, for example, by gene expression, by administration of an effective amount of Atoh1 or an Atoh1 agonist. The steps can be performed in vivo (for example, in the inner ear of a mammal, in particular in the cochlea), or ex vivo, wherein the resulting cells are cultured and/or introduced into the inner ear of the subject.

Also disclosed is a method for reducing the loss of, maintaining, or promoting vestibular function in a subject. The method comprises increasing Myc activity, Notch activity, or both Myc activity and Notch activity, as appropriate, within a hair cell and/or a supporting cell of the inner ear thereby to induce cell proliferation to produce daughter cells, and, after cell proliferation, decreasing Myc and/or Notch activity, and permitting daughter cells of hair cell origin to differentiate into hair cells or permitting daughter cells of supporting cell origin to transdifferentiate into hair cells thereby to reduce the loss of, maintain or promote vestibular function in the subject. The daughter cells of supporting cell origin can be induced to transdifferentiate into hair cells by activating Atoh1 activity, for example, by gene expression, by administration of an effective amount of Atoh1 or an Atoh1 agonist. The steps can be performed in vivo (for example, in the inner ear of a mammal, in particular in the utricle), or ex vivo, wherein the resulting cells are cultured and/or introduced into the inner ear of the subject.

The methods and compositions described herein can be used for treating subjects who have, or who are at risk for developing, an auditory disorder resulting from a loss of auditory hair cells, e.g., sensorineural hair cell loss. Patients having an auditory disorder can be identified using standard hearing tests known in the art. The method can comprise (a) increasing Myc activity, Notch activity, or both Myc activity and Notch activity, as appropriate, within the hair cell of the subject thereby to induce cell proliferation to produce a daughter cell, and (b) after cell proliferation, decreasing Notch activity to induce differentiation of at least one of the cell and the daughter cell to produce a differentiated cochlear or utricular hair cell. This can be accomplished by administering an agent or agents to the subject to modulate Myc and Notch activity. Alternatively, the process can occur in cells (e.g. cochlear and/or utricular cells) ex vivo, after which the resulting cells are transplanted into the inner ear of the subject. In certain embodiments, the methods and compositions described herein can be used to promote growth of neurites from the ganglion neurons of the inner ear. For example, the regeneration of hair cells may promote the growth of new neurites from ganglion neurons and formation of new synapses with the regenerated hair cells to transmit sound and balance signals from the hair cells to the brain.

In certain embodiments, the methods and compositions described herein can be used to promote growth of neurites from the ganglion neurons of the inner ear. For example, the regeneration of hair cells may promote the growth of new neurites from ganglion neurons and formation of new synapses with the regenerated hair cells to transmit sound and balance signals from the hair cells to the brain. In some embodiments, the methods and compositions described herein can be used to reestablish proper synaptic connections between hair cells and auditory neurons to treat, for example, auditory neuropathy.

Subjects with sensorineural hair cell loss experience the degeneration of cochlea hair cells, which frequently results in the loss of spiral ganglion neurons in regions of hair cell loss. Such subjects may also experience loss of supporting cells in the organ of Corti, and degeneration of the limbus, spiral ligament, and stria vascularis in the temporal bone material.

In certain embodiments, the present invention can be used to treat hair cell loss and any disorder that arises as a consequence of cell loss in the ear, such as hearing impairments, deafness, vestibular disorders, tinnitus (see, Kaltenbach et al. (2002) *J. Neurophysiol.* 88(2):699-714s), and hyperacusis (Kujawa et al. (2009) *J. Neurosci.* 29(45): 14077-14085), for example, by promoting differentiation (e.g., complete or partial differentiation) of one or more cells into one or more cells capable of functioning as sensory cells of the ear, e.g., hair cells.

In certain embodiments, the subject can have sensorineural hearing loss, which results from damage or malfunction of the sensory part (the cochlea) or non-sensory part (the limbus, spiral ligament and stria vascularis) or the neural part (the auditory nerve) of the ear, or conductive hearing loss, which is caused by blockage or damage in the outer and/or middle ear. Alternatively or in addition, the subject can have mixed hearing loss caused by a problem in both the conductive pathway (in the outer or middle ear) and in the nerve pathway (the inner ear). An example of a mixed hearing loss is a conductive loss due to a middle-ear infection combined with a sensorineural loss due to damage associated with aging.

In certain embodiments, the subject may be deaf or have a hearing loss for any reason, or as a result of any type of event. For example, a subject may be deaf because of a genetic or congenital defect; for example, a human subject can have been deaf since birth, or can be deaf or hard-of-hearing as a result of a gradual loss of hearing due to a genetic or congenital defect. In another example, a human subject can be deaf or hard-of-hearing as a result of a traumatic event, such as a physical trauma to a structure of the ear, or a sudden loud noise, or a prolonged exposure to loud noises. For example, prolonged exposures to concerts, airport runways, and construction areas can cause inner ear damage and subsequent hearing loss.

In certain embodiments, a subject can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants.

In certain embodiments, a subject can have a hearing disorder that results from aging. Alternatively or in addition, the subject can have tinnitus (characterized by ringing in the ears) or hyperacusis (heightened sensitivity to sound).

In addition, the methods and compositions described herein can be used to treat a subject having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision).

Alternatively or in addition, the methods and compositions described herein can be used prophylactically, such as to prevent, reduce or delay progression of hearing loss, deafness, or other auditory disorders associated with loss of inner ear function. For example, a composition containing one or more of the agents can be administered with (e.g., before, after or concurrently with) a second composition, such as an active agent that may affect hearing loss. Such ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as, quinine and chloroquine. For example, a human undergoing chemotherapy can be treated using the compounds and methods described herein. The chemotherapeutic agent cisplatin, for example, is known to cause hearing loss. Therefore, a composition containing one or more agents that increase the activity of Myc and Notch can be administered with cisplatin therapy (e.g., before, after or concurrently with) to prevent or lessen the severity of the cisplatin side effect. Such a composition can be administered before, after and/or simultaneously with the second therapeutic agent. The two agents may be administered by different routes of administration.

In certain embodiments, the methods and compositions described herein can be used to increase the levels (e.g., protein levels) and/or activity (e.g., biological activity) of Myc and Notch in cells (e.g., inner ear cells). Exemplary methods and compositions include, but are not limited to methods and compositions for increasing Myc or Notch expression (e.g., transcription and/or translation) or levels (e.g., concentration) in cells. It is contemplated that such modulation can be achieved in hair cells and/or supporting cells in vivo and ex vivo.

Methods and Compositions for Increasing Myc and Notch and Atoh1 Activity:

(i) Myc, Notch, or Atoh1 Polypeptides: It is contemplated that Myc, Notch, and Atoh1 proteins, including full length proteins, biologically active fragments, and homologs of Myc and Notch can be introduced into target cells using techniques known in the art.

Exemplary Myc polypeptides include, for example, NP_002458.2, as referenced in the NCBI protein database. Exemplary Notch polypeptides include, for example, NP_060087.3, as referenced in the NCBI protein database.

Exemplary Atoh1 polypeptides include, for example, NP_005163.1, as referenced in the NCBI protein database.

In certain embodiments, nucleic acid sequences encoding Myc, Notch, and Atoh1 family members may be used in accordance with the methods described herein. Exemplary Myc family members include N-myc, referenced in the NCBI protein database as NP_005369.2. Exemplary Notch family members include Notch2, referenced in the NCBI protein database as NP_077719.2; Notch3, referenced in the NCBI protein database as NP_000426.2; and Notch4, referenced in the NCBI protein database as NP_004548.3. Exemplary Atoh1 family members include Atoh7, referenced in the NCBI protein database as NP_660161.1.

In certain embodiments, a protein sequence of the invention may comprise a consensus protein sequence or a nucleotide sequence encoding a consensus protein sequence. Consensus protein sequences of Myc, Notch intracellular domain, and Atoh1 of the invention are set forth below. The Myc, Notch, or Atoh1 polypeptides can be used in combination with compositions to enhance uptake of the polypeptides into biological cells. In certain embodiments, the Atoh1, Myc, or Notch polypeptides can be mutated to include amino acid sequences that enhance uptake of the polypeptides into a biological cell. In certain embodiments, Atoh1, Myc, or Notch polypeptides can be altered or mutated to increase the stability and/or activity of the polypeptide (e.g., Myc, Notch or Atoh1 point mutants). In certain embodiments, Myc, Notch or Atoh1 polypeptides can be altered to increase nuclear translocation of the polypeptide. In certain embodiments, altered Myc, Notch or Atoh1 polypeptides or biologically active fragments of Myc, Notch, or Atoh1 retain at least 50%, 60%, 70%, 80%, 90%, or 95% of the biological activity of full length, wild type respective c-myc, Notch or Atoh1 protein in the species that is the same species as the subject that is or will be treated with the methods and compositions described herein.

In certain embodiments, Myc polypeptides sequences can be 50%, 60%, 70%, 80%, 85%, 90%, 95%, 98%, 99%, or 100% identical to NP_002458.2. In certain embodiments, Notch polypeptides sequences are 50%, 60%, 70%, 80%, 85%, 90%, 95%, 98%, 99%, or 100% identical to NP_060087.3. In certain embodiments, Atoh1 polypeptides sequences can be 50%, 60%, 70%, 80%, 85%, 90%, 95%, 98%, 99%, or 100% identical to NP_005163.1. In certain embodiments, agents encoded by modified Atoh1, Myc, NICD, or Notch nucleic acid sequences and Atoh1, Myc, or Notch polypeptide sequences possess at least a portion of the activity (e.g., biological activity) of the molecules encoded by the corresponding, e.g., unmodified, full-length Atoh1, Myc, or Notch nucleic acid sequences and Atoh1, Myc, or Notch polypeptide sequences. For example, molecules encoded by modified Atoh1, Myc, or Notch nucleic acid sequences and modified Atoh1, Myc, or Notch polypeptides retain 50%, 60%, 70%, 80%, 85%, 90%, 95%, 98%, 99%, or 100% of the activity (e.g., biological activity) of the molecules encoded by the corresponding, e.g., unmodified, respective Atoh1, Myc, or Notch nucleic acid sequences and/or full length Atoh1, Myc, or Notch polypeptide sequences.

In certain embodiments, the Myc and Notch proteins of the invention can be administered to cells as a single protein containing both Myc and Notch (or active domains thereof), preferably separated by a cleavable linker. Examples of cleavable linkers are known in the art (see, e.g., U.S. Pat. Nos. 5,258,498 and 6,083,486.)

Myc, Notch or Atoh1 levels (e.g., protein levels) and/or activity (e.g., biological activity) in target cells and/or in the nucleus of target cells can be assessed using standard methods such as Western Blotting, in situ hybridization, reverse transcriptase polymerase chain reaction, immunocytochemistry, viral titer detection, and genetic reporter assays. Increases in Myc, Notch or Atoh1 levels (e.g., protein levels) and/or activity (e.g., biological activity) in target cells and/or in the nucleus of target cells can be assessed by comparing Myc, Notch or Atoh1 levels and/or activity in a first cell sample or a standard with Myc, Notch or Atoh1 levels and/or activity in a second cell sample, e.g., contacting the cell sample with an agent contemplated to increase Myc, Notch or Atoh1 levels and/or activity.

Sequence identity may be determined in various ways that are within the skill in the art, e.g., using publicly available computer software such as BLAST, BLAST-2, ALIGN or Megalign (DNASTAR) software, which are used to perform sequence alignments and then calculate sequence identity. Exemplary software programs available from the National Center for Biotechnology Information (NCBI) on the website ncbi.nlm.nih.gov include blastp, blastn, blastx, tblastn and tblastx. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are used at the default settings. The default scoring matrix used by blastp, blastx, tblastn, and tblastx is the BLOSUM62 matrix (Henikoff et al, (1992) *Proc. Natl. Acad. Sci. USA* 89: 10915-10919). In one approach, the percent identity can be determined using the default parameters of blastp, version 2.2.26 available from the NCBI.

(ii) DNA Encoding Atoh1, Myc, or Notch: Atoh1, Myc, or Notch can be expressed in target cells using one or more expression constructs known in the art. Such expression constructs include, but are not limited to, naked DNA, viral and non-viral expression vectors. Exemplary Myc nucleic acid sequences that may be expressed in target cells include, for example, NM_002467.4, as referenced in the NCBI gene database. Exemplary Notch nucleic acid sequences that may be expressed include, for example, NM_017617.3, as referenced in the NCBI gene database. Exemplary Atoh1 nucleic acid sequences that may be expressed in target cells include, for example, NM_005172.1, as referenced in the NCBI gene database.

In certain embodiments, Myc, Notch, and Atoh1 family members may be used. Exemplary Myc family members include N-myc, referenced in the NCBI gene database as NM_005378.4. Exemplary Notch family members include Notch2, referenced in the NCBI gene database as NM_024408.3; Notch3, referenced in the NCBI gene database as NM_000435.2; and Notch4, referenced in the NCBI gene database as NM_004557.3. Exemplary Atoh1 family members include Atoh7, referenced in the NCBI gene database as NM_145178.3.

In certain embodiments, DNA encoding Myc, Notch or Atoh1 can be an unmodified wild type sequence. Alternatively, DNA encoding Myc, Notch or Atoh1 can be modified using standard techniques. For example, DNA encoding Myc, Notch or Atoh1 can be modified or mutated, e.g., to increase the stability of the DNA or resulting polypeptide. Polypeptides resulting from such altered DNAs should retain the biological activity of wild type Myc, Notch or Atoh1. In certain embodiments, DNA encoding Atoh1, Myc, or Notch can be altered to increase nuclear translocation of the resulting polypeptide. In certain embodiments, DNA encoding Myc, Notch or Atoh1 can be modified using standard molecular biological techniques to include an additional DNA sequence that can encode one or more of, e.g., detectable polypeptides, signal peptides, and protease cleavage sites.

In certain embodiments, Myc nucleic acid sequences can be 50%, 60%, 70%, 80%, 85%, 90%, 95%, 98%, 99%, or 100% identical to NM_002467.4. In certain embodiments, Notch nucleic acid sequences are 50%, 60%, 70%, 80%, 85%, 90%, 95%, 98%, 99%, or 100% identical to NM_017617.3. In certain embodiments, Atoh1 nucleic acid sequences are 50%, 60%, 70%, 80%, 85%, 90%, 95%, 98%, 99%, or 100% identical to NM_005172.1.

(iii) Myc, Notch or Atoh1 Pathway Modulators: In certain embodiments, Myc or Notch levels (e.g., protein levels) and/or activity (e.g., biological activity) can be increased or decreased using compounds or compositions that target Myc or Notch, or one or more components of the Myc or Notch pathway. Accordingly, in some embodiments, inhibiting Notch and activating Atoh1 comprises suppression of any one or more Notch1 targets, such as Hes5 and Hes1, both of which act as antagonists to Atoh1. Such suppression can be achieved by any conventional means, including, for example, anti-sense oligonucleotides against Hes1 and Hes5, or by delivering proteins that suppress Hes function. In some embodiments, any one or more molecules associated with the pathways of Myc, Notch, Atoh1 are targeted. Similarly, Atoh1 levels (e.g., protein levels) and/or activity (e.g., biological activity) can be increased using compounds that target Atoh1 or one or more components of the Atoh1 pathway.

Exemplary Myc activators include microRNAs that target FBXW-7 (Ishikawa Y et al, Oncogene 2012 Jun. 4; doi: 10.1038/onc.2012.213) and activators that increase Myc expression levels or activity such as nordihydroguaiaretic acid (NDGA) (Park S et al. (2004) *J. Cell. Biochem.* 91(5):973-86), CD19 (Chung et al., (2012) *J. Clin. Invest.* 122(6):2257-2266, cohesin (Ewan et al, (2012) PLoS ONE 7(1 1): e 9160), bryostatin 1 (Hu et al. (1993) *Leuk. Lymphoma* 10(1-2): 135-42), 2'-3-dimethyl-4-aminoazobenzene (ortho-aminoazotoluene, OAT) (Smetanina et al. (2011) *Toxicol. Appl. Pharmacol.* 255(1):76-85), 2-amino-1-methyl-6-phenylimidazo[4,5-b]pyridine (PhIP) (Lauber et al. (2004) *Carcinogenesis* 25(12):2509-17), β-estradiol (U.S. Pat. No. 7,544,511 B2), RU38486 (U.S. Pat. No. 7,544,511 B2), dexamethasone (U.S. Pat. No. 7,544,511 B2), thyroid hormones (U.S. Pat. No. 7,544,511 B2), retinoids (U.S. Pat. No. 7,544,511 B2), and ecdysone (U.S. Pat. No. 7,544,511 B2).

Exemplary Myc inhibitors include 7-nitro-N-(2-phenylphenyl)-2,1,3-benzoxadiazol-4-amine (10074-G5) (Clausen D M et al, (2010) *J. Pharmacol. Exp. Ther.* 335(3):715-27), thioxothiazolidinone [Z-]-5-[4-ethylbenzylidene]-2-thioxo-1,3-thiazolidin-4-one (10058-F4) (Clausen et al (2010) *J. Pharmacol. Exp. Ther.* 335(3):715-27; Lin C P et al (2007) *Anticancer Drugs,* 18(2): 161-70; Huang et al (2006) *Exp. Hematol.* 34(1 1): 1480-9), 4-phenylbutyrate (phenylbutyrate) (Engelhard et al (1998) *J. Neurooncol.* 37(2):97-108), Compound 0012 (Hurley et al (2010) *J. Vasc. Res.* 47(1): 80-90), curcumin (Aggarwal et al (2005) *Clin. Cancer Res.* 1 1(20):7490-8), magnesium hydroxide (Mori et al (1997) *J. Cell. Biochem. Suppl.* 27:35-41), BP-1-102 (Zhang et al (2012) *Proc. Natl. Acad. Sci. U.S.A.* 109(24):9623-8), WP1 193 (Sai et al (2012) *J. Neurooncol.* 107(3):487-501), BP-1-107 (Page et al (2012) *J. Med. Chem.* 55(3): 1047-55), BP-1-108 (Page et al (2012) *J. Med. Chem.* 55(3): 1047-55), SF-1-087 (Page et al (2012) *J. Med. Chem.* 55(3): 1047-55), SF-1-088 (Page et al (2012) *J. Med. Chem.* 55(3): 1047-55), STX-0119 (Ashizawa et al (2011) *Int. J. Oncol.* 38(5): 1245-52), substituted thiazol-4-one compounds (U.S. Pat. No. 7,872,027), (Z,E)-5-(4-ethylbenzylidene)-2-thioxothiazolidin-4-one (10058-F4) (U.S. Pat. No. 7,026,343), S2T1-60TD (U.S. Publication No. 20120107317A1), Quarfloxin (CX-3543) (U.S. Publication No. 20120107317A1), benzoylanthranilic acid (U.S. Publication No. 20120107317A1), cationic porphyrin TMPyP4 (U.S. Publication No. 20120107317A1), tyrphostin and tryphostin-like compounds (European Patent No. EP2487156A1), AG490 (European Patent No. EP2487156A1), FBXW-7 expression vectors (Ishikawa Y et al, supra), and siRNAs targeting Myc transcript (Id.).

Exemplary Notch activators include microRNAs that target FBXW-7 (Ishikawa Y et al supra), AG-370, 5 (U.S. Pat. No. 8,114,422), AG-1296 (6,7-dimethoxy-3-phenylquinoxaline) (Id.), nigericinNa (Id.), cytochalasin D (Id.), FCCP (carbonylcyanide-4-(trifluoromethoxy)-phenylhydrazone) (Id.), SP60012 (Id.), and vectors that produce protein of or isolated protein of Jagged-1, Jagged-2, Jagged-3, Serrate, any member of the Jagged/Serrate protein family, Delta, Delta-like-1, Delta-like-3, Delta-like-4, Delta-like homolog-1 (DLK1), any member of the Delta protein family, and any portion of any of these proteins (PCT Publication WO2004090110A3). Exemplary Notch activators may also include chemical activators such as valproic acid (VPA, see, U.S. Pat. No. 8,338,482), resveratrol and phenethyl isothiocyanate.

Exemplary Notch inhibitors include gamma-secretase inhibitors such as an arylsulfonamide, a benzodiazepine, L-685,458 (U.S. Patent Publication No. 2001/0305674), MK-0752 (Purow B. (2012) Adv. Exp. Med. Biol. 727:305-19; Imbimbo BP (2008) *Curr. Top. Med. Chem.* 8(1):54-61), DAPT ([N-(3,5-Difluorophenacetyl)-L-alanyl]-S-phenylglycine t-butyl ester) (Id.; Ishikawa Y et al. supra; PCT Publication WO2011 149762A3), LY-374973 (N—[N-(3,5-Difluorophenacetyl)-L-alanyl]-S-phenylglycine t-butyl ester) (PCT Publication WO2011 149762A3), N-[(3,5-Difluorophenyl)acetyl]-L-alanyl-2-phenyl]glycine-1,1-dimethylethyl ester (Id.); Lilly GSI L685,458 (Purow B, supra), compound E ((2S)-2-{[(3,5-Difluorophenyl)acetyl]amino}-N-[(3 S)-1-methyl-2-oxo-5-phenyl-2,3-dihydro-1H-1,4-benzodiazepin-3-yl]propanamide) (Purow B, supra), DBZ (dibenzazepine) (Purow B, supra), isocoumarin (Purow B, supra), JLK6 (7-amino-4-chloro-3-methoxyisocoumarin) (Purow B (2012) Adv. Exp. Med. Biol. 727:305-19), Compound 18 ([11-endo]-N-(5,6,7,8,9,10-hexahydro-6,9-methano benzo[9][8]annulen-11-yl)-thiophene-2-sulfonamide) (Purow B, supra), E2012 (Imbimbo BP, supra; PCT Publication WO2009005688A3), MRK560 (Imbimbo BP, supra), LY-411575 (Imbimbo BP, supra), LY-450139 (Imbimbo BP, supra; PCT Publication WO2009005688A3), γ-secretase inhibitor XII (PCT Publication WO2011 149762A3; PCT Publication WO2009005688A3), 2,2-dimethyl-N—((S)-6-oxo-6,7-dihydro-5H-dibenzo(b, d)azepin-7-yl)-N'-(2,2,3,3,3-pentafluoro-propyl)-malonamide (U.S. Patent Publication No. 20090181944A1), GSI-LX (EP 1949916B1), GSI-X (EP1949916B1), tocopherol derivatives (PCT Publication WO2009040423A1), [(2S)-2-{[(3,5-Difluorophenyl)acetyl]amino}-N-[(3S)l-methyl-2-oxo-5-phenyl-2,3-dihydro-1H-1,4-benzodiazepin-3-yl] propanamide] (PCT Publication WO2009005688A3), N—[N-(3,5-difluorophenacetyl)-L-alanyl]-Sphenylglycine-t-butylester (Id.), [1,1'-Biphenyl]-4-acetic acid (Id.), 2-fluoro-alpha-methyl (Id.), NGX-555 (Id.), LY-41 1575 (Id.), Cellzome (Id.), 2-Thiophenesulfonamide (Id.), 5-chloro-N-[(1S)-3,3,3-trifluoro-1-(hydroxymethyl)-2-(trifluoromethyl)propyl] (Id.), NIC5-15 (Id.), BMS (Id.), CHF-5074 (Id.), BMS-299897 (Imbimbo BP, supra), RO4929097; L-685458 ((5S)-(t-Butoxycarbonylamino)-6-phenyl-(4R) hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); MK-0752; YO-01027; MDL28170 (Sigma); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-1-alaninamide, see U.S. Pat. No. 6,541,466); ELN-46719 (2-hydroxy-valeric acid amide analog of LY411575 (where LY411575 is the 3,5-difluoro-mandelic acid amide) (U.S. Pat. No. 6,541, 466)); PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide; Samon et al., Mol. Cancer Ther. 2012; 11: 1565-1575); and Compound E ((2S)-2-{[(3,5-Difluorophenyl)acetyl]amino}-N-[(3 S)-1-methyl-2-oxo-5-phenyl-2,3-dihydro-1H-1,4-benzodiazepin-3-yl]propanamide; see WO 98/28268 and Samon et al., Mol. Cancer Ther. 2012; 11: 1565-1575; available from Alexis Biochemicals)), or pharmaceutically acceptable salts thereof. In some embodiments, suitable gamma secretase inhibitors include: semagacestat (also known as LY450139, (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethylbutanamide, available from Eli Lilly; WO 02/47671 and U.S. Pat. No. 7,468,365); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-L-alaninamide, available from Eli Lilly, Fauq et al, (2007) Bioorg. Med. Chem. Lett. 17: 6392-5); begacestat (also known as GSI-953, U.S. Pat. No. 7,300,951); arylsulfonamides (A S, Fuwa et al, (2006) Bioorg. Med. Chem. Lett. 16(16):4184-4189); N—[N-(3,5-difluorophenacetyl)-L-alanyl]-(S)-phenylglycine t-butyl ester (DAPT, Shih et al, (2007) Cancer Res. 67: 1879-1882); N4N-3,5-Difluorophenacetyl]-L-alanyl-S-phenylglycine Methyl Ester (also known as DAPM, gamma-Secretase Inhibitor XVI, available from EMD Millipore); Compound W (3,5-bis(4-Nitrophenoxy)benzoic acid, available from Tocris Bioscience); L-685,458 ((5S)-(tert-Butoxycarbonylamino)-6-phenyl-(4R)-hydroxy-(2R)-benzylhexanoyl)-L-leucy-L-phenylalaninamide, available from Sigma-Aldrich, Shearmen et al, (2000) Biochemistry 39, 8698-8704); BMS-289948 (4-chloro-N-(2,5-difluorophenyl)-N-((1R)-{4-fluoro-2-[3-(1H-imidazol-1-yl)propyl]phenyl}ethyl) benzenesulfonamide hydrochloride, available from Bristol Myers Squibb); BMS-299897 (4-[2-((1R)-1-{[(4-chlorophenyl)sulfonyl]-2,5-difluoroanilino}ethyl)-5-fluorophenyl]butanoic acid, available from Bristol Myers Squibb, see Zheng et al, (2009) Xenobiotica 39(7):544-55); avagacestat (also known as BMS-708163, (R)-2-(4-chloro-N-(2-fluoro-4-(1,2,4-oxadiazol-3-yl)benzyl)phenylsulfonamido)-5,5,5-trifluoropentanamide, available from Bristol Myers Squibb, Albright et al, (2013) J Pharmacol. Exp. Ther. 344(3):686-695); MK-0752 (3-(4-((4-chlorophenyl)sulfonyl)-4-(2,5-difluorophenyl)cyclohexyl)propanoic acid, available from Merck); MRK-003 ((3'R,6R,9R)-5'-(2,2,2-trifluoroethyl)-2-((E)-3-(4-(trifluoromethyl)piperidin-1-yl)prop-1-en-1-yl)-5, 6,7,8,9,10-hexahydrospiro[6,9-methanobenzo[8]annulene-11,3'-[1,2,5]thiadiazolidine], 1'-dioxide, available from Merck, Mizuma et al, (2012) Mol. Cancer Ther. 11(9): 1999-2009); MRK-560 (N-[cis-4-[(4-Chlorophenyl)sulfonyl]-4-(2,5-difluorophenyl)cyclohexyl]-1,1,1-trifluoromethanesulfonamide, Best et al, (2006) J. Pharmacol. Exp. Ther. 317(2):786-90); RO-4929097 (also known as R4733, (S)-2,2-dimethyl-N1-(6-oxo-6,7-dihydro-5H-dibenzo[b,d]azepin-7-yl)-N3-(2,2,3,3,3-pentafluoropropyl) malonamide, available from Hoffman-La Roche Inc., Tolcher et al, (2012) J. Clin. Oncol. 30(19):2348-2353); JLK6 (also known as 7-Amino-4-chloro-3-methoxyisocoumarin, available from Santa Cruz Biotechnology, Inc., Petit et al, (2001) Nat. Cell. Biol. 3: 507-511); Tarenflurbil (also known as (R)-Flurbiprofen, (2R)-2-(3-fluoro-4-phenylphenyl)propanoic acid); ALX-260-127 (also known as Compound 11, described by Wolfe et al, (1998) J. Med. Chem. 41: 6); Sulindac sulfide (S. Side, et al, (2003) J. Biol. Chem. 278(20): 18664-70); 1,1,1-trifluoro-N-(4-[5-fluoro-2-(trifluoromethyl)phenyl]-4-{[4 (trifluoromethyl)phenyl] sulfonyl}cyclohexyl)methanesulfonamide (U.S. Patent Publication No. 20110275719); N-[trans-3-[(4-chlorophenyl) sulfonyl]-3-(2,5-difluorophenyl)cyclobutyl]-1,1,1-trifluoromethanesulfonamide (U.S. Patent Publication No. 20110263580); N-[cis-3-[(4-chlorophenyl)sulfonyl]-3-(2,5-difluorophenyl)cyclobutyl]-1,1,1-trifluoromethanesulfonamide (U.S. Patent Publication No. 20110263580); N-[cis-3-[(4-chlorophenyl)sulfonyl]-3-(2-cyano-5-fluorophenyl) cyclobutyl]-1,1,1-trifluoromethanesulfonamide (U.S. Patent Publication No. 20110263580); N-[cis-3-[(4-chlorophenyl) sulfonyl]-3-(2,5-dichlorophenyl)cyclobutyl]-1,1,1-trifluoromethanesulfonamide (U.S. Patent Publication No. 20110263580); N-(cis-3-(2,5-difluorophenyl)-3-{[4-(trifluoromethyl)phenyl]sulfonyl}cyclobutyl)-1,1,1-trifluoromethanesulfonamide (U.S. Patent Publication No. 20110263580); N-{cis-3-(5-chloro-2-fluorophenyl)-3-[(4-chlorophenyl)sulfonyl]cyclobutyl}-1,1,1-trifluoromethanesulfonamide (U.S. Patent Publication No. 20110263580); N-{cis-3-(2,5-difluorophenyl)-3-[(4-fluorophenyl)sulfonyl] cyclobutyl}-1,1,1-trifluoromethanesulfonamide (U.S. Patent Publication No. 20110263580); N-{cis-3-(2,5-difluorophenyl)-3-[(3,4-difluorophenyl)sulfonyl]cyclobutyl}-1,1,1-trifluoromethanesulfonamide (U.S. Patent Publication No. 20110263580); N-[cis-3-[(4-cyanophenyl)sulfonyl]-3-(2,5- difluorophenyl)cyclobutyl]-1,1,1-trifluoromethanesulfonamide (U.S. Patent Publication No. 20110263580); 4-{[cis-3-[(4-chlorophenyl)sulfonyl]-3-(2,5-difluorophenyl)cyclobutyl][trifluoromethyl) sulfonyl]amino}butanoic acid (U.S. Patent Publication No. 20110263580); N-[cis-3-[(4-chlorophenyl)sulfonyl]-3-(2,5-difluorophenyl)cyclobutyl]-1,1,1-trifluoro-N-[2-(tetrahydro-2-pyran-2-yloxy)ethyl] methanesulfonamide (U.S. Patent Publication No. 201 10263580); Methyl{[cis-3-[(4-chlorophenyl)sulfonyl]-3-(2, 5-difluorophenyl)cyclobutyl][(trifluoromethyl)sulfonyl]amino}acetate (U.S. Patent Publication No. 201 10263580); N-[3-[(4-chlorophenyl)sulfonyl]-3-(2,5-difluorophenyl)cyclobutyl]-1,1,1-trifluoro-N-methylmethanesulfonamide (U.S. Patent Publication No. 20110263580); N-[3-[(4-chlorophenyl)sulfonyl]-3-(2,5-difluorophenyl)cyclobutyl]-1,1, 1-trifluoro-N-methylmethanesulfonamide (U.S. Patent Publication No. 201 10263580); Methyl 4-{[cis-3-[(4-chlorophenyl)sulfonyl]-3-(2,5-difluorophenyl)cyclobutyl] [(trifluoro-methyl)sulfonyl]amino}butanoate (U.S. Patent Publication No. 201 10263580); N-[cis-3-[(4-chlorophenyl) sulfonyl]-3-(2,5-difluorophenyl)cyclobutyl]-N-[(trifluoromethyl)sulfonyl]glycine (U.S. Patent Publication No. 20110263580); N-[cis-3-[(4-chlorophenyl)sulfonyl]-3-(2,5-difluorophenyl)-1-methylcyclobutyl]-1,1,1-trifluoromethanesulfonamide (U.S. Patent Publication No. 20110263580); N-(cis-3-(2,5-difluorophenyl)-1-methyl-3-{[4-(trifluoromethyl)phenyl]sulfonyl}cyclobutyl)-1,1,1-trifluoromethanesulfonamide (U.S. Patent Publication No. 20110263580); N-[cis-3-[(4-chlorophenyl)sulfonyl]-3-(2,5-difluorophenyl)cyclobutyl]-1,1,1-trifluoro-N-[(trifluoromethyl)sulfonyl]methanesulfonamide (U.S. Patent Publication No. 20110263580); Sodium[cis-3-[(4-chlorophenyl) sulfonyl]-3-(2,5-difluorophenyl)cyclobutyl][(trifluoromethyl)sulfonyl]azanide (U.S. Patent Publication No. 201 10263580); Potassium[cis-3-[(4-chlorophenyl)sulfonyl]-3-(2,5-difluorophenyl)cyclo butyl] [(trifluoromethyl)sulfonyl] azanide (U.S. Patent Publication No. 201 10263580); N-[cis-3-[(4-trifluoromethoxyphenyl)sulfonyl]-3-(2,5-difluorophenyl)cyclobutyl]-1,1,1-trifluoromethanesulfonamide (U.S. Patent Publication No. 201 10263580); 1,1,1-trifluoro-N-(4-[5-fluoro-2-(trifluoromethyl)phenyl]-4-{[4-(trifluoromethyl)phenyl]sulfonyl}cyclohexyl)methanesulfonamide (U.S. Patent Publication No. 201 10263580); gamma-Secretase Inhibitor I (also known as Z-Leu-Leu-Nle-CHO, benzyloxycarbonyl-leucyl-leucyl-norleucinal, available from Calbiochem); gamma-secretase inhibitor II: (MOL)(CDX) (available from Calbiochem); gamma secretase inhibitor III, (N-Benzyloxycarbonyl-Leu-leucinal, available from Calbiochem); gamma secretase inhibitor IV, (N-(2-Naphthoyl)-Val-phenylalaninal, available from Calbiochem); gamma-secretase inhibitor V (also known as Z-LF-CHO, N-Benzyloxycarbonyl-Leu-phenylalaninal, available from EMD Millipore); gamma-secretase inhibitor VI (1-(S)-endo-N-(1,3,3)-Trimethylbicyclo[2.2.1]hept-2-yl)-4-fluorophenyl Sulfonamide, available from EMD Millipore); gamma secretase inhibitor VII, (also known as Compound A, MOC-LL-CHO, Menthyloxycarbonyl-LL-CHO, available from Calbiochem); gamma secretase inhibitor X, ({1S-Benzyl-4R-[1-(1S-carbamoyl-2-phenethylcarbamoyl)-1S-3-methylbutylcarbamoyl]-2R-hydroxy-5-phenylpentyl}carbamic acid tert-butyl ester, available from Calbiochem); gamma secretase inhibitor XI, (7-Amino-4-chloro-3-methoxyisocoumarin, available from Calbiochem); gamma secretase inhibitor XII, (also known as Z-Ile-Leu-CHO, Shih and Wang, (2007) Cancer Res. 67: 1879-1882); gamma secretase inhibitor XIII, (Z-Tyr-Ile-Leu-CHO, available from Calbiochem); gamma secretase inhibitor XIV, (Z-Cys(t-Bu)-Ile-Leu-CHO, available from Calbiochem); gamma secretase inhibitor XVII, (also known as WPE-III-31C), (MOL)(CDX) (available from Calbiochem); gamma secretase inhibitor XIX, (also known as benzodiazepine, (2S,3R)-3-(3,4 Difluorophenyl)-2-(4-fluorophenyl)-4-hydroxy-N-((3 S)-2-oxo-5-phenyl-2,3-dihydro-1H-benzo[e][1,4]diazepin-3-yl)-butyramide, Churcher et al, (2003) J. Med. Chem. 46(12):2275-8); gamma secretase inhibitor XX, (also known as dibenzazepine, (S,S)-2-[2-(3, 5-Difluorophenyl)acetylamino]-N-(5-methyl-6-oxo-6,7-dihydro-5H-dibenzo[b,d]azepin-7-yl)propionamide, (MOL)(CDX) (Weihofen et al, Science 296: 2215-2218, 2002, available from Calbiochem); gamma secretase inhibitor XXI, ((S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide, available from Calbiochem); 5-methyl-2-propan-2-ylcyclohexyl)N-[4-methyl-1-[(4-methyl-1-oxopentan-2-yl)amino]-1-oxopentan-2-yl]carbamate (available from HDH Pharma Inc.); N-trans-3,5-Dimethoxycinnamoyl-Ile-leucinal (available from Calbiochem); N-tert-Butyloxycarbonyl-Gly-Val-Valinal; isovaleryl-V V-Sta-A-Sta-OCH$_3$ (available from Calbiochem); diethyl-(5-phenyl-3H-azepin-2-yl)-amine (U.S. Pat. No. 8,188,069); diethyl-(5-isopropyl-3H-azepin-2-yl)-amine (U.S. Pat. No. 8,188,069); diethyl-(4-phenyl-3H-azepin-2-yl)-amine (U.S. Pat. No. 8,188,069); diethyl-(6-phenyl-3H-azepin-2-yl)-amine (U.S. Pat. No. 8,188,069); 5-phenyl-1,3-dihydro-azepin-2-one (U.S. Pat. No. 8,188, 069); -Isopropyl-1,3-dihydro-azepin-2-one (U.S. Pat. No. 8,188,069); 4-phenyl-1,3-dihydro-azepin-2-one (U.S. Pat. No. 8,188,069); 6-phenyl-1,3-dihydro-azepin-2-one (U.S. Pat. No. 8,188,069); 2-butoxy-5-phenyl-3H-azepine (U.S. Pat. No. 8,188,069); 1-methyl-5-phenyl-1,3-dihydro-azepin-2-one (U.S. Pat. No. 8,188,069); 5-isopropyl-1-methyl-1,3-dihydro-azepin-2-one (U.S. Pat. No. 8,188,069); 1-methyl-4-phenyl-1,3-dihydro-azepin-2-one (U.S. Pat. No. 8,188,069); 1-methyl-6-phenyl-1,3-dihydro-azepin-2-one (U.S. Pat. No. 8,188,069); 1-methyl-5-phenyl-1H-azepine-2,3-dione-3-oxime (U.S. Pat. No. 8,188,069); 5-isopropyl-1-methyl-1H-azepine-2,3-dione-3-oxime (U.S. Pat. No. 8,188,069); 1-methyl-6-phenyl-1H-azepine-2,3-dione-3-oxime (U.S. Pat. No. 8,188,069); 1-methyl-4-phenyl-1H-azepine-2,3-dione-3-oxime (U.S. Pat. No. 8,188,069); 3-amino-1-methyl-5-phenyl-1,3-dihydro-azepin-2-one (U.S. Pat. No. 8,188,069); 3-amino-5-isopropyl-1-methyl-1, 3-dihydro-azepin-2-one (U.S. Pat. No. 8,188,069); 3-amino-1-methyl-4-phenyl-1,3-dihydro-azepin-2-one (U.S. Pat. No. 8,188,069); 3-amino-1-methyl-6-phenyl-1,3-dihydro-azepin-2-one (U.S. Pat. No. 8,188,069); (S)-[1-(1-methyl-2-oxo-5-phenyl-2,3-dihydro-1H-azepin-3-ylcarbamoyl)-ethyl]-carbamic acid tertbutyl ester (U.S. Pat. No. 8,188, 069); [(S)-1-(5-isopropyl-1-methyl-2-oxo-2,3-dihydro-1H-azepin-3-ylcarbamoyl)-ethyl]carbamic acid tert-butyl ester (U.S. Pat. No. 8,188,069); [(S)-1-(1-methyl-2-oxo-4-phenyl-2,3-dihydro-1H-azepin-3-ylcarbamoyl)-ethyl]carbamic acid tert-butyl ester (U.S. Pat. No. 8,188,069); [(S)-1-(1-methyl-2-oxo-6-phenyl-2,3-dihydro-1H-azepin-3-ylcarbamoyl)-ethyl]-carbamic acid tert-butyl ester (U.S. Pat. No. 8,188,069); (S)-2-amino-N-(1-methyl-2-oxo-5-phenyl-2,3-dihydro-1H-azepin-3-yl)-propionamide (U.S. Pat. No. 8,188,069); (S)-2-amino-N-(5-isopropyl-1-methyl-2-oxo-2, 3-dihydro-1H-azepin-3-yl)propionamide (U.S. Pat. No. 8,188,069); (S)-2-Amino-N-(1-methyl-2-oxo-6-phenyl-2,3-dihydro-1H-azepin-3-yl)propionamide hydrochloride (U.S. Pat. No. 8,188,069); (S)-2-Amino-N-(1-methyl-2-oxo-4-phenyl-2,3-dihydro-1H-azepin-3-yl) propionamide hydrochloride (U.S. Pat. No. 8,188,069); (S)-2-fluoro-3-methylbutyric acid (U.S. Pat. No. 8,188,069); (S)-2-hydroxy-3-methyl-N-[(S)-1-((S)-1-methyl-2-oxo-5-phenyl-2,3-dihydro-1H-azepin-3-ylcarbamoyl)-ethyl]-butyramide (U.S. Pat. No. 8,188,069); (S)-2-fluoro-3-methyl-N-[(S)-1-(1-methyl-2-oxo-5-phenyl-2,3-dihydro-1H-azepin-3-ylcarbamoyl)-ethyl]-butyramide (U.S. Pat. No. 8,188,069); (S)-2-hydroxy-N-[(S)-1-(5-isopropyl-1-methyl-2-oxo-2,3-dihydro-1H-azepin-3-ylcarbamoyl)ethyl]-3-methyl-butyramide (U.S. Pat. No. 8,188,069); (S)-2-hydroxy-3-methyl-N-[(S)-1-(1-methyl-2-oxo-4-phenyl-2,3-dihydro-1H-azepin-3-ylcarbamoyl)-ethyl]-butyramide (U.S. Pat. No. 8,188,069); (S)-2-hydroxy-3-methyl-N-[(S)-1-(1-methyl-2-oxo-6-phenyl-2,3-dihydro-1H-azepin-3-ylcarbamoyl)-ethyl]-butyramide (U.S. Pat. No. 8,188,069); and (S)-2-fluoro-3-methyl-N-[(S)-1-(1-methyl-2-oxo-6-phenyl-2,3-dihydro-1H-azepin-3-ylcarbamoyl)-ethyl]-butyramide (U.S. Pat. No. 8,188,069), and pharmaceutically acceptable salts thereof.

Additional exemplary Notch inhibitors include nonsteroidal anti-inflammatory drugs (NSAIDs) such as flurbiprofen (Purow B, supra), MPC-7869 (Imbimbo BP, supra), ibuprofen (Id.), sulindac sulphide, indomethacin, alpha-secretase inhibitors (ASIs) (Purow B, supra), the Na$^+$/H$^+$ antiporter Monensin (Id.); small molecules that block Notch binding to interacting proteins such as Jagged, Numb, Numb-like, CBF1 transcription factor, and mastermind-like (MAML) (Id.; Ishikawa Y et al, supra.); antibodies that bind Notch proteins or Notch ligands such as Delta-Like-4 (Purow B, supra); stapled peptides that bind Notch such as SAHM1 (Id.); dominant-negative forms of genes such as MAML (Id; Ishikawa Y et al., supra), Numb/Numb-Like (Purow B, supra), and FBXW-7 (Id.); expression vectors that increase levels of Notch regulators such as FBXW-7 (Id.; Ishikawa Y et al., supra); siRNAs that target Notch transcripts (Purow B, supra); microRNAs such as miR-326, miR-34a, microRNA-206, and miR-124 (Id.); and Notch antibodies (U.S. Pat. No. 8,226,943, U.S. Publication No. 20090258026A2, PCT Publication WO2012080926A2).

Exemplary Atoh1 activators include, for example, β-Catenin or β-catenin pathway agonists, e.g., Wnt ligands, DSH/DVL1, 2, 3, LRP65N, WNT3A, WNTSA, and WNT3A, 5A. Additional Wnt/β-catenin pathway activators and inhibitors are reviewed in the art (Moon et al, *Nature Reviews Genetics*, 5:689-699, 2004). In some embodiments, suitable Wnt/-catenin pathway agonists can include antibodies and antigen binding fragments thereof, and peptides that bind specifically to frizzled (Fzd) family of receptors.

Kinase inhibitors, e.g., casein kinase 1 (CK1) and glycogen synthase kinase 3 β (GSK3) inhibitors can also act as β-Catenin or β-catenin pathway agonists to activate Atoh1. GSK3 β inhibitors include, but are not limited to, lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)[1,3,4]-oxadiazole (GSK3 inhibitor II), 2,4-dibenzyl-5-oxothiadiazolidine-3-thione (OTDZT), (27,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl)urea (AR-A014418), and indirubins (e.g., indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5-bromoindirubin), 4-Benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), a-4-Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), and H-KEAPPAPPQSpP-NH2 (SEQ ID NO: 58) (L803) or its cell-permeable derivative Myr-N-GKEAPPAPPQSpP-NH2 (SEQ ID NO: 59) (L803-mts). Other GSK3β inhibitors are disclosed in U.S. Pat. Nos. 6,417,185; 6,489,344; and 6,608,063. In some embodiments, suitable kinase inhibitors can include RNAi and siRNA designed to decrease GSK3β and/or CK1 protein levels. In some embodiments, useful kinase inhibitors include FGF pathway inhibitors. In some embodiments, FGF pathway inhibitors include, for example, SU5402.

Additional Atoh1 activators include gamma secretase inhibitors (e.g., aryl sulfonamides, dibenzazepines, benzodiazepines, N—[N-(3,5-difluorophenacetyl)-L-alanyl]-(S)-phenylglycine t-butyl ester (DAPT; EMD Biosciences, San Diego, CA, USA), L-685,458, or MK0752ho, in addition to those listed above under Notch inhibitors), gentamycin, and the combination of transcription factors Eya1 and Six1 (and optionally Sox2), as described in Ahmed et al (2012) *Dev. Cell.* 22(2):377-390.

Additional Atoh1 activators are described in U.S. Pat. No. 8,188,131, including a compound represented by Formula I:

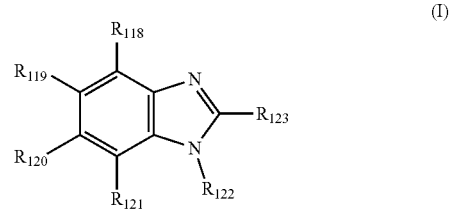

(I)

wherein:
each of $R_{118}$, $R_{119}$, $R_{120}$, and $R_{121}$ is, independently selected from H, halo, OH, CN, $NO_2$, $C_1$-$C_3$ alkyl, $C_1$-$C_3$ haloalkyl, alkoxy, and $C_1$-$C_8$ haloalkoxy;
$R_{122}$ is hydrogen or —Z—$R^a$; wherein:
Z is O or a bond; and
$R^a$ is:
(i) $C_1$-$C_6$ alkyl or $C_1$-$C_6$ haloalkyl, each of which is optionally substituted with from 1-3 $R^b$; or
(ii) $C_3$-$C_{10}$ cycloalkyl, $C_3$-$C_{10}$ cycloalkenyl, each of which is optionally substituted with from 1-5 $R^c$; or
(iii) $C_7$-$C_{11}$ aralkyl, or heteroaralkyl including 6-11 atoms, each of which is optionally substituted with from 1-5 $R^c$;
(iv) $C_6$-$C_{10}$ aryl or heteroaryl including 5-10 atoms, each of which is optionally substituted with from 1-5 $R^d$;
$R_{123}$ is:
(i) hydrogen; or
(ii) $C_1$-$C_6$ alkyl or $C_1$-$C_6$ haloalkyl, each of which is optionally substituted with from 1-3 $R^b$; or
(iii) $C_6$-$C_{10}$ aryl or heteroaryl including 5-10 atoms, each of which is optionally substituted with from 1-5 $R^d$; or
(iv) $C_7$-$C_{11}$ aralkyl, or heteroaralkyl including 6-11 atoms, each of which is optionally substituted with from 1-5 $R^c$; or
(v) —($C_1$-$C_6$ alky-$Z^1$—($C_6$-$C_{10}$ aryl), wherein $Z^1$ is O, S, NH, or N(CH$_3$); the alkyl portion is optionally substituted with from 1-3 $R^b$; and the aryl portion is optionally substituted with from 1-5 $R^d$; or
(vi) —($C_1$-$C_6$ alkyl)-$Z^2$-(heteroaryl including 5-10 atoms), wherein $Z^2$ is O, S, NH, or N(CH$_3$); the alkyl portion is optionally substituted with from 1-3 $R^b$; and the heteroaryl portion is optionally substituted with from 1-5 $R^d$; or
(vii) —($C_1$-$C_6$ alkyl)-$Z^3$—($C_3$-$C_{10}$ cycloalkyl), wherein $Z^3$ is O, S, NH, or N(CH$_3$); the alkyl portion is optionally substituted with from 1-3 $R^b$; and the cycloalkyl portion is optionally substituted with from 1-5 $R^c$;

$R^b$ at each occurrence is, independently:
(i) NH$_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; or
(ii) $C_3$-$C_7$ cycloalkyl optionally substituted with from 1-3 substituents independently selected from $C_1$-$C_6$ alkyl, NH$_2$; NH($C_1$-$C_3$ alkyl); N($C_1$-$C_3$ alkyl)$_2$; hydroxy; $C_1$-$C_6$ alkoxy or $C_1$-$C_6$ haloalkoxy;

$R^c$ at each occurrence is, independently:
(i) halo; NH$_2$; NH($C_1$-$C_3$ alkyl); N($C_1$-$C_3$ alkyl)$_2$; hydroxy; $C_1$-$C_6$ alkoxy; $C_1$-$C_6$ haloalkoxy; or oxo; or
(ii) $C_1$-$C_6$ alkyl or $C_1$-$C_6$ haloalkyl; and $R^d$ at each occurrence is, independently:
(i) halo; NH$_2$; NH($C_1$-$C_3$ alkyl); N($C_1$-$C_3$ alkyl)$_2$; hydroxy; $C_1$-$C_6$ alkoxy or $C_1$-$C_6$ haloalkoxy; nitro; —NHC(O)($C_1$-$C_3$ alkyl); or cyano; or
(ii) $C_1$-$C_6$ alkyl or $C_1$-$C_6$ haloalkyl; or a pharmaceutically acceptable salt thereof.

Other exemplary Atoh1 activators described in U.S. Pat. No. 8,188,131 include 4-(4-chlorophenyl)-1-(5H-pyrimido[5,4-b]indol-4-yl)-1H-pyrazol-3-amine; 6-chloro-1-(2-chlorobenzyloxy)-2-phenyl-1H-benzo[d]imidazole; 6-chloro-1-(2-chlorobenzyloxy)-2-(4-methoxyphenyl)-1H-benzo[d]imidazole; 6-chloro-2-(4-methoxyphenyl)-1-(4-methylbenzyloxy)-1H-benzo[d]imidazole; 6-chloro-1-(3,5-dimethylbenzyloxy)-2-(4-methoxyphenyl)-1H-benzo[d]imidazole; 6-chloro-1-(4-methoxybenzyloxy)-2-(4-methoxyphenyl)-1H-benzo[d]imidazole; 1-(4-methylbenzyloxy)-6-nitro-2-phenyl-1H-benzo[d]imidazole; 4-(1H-benzo[d]imidazol-2-yl)phenol; 2,5-dichloro-N-((1-methyl-1H-benzo[d]imidazol-2-yl)methyl)aniline; 4-(2-(1-methyl-1H-benzo[d]imidazol-2-yl)ethyl)aniline; 2-((2-methoxyphenoxy)methyl)-1H-benzo[d]imidazole; 2-((4-fluorophenoxy)methyl)-1-methyl-1H-benzo[d]imidazole; 2-(phenylthiomethyl)-1H-benzo[d]imidazole; 3-(6-methyl-1H-benzo[d]imidazole-2-yl)-2H-chromen-2-imine; N-(2-(1H-benzo[d]imidazole-2-yl)phenyl)isobutyramide; 2-(o-tolyloxymethyl)-1H-benzo[d]imidazole; 2-(4-methoxyphenyl)-1-phenethyl-1H-benzo[d]imidazole; N-(6-bromobenzo[d]thiazole-2-yl)thiophene-2-carboxamide; N-(benzo[d]thiazole-2-yl)-1-methyl-1H-pyrazole-5-carboxamide; 2-(4-fluorobenzylthio)benzo[d]thiazole; 5-chloro-N-methylbenzo[d]thiazole-2-amine; N-(6-acetamidobenzo[d]thiazol-2-yl)furan-2-carboxamide; N-(6-fluorobenzo[d]thiazole-2-yl)-3-methoxybenzamide; 2-(benzo[d]oxazol-2-ylthio)-N-(2-chlorophenyl)acetamide; 5-chloro-2-phenylbenzo[d]oxazole; 5-methyl-2-m-tolylbenzo[d]oxazole; 2-(4-isobutoxyphenyl)-3-(naphthalen-2-yl)-2,3-dihydroquinazolin-4(1H)-one; N-(2-(2-(4-fluorophenyl)-2-oxoethylthio)-4-oxoquinazolin-3(4H)-yl)benzamide; 2-(4-chlorophenyl)-4-(4-methoxyphenyl)-1,4-dihydrobenzo[4,5]imidazo[1,2-a]pyrimidine; 2-(3-pyridyl)-4-(4-bromophenyl)-1,4-dihydrobenzo[4,5]imidazo[1,2-a]pyrimidine; N-sec-butyl-1,7,7-trimethyl-9-oxo-8,9-dihydro-7H-furo[3,2-f]chromene-2-carboxamide; N-(3-carbamoyl-5,6-dihydro-4H-cyclopenta[b]thiophen-2-yl)benzofuran-2-carboxamide; 3-chloro-N-(5-chloropyridin-2-yl)benzo[b]thiophene-2-carboxamide; 3-chloro-N-((tetrahydrofuran-2-yl)methyl)benzo[b]thiophene-2-carboxamide; N-(3-(5-chloro-3-methylbenzo[b]thiopen-2-yl)-1H-pyrazol-5-yl)acetamide; 2-(naphthalen-2-yl)-1H-indole; 2-(pyridin-2-yl)-1H-indole; N-(2-chlorophenyl)-2-(1H-indole-3-yl)-2-oxoacetamide; 2-m-tolylquinoline; 2-(4-(2-methoxyphenyl)piperazin-1-yl)quinolone; 2-(1H-benzo[d][1,2,3]triazol-1-yl)-N-(2,3-dihydro-1H-inden-2-yl)acetamide; 1-phenethyl-1H-benzo[d][1,2,3]triazole; 7-(4-fluorobenzyloxy)-2H-chromen-2-one; N-(2,4-dichlorophenyl)-8-methoxy-2H-chromene-3-carboxamide; N-(3-chlorophenyl)-8-methyl-3,4-dihydroquinoline-1(2H)-carbothioamide; 7-methoxy-5-methyl-2-phenyl-4H-chromen-4-one; 2-(3,4-dimethylphenyl)quinoxaline; 4-bromo-N-(5-chloropyridin-2-yl)benzamide; 3-amino-6,7,8,9-tetrahydro-5H-cyclohepta[e]thieno[2,3-b]pyridine-2-carboxamide; (Z)-3-methyl-N'-(nicotinoyloxy)benzimidamide; N,N-diethyl-6-methoxythieno[2,3-b]quinoline-2-carboxamide; 6-(4-methoxyphenyl)-1,2,3,4-tetrahydro-1,5-naphthyridine; 5-bromo-N-(2-(phenylthio)ethyl) nicotinamide; N-(6-methylpyridin-2-yl)-2,3-dihydrobenzo[b][1,4]dioxine-6-carboxamide; 2-(4-methylbenzylthio)oxazolo[4,5-b]pyridine; N-(2-methoxyethyl)-5-p-tolylpyrimidin-2-amine; 4-(5-(benzo[b]thiophen-2-yl)pyrimidin-2-yl)morpholino; 4-(5-(4-fluorophenyl)pyrimidin-2-yl)morpholino; N-(4-bromo-3-methylphenyl)quinazoline-4-amine; N-(4-methoxyphenyl)quinazolin-4-amine; N-(3-methoxyphenyl)-9H-purin-6-amine; N,N-diethyl-1-m-tolyl-1H-pyrazolo[3,4-d]pyrimidin-4-amine; (5-(4-bromophenyl)furan-2-yl)(morpholino)methanone; (Z)-4-bromo-N'-(furan-2-carbonyloxy)benzimidamide; N-(4-iodophenyl)furan-2-carboxamide; 5-(5-(2,4-difluorophenyl)furan-2-yl)-1-(methylsulfonyl)-1H-pyrazole; 1-(3-amino-5-(4-tert-butylphenyl)thiophen-2-yl)ethanone; N-(3-cyano-4,5,6,7-tetrahydrobenzo[b]thiophen-2-yl)-2-fluorobenzamide; N-(5-chloropyridin-2-yl)thiophene-2-carboxamide; N-(2-(4-fluorophenoxy)ethyl)thiophene-2-carboxamide; 2,5-dimethyl-N-phenyl-1-(thiophen-2-ylmethyl)-1H-pyrrole-3-carboxamide; N-(3-cyanothiophen-2-yl)-4-isopropoxybenzamide; 2-(4-methoxyphenoxy)-N-(thiazol-2-yl)acetamide; 4-(4-methoxyphenyl)-N-(3-methylpyridin-2-yl)thiazol-2-amine; 4-(biphenyl-4-yl)thiazol-2-amine; 4-(4-(4-methoxyphenyl)thiazol-2-yl)-3-methylisoxazol-5-amine; N-(2-methoxyphenyl)-4-phenylthiazol-2-amine; 1-(4-amino-2-(m-tolylamino)thiazol-5-yl)-2-methylpropan-1-one; 4-(4-chlorophenyl)-1-(5H-pyrimido[5,4-b]indol-4-yl)-1H-pyrazol-3-amine; 2-(4-chlorophenyl)-6-ethyl-5-methylpyrazolo[1,5-a]pyrimidin-7(4H)-one; 5-methoxy-2-(5-phenyl-1H-pyrazol-3-yl)phenol; (3-(4-bromophenyl)-1-phenyl-1H-pyrazol-4-yl)methanol; N-(2,5-dichlorophenyl)-1-ethyl-1H-pyrazole-3-carboxamide; 4-chloro-1-methyl-N-(2-oxo-2-phenylethyl)-1H-pyrazole-3-carboxamide; N-(3-(5-tert-butyl-2-methylfuran-3-yl)-1H-pyrazol-5-yl)benzamide; N-(5-methylisoxazol-3-yl)benzo[d][1,3]dioxole-5-carboxamide; (5-(4-bromophenyl)isoxazole-3-yl)(morpholino)methanone; N-(4-bromophenyl)-5-isopropylisoxazole-3-carboxamide; 5-((4-chloro-2-methylphenoxy)methyl)-3-(pyridin-4-yl)-1,2,4-oxadiazole; 5-(2-methoxyphenyl)-3-p-tolyl-1,2,4-oxadiazole; 5-(phenoxymethyl)-3-(pyridin-3-yl)-1,2,4-oxadiazole; 5-(2-chloro-4-methylphenyl)-3-(pyridin-3-yl)-1,2,4-oxadiazole; 3-(2-chlorophenyl)-5-p-tolyl-1,2,4-oxadiazole; 5-(piperidin-1-ylmethyl)-3-p-toyl-1,2,4-oxadiazole; 5-(4-bromophenyl)-3-(pyridin-3-yl)-1,2,4-oxadiazole; 5-(2-bromophenyl)-3-(4-bromophenyl)-1,2,4-oxadiazole; 5-(2-bromo-5-methoxyphenyl)-3-(thiophenyl-2-yl)-1,2,4-oxadiazole; 3-(2-fluorophenyl)-N-(3-(piperidin-1-yl)propyl)-1,2,4-oxadiazol-5-amine; 2-(2-chlorobenzoyl)-

N-(4-fluorophenyl)hydrazinecarbothioamide; 2-(methylamino)-N-phenethylbenzamide; 4-tert-butyl-N-((tetrahydrofuran-2-yl)methyl)benzamide; 2-phenyl-5-o-tolyl-1,3,4-oxadiazole; 4-(3-(4-chlorophenyl)-4,5-dihydro-1H-1,2,4-triazole-5-yl)-N,N-dimethylaniline; 7-methoxy-2-(4-methoxyphenyl)-1,10b-dihydrospiro[benzo[e]pyrazolo[1,5-c][1,3]oxazine-5,1'-cyclohexane]; 6-oxo-2-(4-(3-(trifluoromethyl)phenoxy)phenyl)-1,4,5,6-tetrahydropyridine-3-carbonitrile; 6-(4-methoxyphenyl)imidazo[2,1-b]thiazole; 2-(2-bromophenoxy)-N-(4H-1,2,4-triazol-3-yl)acetamide; 1-(indolin-1-yl)-2-phenoxyethanone; 2-(4-chlorophenyl)-6,7,8,9-tetrahydrobenzo[e]imidazo[1,2-b][1,2,4]triazine; and pharmaceutically acceptable salts thereof.

Delivery of Agents for Modulating Myc, Notch and Atoh1: The method of delivery of modulators of Myc, Notch or Atoh1 activity will depend, in part, upon whether the hair cells or supporting cells are being contacted with the agents of interest in vivo or ex vivo. In the in vivo approach, the agents are delivered into the inner ear of a mammal. In the ex vivo approach, cells are contacted with the agents ex vivo. The resulting hair cells can then be transplanted into the inner ear of a recipient using techniques known and used in the art.

In certain embodiments, Myc activity is increased by administering Myc protein or a Myc activator in the inner ear of a recipient to give, for example, a final concentration of greater than about 30 µM, for example, in the range of about 30 µM to about 1000 µM. In certain embodiments, the Myc protein or Myc activator can be administered in an amount sufficient to give a final concentration of greater than about 30 µM. For example, the Myc protein or Myc activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, Myc protein or a Myc activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the Myc protein or Myc activator can be administered locally to the inner ear of a mammal. In one embodiment, 0.5 mg of Myc protein or Myc activator is administered locally to the inner ear. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of Myc protein or Myc activator can be administered locally to the inner ear of a mammal.

In certain embodiments, Notch activity is increased by administering a Notch protein, a NICD protein or a Notch activator to an inner ear of a recipient to give a final concentration of greater than about 30 µM, for example, in the range of about 30 µM to about 1000 µM. In certain embodiments, a Notch protein, NICD protein or Notch activator can be administered in an amount sufficient to give a final concentration of greater than about 30 µM. For example, the Notch protein, NICD protein or Notch activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, Notch protein, NICD protein or Notch activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the Notch protein, NICD protein or Notch activator can be administered locally to the inner ear of a mammal. In one embodiment, 0.5 mg of Notch protein, NICD protein or Notch activator is administered locally to the inner ear of a mammal. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of Notch protein, NICD protein or Notch activator can be administered locally to the inner ear of a mammal.

In certain embodiments, after cell proliferation has occurred, Notch activity is inhibited by administering a Notch inhibitor. A Notch inhibitor can be administered to give a final concentration of greater than about 30 µM, for example, in the range of about 30 µM to about 1000 µM. In certain embodiments, a Notch inhibitor can be administered in an amount sufficient to give a final concentration of greater than about 30 µM. For example, the Notch inhibitor may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM. In certain embodiments, the Notch inhibitor is administered in an amount sufficient to give a final concentration of about 400 µM.

In other embodiments, a Notch inhibitor is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the Notch inhibitor can be administered locally to the inner ear of a mammal. In one embodiment, 0.5 mg of Notch inhibitor is administered locally to the inner ear of a mammal. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of Notch inhibitor can be administered locally to the inner ear of a mammal. In certain embodiments, about 0.7 mg Notch inhibitor is administered locally to the inner ear of a mammal.

In certain embodiments, Atoh1 activity is increased by administering Atoh1 protein or an Atoh1 activator in the inner ear of a recipient to give, for example, a final concentration of greater than about 30 µM, for example, in the range of about 30 µM to about 1000 µM. In certain embodiments, the Atoh1 protein or Atoh1 activator can be administered in an amount sufficient to give a final concentration of greater than about 30 µM. For example, the Atoh1 protein or Atoh1 activator may be administered in an amount sufficient to give a final concentration in the range from about 30 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM.

In other embodiments, Atoh1 protein or a Atoh1 activator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the Atoh1 protein or Atoh1 activator can be administered locally to the inner ear of a mammal. In one embodiment, 0.5 mg of Atoh1 protein or Atoh1 activator is administered locally to the inner ear. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of Atoh1 protein or Atoh1 activator can be administered locally to the inner ear of a mammal.

Alternative Methods for Delivery of DNA

In some aspects, the activity of Myc, Notch or Atoh1 can be increased in a target cell using expression constructs known in the art, e.g., naked DNA constructs, DNA vector based constructs, and/or viral vector and/or viral based constructs to express nucleic acids encoding a desired Myc, Notch or Atoh1 protein. In certain embodiments, a single DNA construct expressing Myc and Notch or NICD as two separate genes can be delivered into the inner ear of a subject. In certain embodiments, a single DNA construct expressing Myc and Notch or NICD and Atoh1 as three separate genes can be delivered into the inner ear of a subject.

Exemplary expression constructs can be formulated as a pharmaceutical composition, e.g., for administration to a subject. DNA constructs and the therapeutic use of such constructs are well known to those of skill in the art (see, e.g. Chiarella et al. (2008) *Recent Patents Anti-Infect. Drug Disc.* 3: 93-101; Gray et al. (2008) *Expert Opin. Biol. Ther.* 8:911-922; Melman et al. (2008) *Hum. Gene Ther.* 17: 1165-1176). Naked DNA constructs typically include one or more therapeutic nucleic acids (e.g., DNA encoding Myc and/or Notch) and a promoter sequence. A naked DNA construct can be a DNA vector, commonly referred to as pDNA. Naked DNA typically does not integrate into chromosomal DNA. Generally, naked DNA constructs do not require, or are not used in conjunction with, the presence of lipids, polymers, or viral proteins. Such constructs may also include one or more of the non-therapeutic components described herein.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not integrate into chromosomal DNA.

Generally, DNA vectors include at least one promoter sequence that allows for replication in a target cell. Uptake of a DNA vector may be facilitated by combining the DNA vector with, for example, a cationic lipid, and forming a DNA complex. Typically, viral vectors are double stranded circular DNA molecules that are derived from a virus. Viral vectors typically are larger in size than naked DNA and DNA vector constructs and have a greater capacity for the introduction of foreign (i.e., not virally encoded) genes. Like naked DNA and DNA vectors, viral vectors can be used to deliver and express one or more therapeutic nucleic acids in target cells. Unlike naked DNA and DNA vectors, certain viral vectors stably incorporate themselves into chromosomal DNA. Typically, viral vectors include at least one promoter sequence that allows for replication of one or more vector encoded nucleic acids, e.g., a therapeutic nucleic acid, in a host cell. Viral vectors may optionally include one or more non-therapeutic components described herein. Advantageously, uptake of a viral vector into a target cell does not require additional components, e.g., cationic lipids. Rather, viral vectors transfect or infect cells directly upon contact with a target cell.

The approaches described herein include the use of retroviral vectors, adenovirus-derived vectors, and/or adeno-associated viral vectors as recombinant gene delivery systems for the transfer of exogenous genes in vivo, particularly into humans. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

Viruses that are used as transduction agents of DNA vectors and viral vectors such as adenoviruses, retroviruses, and lentiviruses may be used in practicing the present invention. Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, an adenovirus can be used in accordance with the methods described herein. The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors.

Adeno-associated virus is a naturally occurring defective virus that requires another virus, such as an adenovirus or a herpes virus, as a helper virus for efficient replication and a productive life cycle. It is also one of the few viruses that may integrate its DNA into non-dividing cells, and exhibits a high frequency of stable integration.

In various embodiments, one or more viral vectors that expresses a therapeutic transgene or transgenes encoding a polypeptide or polypeptides of the invention (e.g., Atoh1, Notch, Myc) is administered by direct injection to a cell, tissue, or organ of a subject, in vivo.

In some embodiments of the invention, it may be desirable to use a cell, cell type, cell lineage or tissue specific expression control sequence to achieve cell type specific, lineage specific, or tissue specific expression of a desired polynucleotide sequence, for example, to express a particular nucleic acid encoding a polypeptide in only a subset of cell types, cell lineages, or tissues, or during specific stages of development. Illustrative examples of cell, cell type, cell lineage or tissue specific expression control sequences include, but are not limited to: an Atoh1 enhancer for all hair cells; a Pou4f3 promoter for all hair cell; a Myo7a promoter for all hair cells; a Hes5 promoter for vestibular supporting cells and cochlear inner phalangeal cells, Deiters cells and Pillar cells; and GFAP promoter for vestibular supporting cells and cochlear inner phalangeal cells, Deiters cells and Pillar cells.

Certain embodiments of the invention provide conditional expression of a polynucleotide of interest. For example, expression is controlled by subjecting a cell, tissue, organism, etc., to a treatment or condition that causes the polynucleotide to be expressed or that causes an increase or decrease in expression of the polynucleotide encoded by the polynucleotide of interest. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al, 2003, *Gene*, 323: 67), the cumate inducible gene switch (WO 2002/088346), tetracycline-dependent regulatory systems, etc.

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al, (1977) *Cell*, 11:223-232) and adenine phosphoribosyltransferase (Lowy et al, (1990) *Cell*, 22:817-823) genes which can be employed in tk– or aprt– cells, respectively.

In certain embodiments, DNA delivery may occur by use of liposomes, nanocapsules, microparticles, microspheres, lipid particles, vesicles, optionally mixing with cell penetrating polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Duration of Delivery

The duration of Myc, Notch and Atoh1 activation can be varied to achieve a desired result. For example, it may be beneficial to expose a target cell to a Myc protein or Myc activator and a Notch protein, NICD protein, or a Notch activator for one to six days, one week, two weeks, three weeks, one month, three months, six months, nine months, one year, two years or more. Alternatively, when Myc is increased by constitutive activation (e.g., using an adenovirus to overexpress Myc), the duration of increased Myc activity can be controlled by administering a Myc inhibitor following administration of a myc protein or a myc activator. Inhibiting Myc activity after a period of increased Myc activity can be used to control proliferation, promote cell survival, and avoid tumorigenesis.

Similarly, the duration of increased Notch activity can be controlled by administering a Notch inhibitor, as discussed above, following administration of a Notch protein, NICD protein, or a Notch activator.

Route of Administration and Formulation

The route of administration will vary depending on the disease being treated. Hair cell loss, sensorineural hearing loss, and vestibular disorders can be treated using direct therapy using systemic administration and/or local administration. In certain embodiments, the route of administration can be determined by a subject's health care provider or clinician, for example following an evaluation of the subject.

The invention provides (i) a composition for use in proliferating or regenerating a cochlear or a utricular hair cell, (ii) a composition for use in proliferating or regenerating a cochlear or a utricular supporting cell, (iii) a composition for use in reducing the loss of, maintaining, or promoting hearing in a subject, and (iv) a composition for use in reducing the loss of, maintaining, or promoting vestibular function in a subject. Accordingly, the invention provides a first composition comprising an agent, for example, each of the agents discussed hereinabove, for example, an agent that increases Myc activity and/or an agent that increases Notch activity within a hair or supporting cell, either alone or in combination with a pharmaceutically acceptable carrier for use in each of the foregoing approaches. In addition, the invention provides a second composition comprising an agent, for each of the agents discussed hereinabove, for example, an agent that reduces or inhibits Myc activity and/or an agent that reduces or inhibits Notch activity within a hair or supporting cell, either alone or in combination with in a pharmaceutically acceptable carrier for use in each of the foregoing approaches. When supporting cells are regenerated, the invention provides a third composition comprising an agent, for example, an agent for increasing Atoh1 activity, to induce trans differentiation of a proliferated supporting cell into a hair cell.

In addition, it is contemplated that the Myc protein or activator and/or the Notch protein, NICD protein, or Notch activator, and/or Atoh1 protein or activator can be formulated so as to permit release of one or more proteins and/or activators over a prolonged period of time. A release system can include a matrix of a biodegradable material or a material, which releases the incorporated active agents. The active agents can be homogeneously or heterogeneously distributed within a release system. A variety of release systems may be useful in the practice of the invention, however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic.

In certain embodiments, the agents can be administered to a subject, e.g., a subject identified as being in need of treatment for hair cell loss, using a systemic route of administration. Systemic routes of administration can include, but are not limited to, parenteral routes of administration, e.g., intravenous injection, intramuscular injection, and intraperitoneal injection; enteral routes of administration, e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

Alternatively or in addition, the agents can be administered to a subject, e.g., a subject identified as being in need of treatment for hair cell loss, using a local route of administration. Such local routes of administration include administering one or more compounds into the ear of a subject and/or the inner ear of a subject, for example, by injection and/or using a pump.

In certain embodiments, the agents may be injected into the ear (e.g., auricular administration), such as into the luminae of the cochlea (e.g., the Scala media, Sc vestibulae, and Sc tympani). For example, the agents can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlea capsule.

In other embodiments, the agents can be delivered via nanoparticles, for example, protein-coated nanoparticles. Nanoparticles can be targeted to cells of interest based on cell-type specific receptor affinity for ligands coating the nanoparticles. The dosage of the agent can be modulated by regulating the number of nanoparticles administered per dose.

Alternatively, the agent may be administered to the inner ear using a catheter or pump. A catheter or pump can, for example, direct the agent into the cochlea luminae or the round window of the ear. Exemplary drug delivery systems suitable for administering one or more compounds into an ear, e.g., a human ear, are described in U.S. Patent Publication No. 2006/0030837 and U.S. Pat. No. 7,206,639. In certain embodiments, a catheter or pump can be positioned, e.g., in the ear (e.g., the outer, middle, and/or inner ear) of a subject during a surgical procedure.

Alternatively or in addition, the agents can be delivered in combination with a mechanical device such as a cochlea implant or a hearing aid, which is worn in the outer ear.

In certain embodiments, the modes of administration described above may be combined in any order and can be simultaneous or interspersed. For example, the agents may be administered to a subject simultaneously or sequentially. It will be appreciated that when administered simultaneously, the agents may be in the same pharmaceutically acceptable carrier (e.g., solubilized in the same viscoelastic carrier that is introduced into the inner ear) or the two agents may be dissolved or dispersed in separate pharmaceutical carriers, which are administered at the same time. Alternatively, the agents may be provided in separate dosage forms and administered sequentially.

Delivery of Agents to Hair Cells and Supporting Cells Ex Vivo

It is understood that the concepts for delivering agents of interest to hair cells and supporting cells in vivo can also apply to the delivery of the agents of interest to hair cells and supporting cells ex vivo. The hair cells and supporting cells can be harvested and cultured using techniques known and used in the art. The agents (protein expression vectors, activators and inhibitors (for example, as discussed above)) can then be contacted with the cultured hair cells or supporting cells to induce the cells to reenter the cell cycle, and proliferate. Thereafter, once the cells have proliferated, the Myc and Notch activities can be inhibited using appropriate inhibitors, for example, those discussed above. The resulting hair cells can then be maintained in culture for any number of uses, including, for example, to study the biological, biophysical, physiological and pharmacological characteristics of hair cells and/or supporting cells. Alternatively, the resulting hair cells can then be implanted in to the inner ear of a recipient using standard surgical procedures.

In certain embodiments, suitable cells can be derived from a mammal, such as a human, mouse, rat, pig, sheep, goat, or non-human primate. In certain embodiments, the cells can be harvested from the inner ear of a subject, and cells can be obtained from the cochlea organ of Corti, the modiolus (center) of the cochlea, the spiral ganglion of the cochlea, the vestibular sensory epithelia of the saccular macula, the utricular macula, or the cristae of the semicircular canals. Alternatively or in addition, methods include obtaining tissue from the inner ear of the animal, where the tissue includes at least a portion of the utricular maculae.

Tissue isolated from a subject can be suspended in a neutral buffer, such as phosphate buffered saline (PBS), and subsequently exposed to a tissue-digesting enzyme (e.g., trypsin, leupeptin, chymotrypsin, and the like) or a combination of enzymes, or a mechanical (e.g., physical) force, such as trituration, to break the tissue into smaller pieces. Alternatively, or in addition, both mechanisms of tissue disruption can be used. For example, the tissue can be incubated in about 0.05% enzyme (e.g., about 0.001%, 0.01%, 0.03%, 0.07%, or 1.0% of enzyme) for about 5, 10, 15, 20, or 30 minutes, and following incubation, the cells can be mechanically disrupted. The disrupted tissue can be passed through a device, such as a filter or bore pipette, that separates a stem cell or progenitor cell from a differentiated cell or cellular debris. The separation of the cells can include the passage of cells through a series of filters having progressively smaller pore size. For example, the filter pore size can range from about 80 µm or less, about 70 µm or less, about 60 µm or less, about 50 µm or less, about 40 µm or less, about 30 µm or less, about 35 µm or less, or about 20 µm or less.

Partially and/or fully differentiated cells, e.g., generated by the methods described above, can be maintained in culture for a variety of uses, including, for example, to study the biological, biophysical, physiological and pharmacological characteristics of hair cells and/or supporting cells. Cell cultures can be established using inner ear cells from subjects with hearing loss and/or loss in vestibular function to develop potential treatments (e.g., to screen for drugs effective in treating the hearing loss and/or loss in vestibular function). Further, the methods of the present invention can be used in combination with induced pluripotent stem (iPS) cell technology to establish cell lines (e.g., hair cell lines and/or supporting cell lines). For example, fibroblasts from a subject with hearing loss can be induced to form iPS cells using known techniques (see, for example, Oshima et al. (2010) *Cell*, 141(4):704-716).

However, because the numbers of cells generated using iPS cell technology is limited, the methods provided herein can be used in combination with iPS cell technology to produce sufficient numbers of cells to establish cell lines (e.g., hair cell lines and/or supporting cell lines).

Partially and/or fully differentiated cells, e.g., generated by the methods described above, can be transplanted or implanted, such as in the form of a cell suspension, into the ear by injection, such as into the luminae of the cochlea. Injection can be, for example, through the round window of the ear or through the bony capsule surrounding the cochlea.

The cells can be injected through the round window into the auditory nerve trunk in the internal auditory meatus or into the scala tympani. In certain embodiments, the cells described herein can be used in a cochlea implant, for example, as described in U.S. Patent Publication No. 2007/0093878.

To improve the ability of transplanted or implanted cells to engraft, cells can be modified prior to differentiation. For example, the cells can be engineered to overexpress one or more anti-apoptotic genes. The Fak tyrosine kinase or Akt genes are candidate anti-apoptotic genes that can be used for this purpose; overexpression of FAK or Akt can prevent cell death in spiral ganglion cells and encourage engraftment when transplanted into another tissue, such as an explanted organ of Corti (see, for example, Mangi et al., (2003) *Nat. Med.* 9: 1195-201). Neural progenitor cells overexpressing $\alpha_v\beta3$ integrin may have an enhanced ability to extend neurites into a tissue explant, as the integrin has been shown to mediate neurite extension from spiral ganglion neurons on laminin substrates (Aletsee et al., (2001) *Audiol. Neu. Ootol.* 6:57-65). In another example, ephrinB2 and ephrinB3 expression can be altered, such as by silencing with RNAi or overexpression with an exogenously expressed cDNA, to modify EphA4 signaling events. Spiral ganglion neurons have been shown to be guided by signals from EphA4 that are mediated by cell surface expression of ephrin-B2 and -B3 (Brors et al., (2003) *J. Comp. Neurol.* 462:90-100). Inactivation of this guidance signal may enhance the number of neurons that reach their target in an adult inner ear. Exogenous factors such as the neurotrophins BDNF and NT3, and LIF can be added to tissue transplants to enhance the extension of neurites and their growth towards a target tissue in vivo and in ex vivo tissue cultures. Neurite extension of sensory neurons can be enhanced by the addition of neurotrophins (BDNF, NT3) and LIF (Gillespie et al. (2010) *Neuro. Report* 12:275-279).

Measurement of Myc, Notch or Atoh1 Activity in Target Cells

The methods and compositions described herein can be used to induce cells, e.g., adult mammalian inner ear cells, to reenter the cell cycle and proliferate. For example, the number of hair cells can be increased about 2-, 3-, 4-, 6-, 8-, or 10-fold, or more, as compared to the number of hair cells before treatment. The hair cell can be induced to reenter the cell cycle in vivo or ex vivo. It is contemplated that using these approaches it may be possible to improve the hearing of a recipient. For example, using the methods and compositions described herein, it may be possible to improve the hearing of a recipient by at least about 5, 10, 15, 20, 40, 60, 80, or 90% relative to the hearing prior to the treatment. Tests of auditory or vestibular function also can be performed to measure hearing improvement.

Cells that have been contacted with (i) a Myc protein or Myc activator and/or (ii) a Notch protein, NICD protein or Notch activator, can be assayed for markers indicative of cell cycle reentry and proliferation. In one example, a cell can be assayed for incorporation of EdU (5-ethynyl-2'-deoxyuridine) followed sequentially by BrdU (5-bromo-2'-deoxyuridine) by using, for example, an anti-EdU antibody and an anti-BrdU antibody. Labelling by EdU and/or BrdU is indicative of cell proliferation. In addition, double labeling of EdU and BrdU can be used to demonstrate that a cell has undergone division at least two times. Alternatively or in addition, a cell can be assayed for the presence of phosphorylated histone H3 (Ph3) or aurora B, which are indicative of a cell that has reentered the cell cycle and is undergoing metaphase and cytokinesis.

Cell markers can also be used to determine whether a target cell, e.g., a hair cell or a supporting cell, has entered the cell cycle. Exemplary markers indicative of hair cells include Myo7a, Myo6, Prestin, Lhx3, Dner, espin, parvalbumin, and calretinin. Exemplary markers indicative of supporting cells include Sox2, S100a1, Proxl, Rps6, and Jag1. Double labeling of a cell cycle and/or proliferation marker and a cell-type molecule can be used to determine which cells have reentered the cell cycle and are proliferating.

In addition, neuronal markers, e.g., acetylated tubulin, neurofilament and CtBP2, can be used to detect neuronal structure, to determine whether proliferating hair cells are in contact with neurons. The presence of neuronal markers adjacent to or in contact with hair cells suggests that newly-generated hair cells have formed synapses with neurons (e.g., ganglion neurons) and that the hair cells are differentiated.

Where appropriate, following treatment, the subject, for example, a human subject, can be tested for an improvement in hearing or in other symptoms related to inner ear disorders. Methods for measuring hearing are well-known and include pure tone audiometry, air conduction, auditory brainstem response (ABR) and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlea hair cells, and electro-cochleography provides information about the functioning of the cochlea and the first part of the nerve pathway to the brain. In certain embodiments, treatment can be continued with or without modification or can be stopped.

Compositions

In some embodiments, a composition comprises a cationic lipid encapsulating one or more chimeric molecules. These chimeric molecules comprise one or more proteins or peptides fused, complexed or linked to one or more anionic molecules. The anionic molecules can vary as long as they comprise one or more anionic domains or bind to an anionic nucleic acid domain. It is preferred that the anionic molecules confer an overall net negative charge to the chimeric molecule. Without wishing to be bound by theory, it was hypothesized that proteins that are engineered to be highly negatively charged or that are naturally highly anionic may be able to take advantage of the same electrostatics-driven complexation and encapsulation used by cationic liposomal reagents for nucleic acid delivery. While few proteins natively possess the density of negative charges found in the phosphate backbone of nucleic acids, it was speculated that translational fusion to, or non-covalent complexation with, a polyanionic molecule may render the resulting protein or protein complex sufficiently anionic to be efficiently complexed by common cationic lipid reagents.

Accordingly, in some embodiments, the anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (siRNA), a micro, interfering RNA (miRNA), a small, temporal RNA (stRNA), a short, hairpin RNA (shRNA), mRNA, nucleic acid sequences comprising one or more modified nucleobases or backbones, or combinations thereof.

The one or more proteins or peptides of the chimeric or anionic molecule can possess any charge as long as the overall net charge of the chimeric molecule is anionic. Accordingly, in embodiments, the proteins or peptides are cationic, anionic or are neutrally charged. Examples of proteins or peptides of the chimeric molecule which can be complexed or linked to the polyanionic molecule or domain comprise: enzymes, hormones, chemotherapeutic agents, immunotherapeutic agents, gene editing agents, synthetic molecules or combinations thereof.

In some embodiments, the protein or peptide is a therapeutic agent for delivery to a specific target. The target can be any desired intracellular target. In some embodiments, the target is a nucleic acid sequence or gene. In embodiments where it is desired to manipulate, modulate or edit a gene, the protein or peptide is a gene or genome editing agent. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof. In some embodiments, the target is a protein or peptide. Accordingly, in some embodiments, the chimeric or anionic molecule comprises one or more gene editing agents, transcriptional modulators, translational modulators, post-translational modulators, and/or modulators that regulate protein expression, function, activity or combinations thereof.

In other embodiments, the chimeric molecule optionally comprises one or more detectable labels, anions, radiolabels, tags, targeting agents, negatively charged proteins or peptides, or combinations thereof. These molecules can be selected based on the user's desired goal, e.g. for diagnostic or research purposes, or to increase the anionic charge, targeting signals and the like. Accordingly, a liposomal formulation for complexing protein and nucleic acid (e.g. transcription factors with their target binding region as oligonucleotides) for inner ear cell types delivery in vivo, is used to treat deafness or associated disorders thereof as the chimeric molecule can be tailored for regeneration (e.g. hair cell and auditory neuron regeneration), repair (e.g. re-establishment of connections between hair cells and neurons for hearing recovery) and prevention (e.g. by protein function of isl1 that prevents hair cell death during aging and noise exposure, thus preserving hearing).

In other embodiments, a chimeric molecule comprises at least one protein or peptide fused, complexed or linked to one or more anionic molecules. Preferably, the one or more anionic molecules comprise one or more anionic domains or bind to an anionic nucleic acid domain. In embodiments, the chimeric molecule comprises an overall net negative charge. In some embodiments, the anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (siRNA), a micro, interfering RNA (miRNA), a small, temporal RNA (stRNA), a short, hairpin RNA (shRNA), mRNA, nucleic acid sequences comprising one or more modified nucleobases or backbones, or combinations thereof. The chimeric molecule also comprises one or more proteins or peptides which are cationic, anionic or are neutrally charged. Examples of proteins include without limitation: enzymes, hormones, chemotherapeutic agents, immunotherapeutic agents, genome or gene editing agents, synthetic molecules or combinations thereof. The gene or genome editing agents comprise: transcriptional activators, transcriptional repressors, recombinases, nucleases, DNA-binding proteins or nucleic acids, or combinations thereof. In other embodiments, the chimeric molecule optionally comprises one or more detectable labels, radiolabels, tags, anions, targeting agents or combinations thereof.

In other embodiments, a cationic liposome encapsulates an anionic molecule comprising a protein or peptide complexed, fused or linked to a negatively charged molecule. In some embodiments, the negatively charged molecule comprises oligonucleotides, polynucleotides, proteins, peptides, peptide nucleic acids (PNA), synthetic molecules or combinations thereof. In other embodiments, the polynucleotide or oligonucleotide is a guide RNA. In some embodiments, the protein or peptide is a negatively charged fluorescent protein. In yet other embodiments, the one or more proteins or peptides are cationic, anionic or are neutrally charged. In yet another embodiment, the negatively charged protein is fused or linked to one or more proteins or peptides. In some embodiments, the protein or peptide comprises: enzymes, hormones, chemotherapeutic agents, immunotherapeutic agents, gene editing agents, synthetic molecules or combinations thereof. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof.

In other embodiments, the liposome comprises one or more cationic lipids, modified lipids or combinations thereof.

In some embodiments, a liposome encapsulating one or more molecules embodied herein comprises a liposome, a nanoliposome, a niosome, a microsphere, a nanosphere, a nanoparticle, a micelle, or an archaeosome.

Modified Proteins or Peptides: Hybrid proteins comprising a polypeptide or fragment thereof may be linked to other types of polypeptides, for example, a negatively supercharged green fluorescent protein in addition to a reporter polypeptide, or in lieu of a reporter polypeptide. These additional polypeptides may be any amino acid sequence useful for the purification, identification, overall charge of the protein or peptide, and/or therapeutic or prophylactic application of the peptide. In addition, the additional polypeptide can be a signal peptide, or targeting peptide, etc.

In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which does not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

Modified Oligonucleotides: Examples of some oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, $CH$,—$N(CH_3)$—O—$CH_2$ [known as a methylene(methylimino) or MMI backbone], $CH_2$—O—$N(CH_3)$—$CH_2$, $CH_2$—$N(CH_3)$—N($CH_3$)—$CH_2$ and O—$N(CH_3)$—$CH_2$—$CH_2$ backbones, wherein the native phosphodiester backbone is represented as O—P—O—CH). The amide backbones disclosed by De Mesmaeker et al. Acc. Chem. Res. 1995, 28:366-374) are also embodied herein. In some embodiments, the oligonucleotides having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. Science 1991, 254, 1497). Oligonucleotides may also comprise one or more substituted sugar moieties. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA 1989, 86, 6553), cholic acid (Manoharan et al. Bioorg. Med. Chem. Let. 1994, 4, 1053), a thioether, e.g., hexyl-S-tritylthiol (Manoharan et al. Ann. N.Y. Acad. Sci. 1992, 660, 306; Manoharan et al. Bioorg. Med. Chem. Let. 1993, 3, 2765), a thiocholesterol (Oberhauser et al., Nucl. Acids Res. 1992, 20, 533), an aliphatic chain, e.g., dodecandiol or undecyl residues (Saison-Behmoaras et al. EMBO J. 1991, 10, 111; Kabanov et al. FEBS Lett. 1990, 259, 327; Svinarchuk et al. Biochimie 1993, 75, 49), a phospholipid, e.g., di-hexadecyl-rac-glycerol or triethylammonium 1,2-di-O-hexadecyl-rac-glycero-3-H-phosphonate (Manoharan et al. Tetrahedron Lett. 1995, 36, 3651; Shea et al. Nucl. Acids Res. 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

Labeled Molecules: In another preferred embodiment, the chimeric molecules can be labeled. Uses include therapeutic and imaging for diagnostic and prognostic purposes. The label may be a radioactive atom, an enzyme, or a chromophore moiety. Methods for labeling antibodies have been described, for example, by Hunter and Greenwood, *Nature*, 144:945 (1962) and by David et al. *Biochemistry* 13:1014-1021 (1974). Additional methods for labeling antibodies have been described in U.S. Pat. Nos. 3,940,475 and 3,645,090. Methods for labeling oligonucleotide probes have been described, for example, by Leary et al. *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al. *Nucl. Acids Res.* (1985) 13:2399; and Meinkoth and Wahl, *Anal. Biochem.* (1984) 138:267.

The label may be radioactive. Some examples of useful radioactive labels include $^{32}$P, $^{125}$I, $^{131}$I, and $^{3}$H. Use of radioactive labels have been described in U.K. 2,034,323, U.S. Pat. Nos. 4,358,535, and 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), β-galactosidase (fluorescein β-D-galactopyranoside), and alkaline phosphatase (5-bromo-4-chloro-3-indolyl phosphate/nitro blue tetrazolium). The use of enzymatic labels has been described in U.K. 2,019,404, EP 63,879, and by Rotman, *Proc. Natl. Acad. Sci. USA*, 47, 1981-1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the chimeric molecule by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophores may be conjugated to the antibodies or nucleotides by means of coupling agents, such as dialdehydes, carbodiimides, dimaleimides, and the like.

In another preferred embodiment, the chimeric fusion molecules of the invention can be used for imaging. In imaging uses, the complexes are labeled so that they can be detected outside the body. Typical labels are radioisotopes, usually ones with short half-lives. The usual imaging radioisotopes, such as $^{123}$I, $^{124}$I, $^{125}$I, $^{131}$I, $^{99m}$TC, $^{186}$Re, $^{188}$Re, $^{64}$Cu, $^{67}$Cu, $^{212}$Bi, $^{213}$Bi, $^{67}$Ga, $^{90}$Y, $^{111}$In, $^{18}$F, $^{3}$H, $^{14}$C, $^{35}$S or $^{32}$P can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

Reporter genes useful in the present invention include acetohydroxy acid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Kits

In yet another aspect, the invention provides kits for targeting nucleic acid sequences of cells and molecules associated with modulation of the target molecule. For example, the kits can be used to target any desired nucleic sequence and as such, have many applications.

In one embodiment, a kit comprises: (a) a cationic lipid, and a chimeric molecule or an encapsulated chimeric molecule, or a protein and a separate polyanionic molecule, or any combinations thereof, and (b) instructions to administer to cells or an individual a therapeutically effective amount of the composition. In some embodiments, the kit may comprise pharmaceutically acceptable salts or solutions for administering the composition. Optionally, the kit can further comprise instructions for suitable operational parameters in the form of a label or a separate insert. For example, the kit may have standard instructions informing a physician or laboratory technician to prepare a dose of chimeric molecule.

Optionally, the kit may further comprise a standard or control information so that a patient sample can be compared with the control information standard to determine if the test amount of chimeric molecule is a therapeutic amount consistent with for example, treating deafness in a patient.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Efficient Delivery of Proteins In Vitro and In Vivo

One of the goals is to develop a protein-based hair cell regeneration paradigm by delivering functional Myc/NICD proteins to adult guinea pig inner ear to induce supporting cell proliferation, and to transdifferentiate them to hair cells. The approach is to restore hearing in deafened guinea pig models exposed to noise and treated by ototoxic drugs. The protein based-therapy is to be applied to adult human inner ear ex vivo for induction of proliferation and hair cell regeneration.

Development of protein delivery into adult guinea pig inner ear for induction of proliferation: The guinea pig model was chosen for the study due to the fact it is non-transgenic, with an inner ear that is about ten times larger than the mouse inner ear, and with well-understood hearing and deafness characteristics. This makes it possible to develop a procedure (biological and surgical) applicable to humans. A protein-based therapy was chosen as it delivers biological molecules with specific and transient function. With this approach, the dose, duration and relative ratio of proteins to be delivered can be optimized in vitro and in vivo.

The protein-based therapy is delivered using a modified supercharged GFP protein that is linked to aurein (s-GFP-aurein or alternatively referred to, herein, as aurein-+36GFP), a peptide with antibacterial function secreted by frog. When linked with s-GFP-aurein, Cre recombinase is taken up by inner ear supporting cells in vivo after being directly injected into the inner ears of neonatal and adult mice. Cre recombinase delivered was translocated into nuclei, leading to the cleavage of the floxP sites and expression of a reporter gene tdTomato. s-GFP-aurein is fused with Myc and NICD and delivery to the supporting cells of adult guinea pig inner ears is tested.

Production of fusion proteins including s-GFP-aurein, s-GFP-aurein-NICD and s-GFP-aurein-Atoh1: The respective proteins are purified at micro molar (µm) concentrations and tested for inner ear delivery. s-GFP-aurein-Atoh1 is used for the study.

Testing of the combined Myc/NICD proteins for adult mouse inner ear delivery to induce proliferation in vivo. As adult mouse supporting cells proliferate in response to Myc/NICD activation, and take up s-GFP-aurein, the adult mouse inner ear is used for a proof-of-principle experiment testing the ability of s-GFP-aurein carrying the transcription factors Myc and NICD to induce the proliferation of supporting cells.

Test Myc/NICD protein delivery to induce proliferation in the adult guinea pig inner ear in vivo. Combinations of s-GFP-aurein-Myc/s-GFP-aurein-NICD are injected into adult guinea pig inner ears. Induction of proliferation is evaluated by doses, the ratios between the two proteins, the duration of effects and single vs. multiple injections. The conditions under which limited proliferation is induced in the inner ear sensory epithelial region that is suitable for transdifferentiation into hair cells are to be identified. Further attention will be paid to any sign of tumor formation. In the current study by continuous expression of Myc/NICD through viral infection or by induced Myc/NICD transgene expression for over 30 days, tumors were not observed. The transient nature of protein-based therapy, with an estimated protein half-life of less than 24 hours, should further dramatically reduce the risk of tumor formation. It is important to note that human inner ear is one of the organs in which no endogenous tumor has been identified, making it a better organ for renewed proliferation without associated tumorigenesis.

Optimization of route of delivery in adult guinea pig inner ear. Guinea pigs serve as an excellent model to optimize the surgical procedure for protein delivery that should be applicable to humans. The cochlea is a snail-shaped structure that senses sounds ranging from high frequency at the base to low frequency at the apex. It is critical to regenerate hair cells along the length of the cochlea so hearing can be recovered in most frequencies. Ways to reach different cochlear regions will be evaluated, including single injection of fluorophore-labeled s-GFP-aurein (which itself does not have fluorescence due to modifications to GFP) to the middle turn, multiple injections to different turns, and injections to different chambers of the cochlea (scala tympani vs. scala media). The goal is to identify a simple procedure that optimizes therapeutic effects while avoiding damage to the inner ear.

Example 2: Hair Cell Regeneration in Adult Guinea Pig In Vivo

Two approaches are used to transdifferentiate supporting cells into hair cells in the adult mouse inner ear: overexpression of Atoh1 and blockade of the Notch pathway by inhibitors.

Hair cell regeneration by Atoh1 overexpression. Delivery of s-GFP-aurein-Atoh1 into supporting cells is evaluated for hair cell induction. This is performed three to five days after Myc/NICD induced proliferation, as Myc/NICD activity is required for proliferation and their downregulation is important to Atoh1 induced hair cell transdifferentiation. Due to the relatively short half-life of the delivered proteins, downregulation of Myc/NICD is thus achieved by slightly delayed Atoh1 delivery. Following the protein-delivery of Atoh1, hair cell production at different time points is examined. The shortest period within which differentiated and functional hair cells are regenerated is to be identified. Interestingly by adenovirus-mediated delivery of Atoh1 into adult mammalian cochlea including mouse, rat and guinea pig, no convincing hair cell regeneration has been observed by various labs, which demonstrate that it is highly unlikely hair cells can be induced by Atoh1 alone in adult inner ear. However with the activation of Myc/NICD, the inventors routinely achieve hair cell regeneration by Ad-Atoh1 in adult mouse inner ear in vivo.

Hair cell regeneration by blocking Notch pathway by DAPT and LY411575. The advantage of using Notch inhibitors is that they are well characterized and there are multiple forms, some of which have been approved for clinical use, including Eli Lilly's Alzheimer drug (gamma-secretase inhibitor LY411575). Local delivery of DAPT and LY411575 is tested by placing PEG400 or gelform containing different concentrations of DAPT and LY411575 in the round window niche (just outside the membrane of the inner ear that separates middle and inner ear). Two to four weeks later, hair cell regeneration will be evaluated. The shortest period within which differentiated hair cells can be regenerated is determined.

Example 3: Hair Cell Regeneration to Restore Hearing

Hearing loss in guinea pigs can be induced by noise exposure or ototoxic drug treatment (e.g. gentamicin). The functional test following hair cell regeneration is hearing restoration. By auditory brainstem response (ABR), hearing recovery can be precisely measured.

Hearing restoration in noise-induced deaf guinea pig model: Guinea pigs are subjected to noise to create profound (complete) hearing loss across different frequencies that are associated with major hair cell loss. Supporting cell proliferation is induced by protein delivery and hair cell regeneration by Atoh1 protein and by application of Notch inhibitors in one ear; whereas the contralateral uninjected ear serves as a control. ABR is performed 1-4 months following injection, to study hearing recovery. In control ear, no ABR or significantly elevated ABR thresholds are detected at any frequencies. In the injected inner ear, ABR will ascertain hearing recovery (by dB) across different frequencies. For instance detection by ABR at 50 dB at 16 kHz is a demonstration of hearing in the middle frequency with a threshold at 50 dB (i.e. the animal can hear the sound at 50 dB or above at this frequency). This study will demonstrate precisely how much hearing has recovered and at what frequencies.

ABR identifies whether or not regenerated hair cells are functional and the effect on hearing recovery. It will provide information regarding the procedure that produces the best outcome. For instance by correlating the surgical and delivery procedure with ABR, it can be determined how effective the approach is on hearing restoration at different frequencies, which has a direct relevance in human study.

Hearing restoration in deaf guinea pig treated with ototoxic drugs: Ototoxic drugs (aminoglycoside antibiotics neomycin and gentamicin, and anti-cancer drug Cisplatin) preferentially kill hair cells to cause hearing loss. Guinea pigs will be treated with gentamicin to create permanent deafness. Protein delivery of Myc/NICD followed by Atoh1 and Notch inhibitors will be similarly studied. ABR will be performed to analyze hearing recovery in the injected inner ears vs. uninjected control inner ears. Detection of ABR will be a demonstration of hearing recovery following delivery of key molecules.

Hearing recovery between the above two models is compared to determine which recovery is more prominent. This information would be useful in determining the type of patients to enroll in clinical study.

Example 4: Induction of Proliferation and Hair Cell Regeneration in Adult Human Cochlea Ex Vivo Protein delivery of Myc/NICD is performed for proliferation and Atoh1 and Notch inhibitor for hair cell regeneration using cultured human inner ear. This study will evaluate the similarity and difference in protein-based therapy in guinea pig and human inner ears, providing important information that is relevant to clinical study. Due to extreme conservation between mammalian inner ear, it is expected to see a highly similar outcome in human inner ear explant study as in the guinea pig.

Example 5: Protein Delivery into the Inner Ear

The goal of this study was to use protein-mediated delivery system to deliver the biological proteins directly inner ear cell types with functional consequences. With this method, the proteins delivered have specific functions, and the effect is transient. Further, delivery of native protein lessens any potential immune response.

As cell surface is cationic (positively charged), it has been demonstrated that, by changing amino acids, GFP (green fluorescent protein) can be modified to be highly charged (both positively and negatively, named supercharged protein), which enables the supercharged GFP to enter cells. As a result, the super-charged GFP (s-GFP) can be used as vehicle to link and deliver other proteins into cells with biological effect in vitro and in vivo. This was demonstrated in mouse retina in which s-GFP carrying Cre recombinase (s-GFP-Cre) was delivered that resulted in expression of reporter gene in retinal cells. The s-GFP used as (−30)-GFP, a negatively charged GFP protein.

Figure 1B:
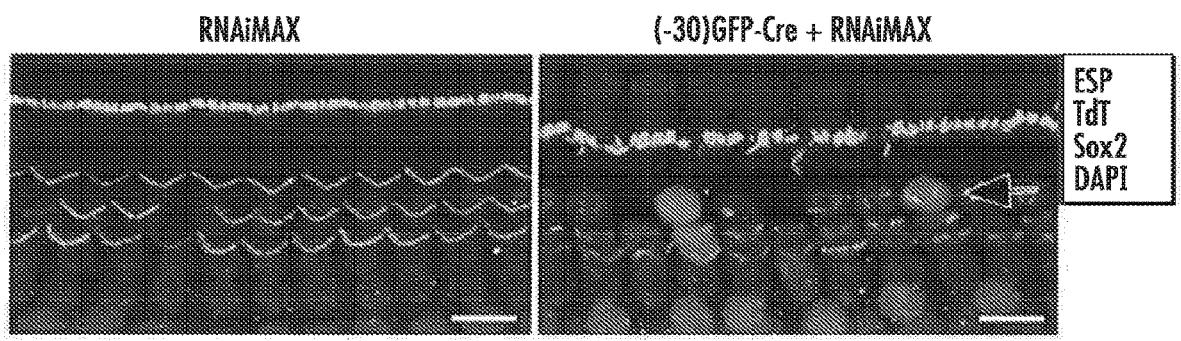
Figures 2A, 2B, 2C:
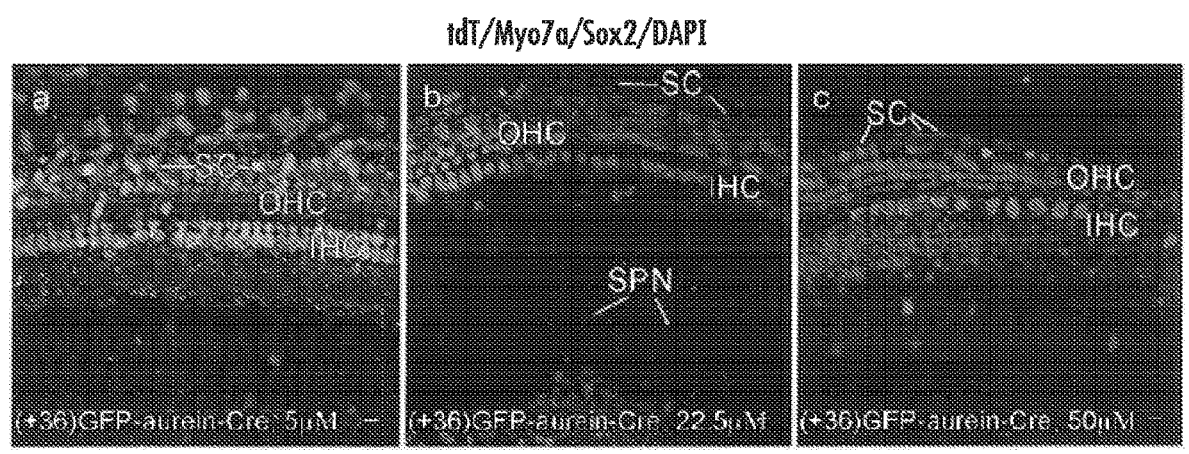
FIGS. 2A-2E show the high efficiency of protein delivery mediated by aurein in the inner ear in vivo. Injection of (+36)GFP-aurein-Cre with different concentrations to Rosa-tdT$^{f/f}$ mouse cochlea resulted in tdT labeling in cochlear cell types with different efficiencies.
Figures 2D, 2E:
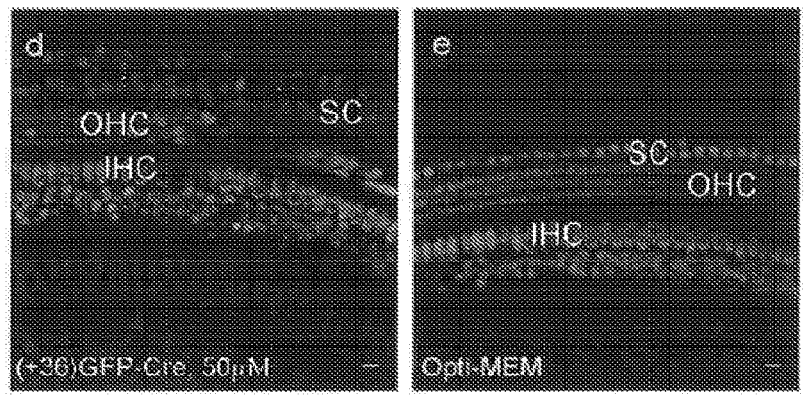
Figure 3:
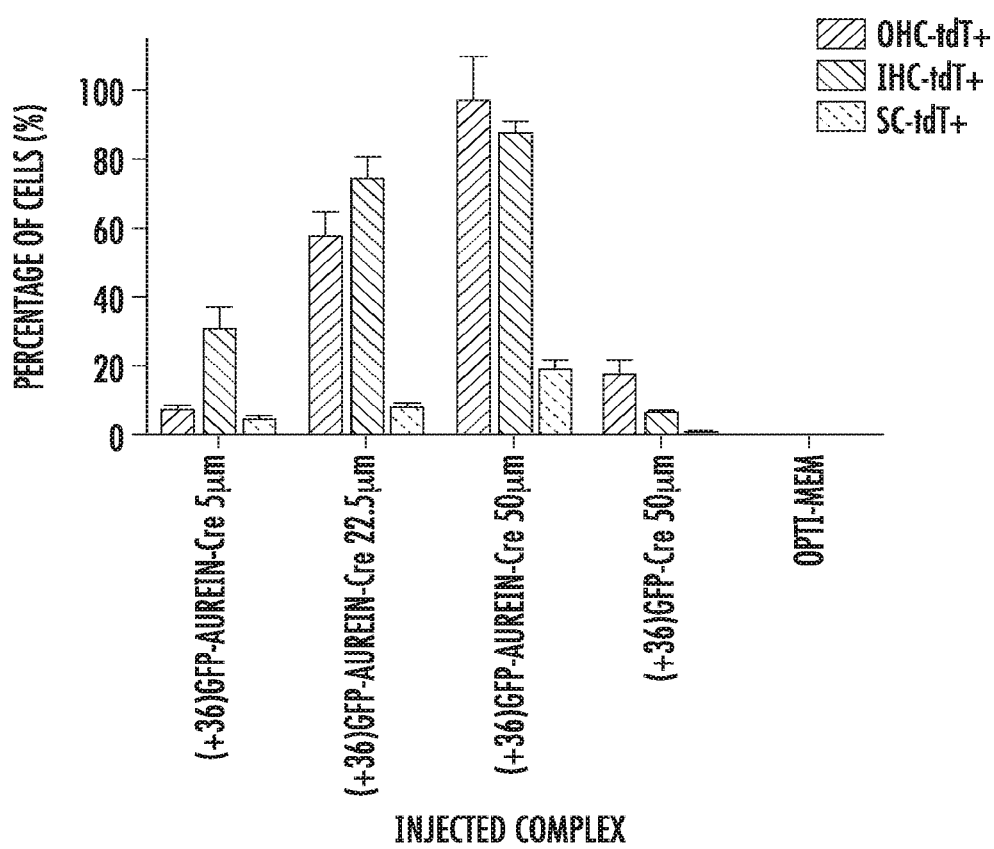
FIG. 3 shows the high efficiency of aurein mediated protein delivery in the mammalian inner ear. Comparison between different concentrations of (+36)GFP-aurein-Cre and control reveled that extremely high-efficient delivery of functional protein (Cre) with the aurein at 22.5 and 50 µM, respectively.
Figure 4:
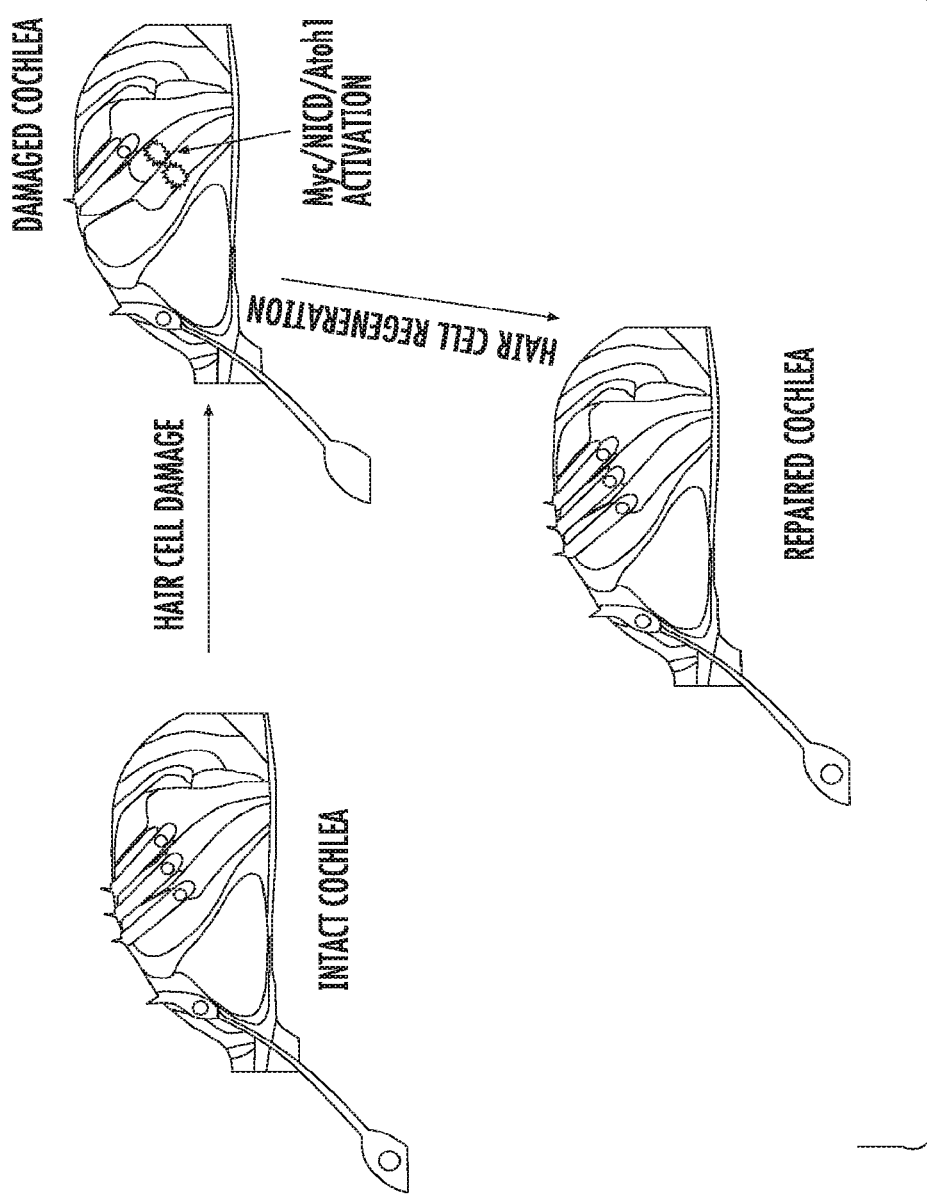
FIG. 4 is a schematic diagram depicting hair cell regeneration. After inner ear damage that leads to hair cell loss, Myc/NICD are transiently activated in the supporting cells to induce proliferation, followed by transient Atoh1 activation that results in transdifferentiation from supporting cells to hair cells. Arrows point to two supporting cells that divide and give rise to new hair cells. In the repaired cochlea, the number of hair cells and supporting cells are restored.
Figure 5:
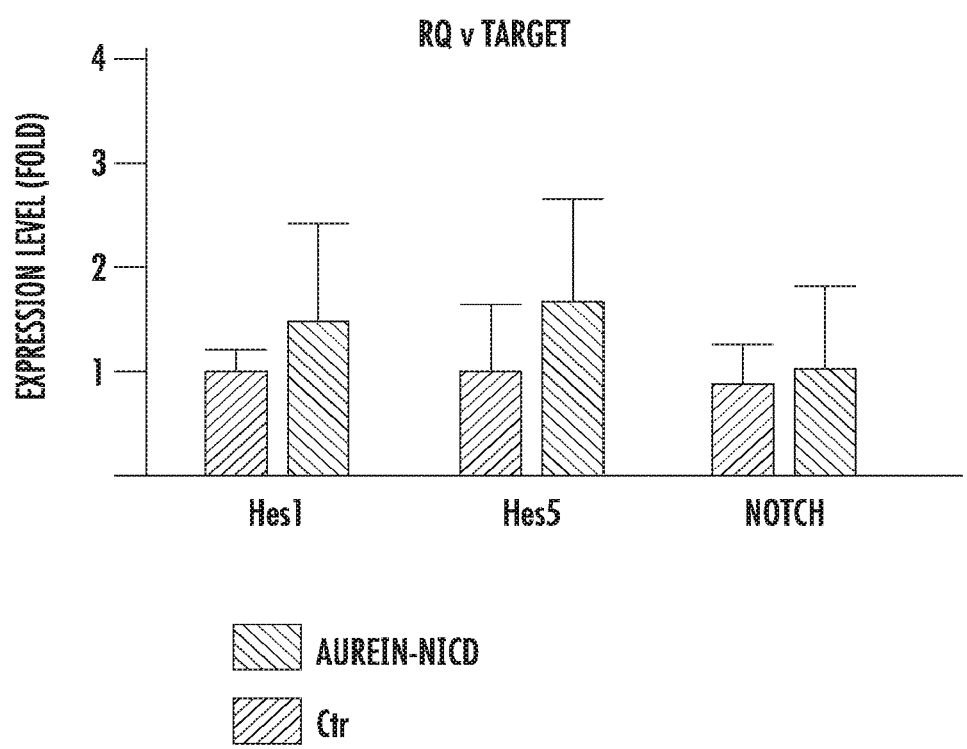
FIG. 5 is a graph showing that after aurein-NICD infection in cultured neonatal mouse cochlea, qRT-PCR showed a general increase in expression for all Notch pathways genes including Hes1, Hes5 and Notch.
Figures 6A, 6B, 6C:
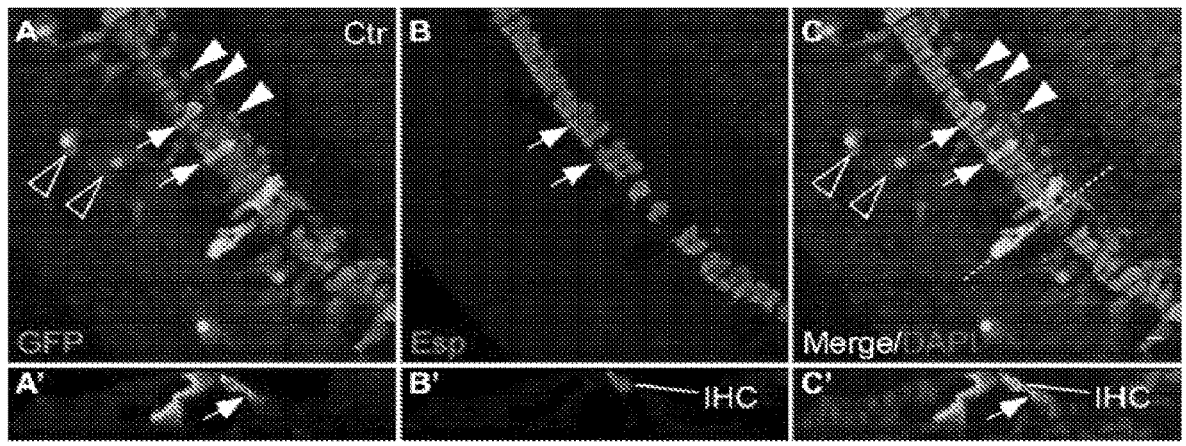
FIGS. 6A-6H show HC regeneration in vivo.
Figures 6D, 6E, 6F:
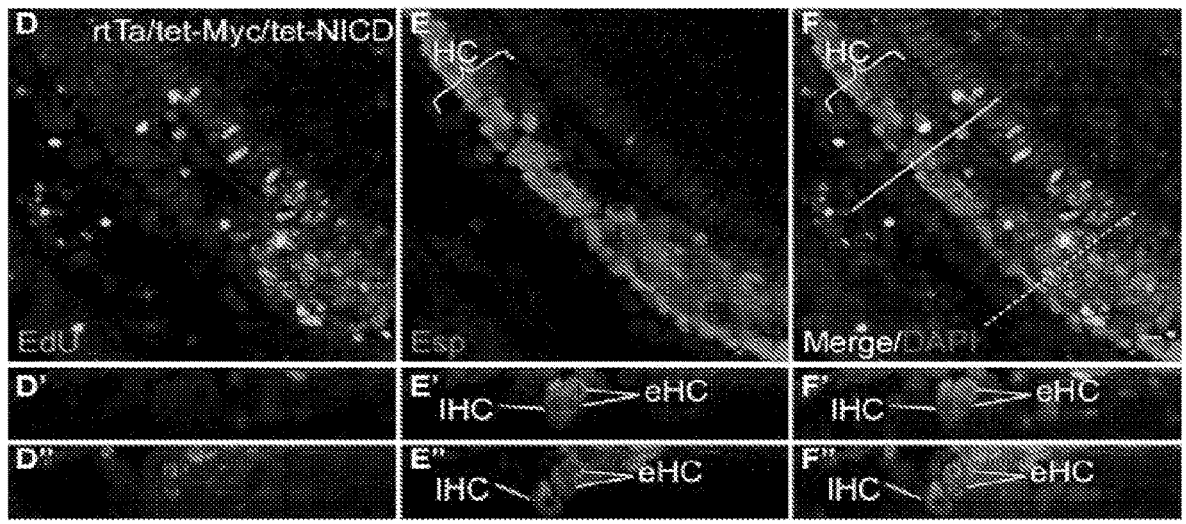
Figure 6G:
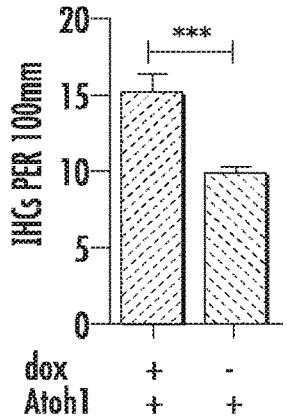
Figure 6H:
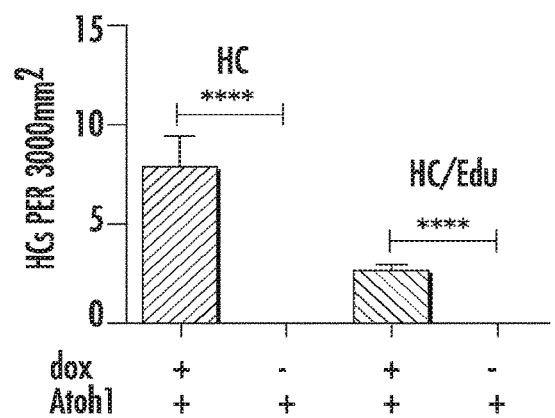
Figure 7A:
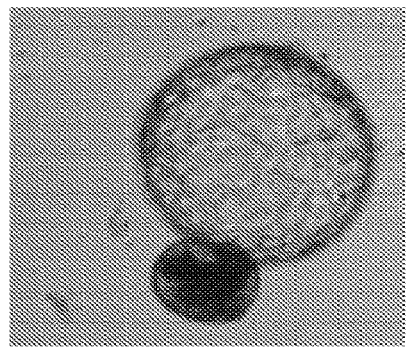
FIGS. 7A-7I show that sphere formation from adult rtTa/tet-Myc/tet-NICD cochlea treated with Dox for 7 days.
Figure 7B:
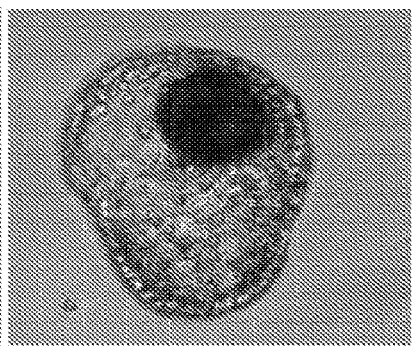
Figure 7C:
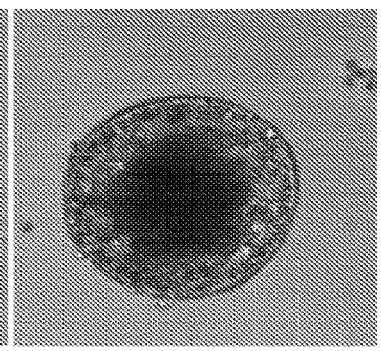
Figure 7D:
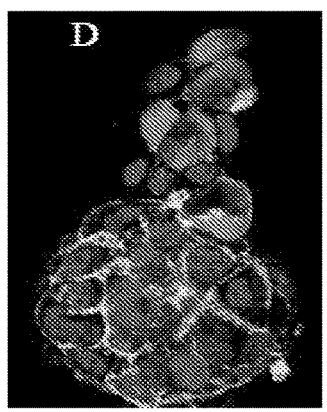
Figure 7E:
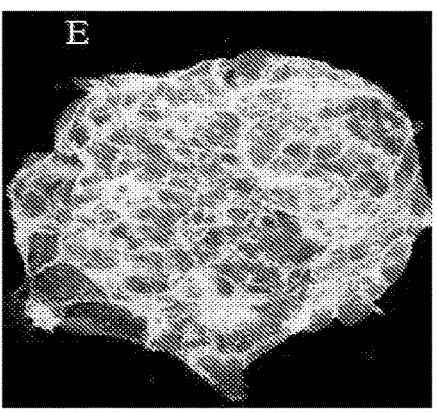
Figure 7F:
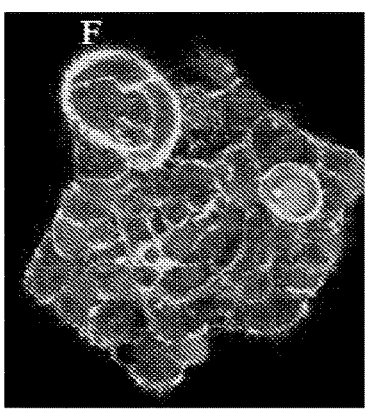
Figure 7G:
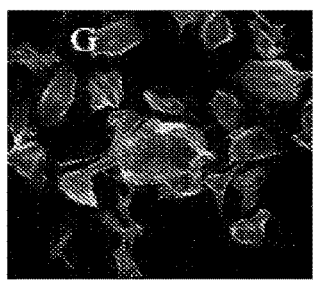
Figure 7H:
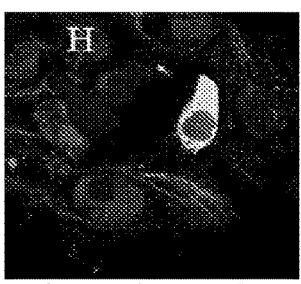
Figure 7I:

The use of (−30)-GFP protein and a new positively charged (+36)-GFP protein to carry Cre, (−30)-GFP-Cre and (+36)-GFP-Cre, was tested for injection into mouse cochlea in vivo. The mouse used was Rosa-tdTomato$^{f/f}$ in which functional Cre activity in the nuclei results in cells being labeled with tdT (red). It was shown that both (−30)-GFP-Cre and (+36)-GFP-Cre injections led to tdT expression in the cochlear hair cells. Near the injection site (base turn of cochlea), ~30% of hair cells became tdT-labeled (FIGS. 1A, 1B), The study demonstrated that supercharged GFP proteins can be used to delivery protein directly into inner ear hair cells with biological effect in nuclei.

It was next tested whether aurein, an antimicrobial peptide, in combination with s-GFP, can serve as an effective carrier to deliver functional proteins into mouse inner ear cell types with high efficiency. (+36)-GFP-aurein-Cre was injected with different concentrations into P3 Rosa-tdT mouse inner ear by cochleostomy in vivo. The tissues were harvested 5 days later for immunolabeling to identify tdT inner ear cell types. Overall it was found that cochlear hair cells were primarily labeled with tdT, with additional tdT labeling in supporting cells. At low concentrations of 5 µM, few IHC and some supporting cells (SC) were tdT$^+$. At 22.5 µM, 58% of OHC and 75% of IHC, as well as 8% of SC were tdT$^+$. At the highest 50 µM, 96% of OHC, 88% of IHC and 19% of SC were tdT$^+$. There was slight cell toxicity associated with the highest concentration of 50 µM. It was found that 20% of IHC loss 8% of OHC in the injected animals, whereas at lower concentrations of 5 and 22.5 µM no cell loss was detected.

The study demonstrated that functional proteins including nuclear proteins can be conjugated with supercharged protein (+36)GFP fused with aurein. The protein complex can be directly injected into mammalian inner ear that leads to uptake by a wide range of inner ear cell types. The protein delivered was properly localized in the nuclei and had the specific biological function in cleaving floxP sites on the DNA sequence, to activate tdTomato in the inner ear cells with high efficiency.

The delivery system can be used to study protein functions, inner ear regeneration for hearing recovery, hearing protection, etc.

Example 6: Delivery of Functional NICD by Aurein in the Inner Ear

In addition to the in vivo delivery of Cre recombinase by aurein that leads to reporter (tdTomato) expression, aurein linked with NICD was prepared for inner ear delivery in vitro. Cultured mouse cochlea were treated with aurein-NICD without lipofectamine2000. Five days after the treatment, tissues were harvested for qRT-PCR, to determine the level Notch and its two downstream targets Hes1 and Hes5. qRT-PCR showed overall that there was an increase in the level for all three genes, judging by qRT-PCR. 40%, 70% and 15% of upregulation were observed for Hes1, hes5 and Notch respectively. The level increase in Notch is smaller, which may be a reflection of degradation of Notch.

Example 7: Supporting Cells Reprogrammed by Myc/NICD Combination can Transdifferentiate to Hair Cells without Going Through Proliferation Myc/NICD co-activation leads to renewed proliferation of many cell types including supporting cells, hair cells, stria vascularis and fibrocytes. Proliferating supporting cells react to Atoh1 over expression robustly and transdifferentiate to hair cells. Further upon Myc/NICD c-activation, even without cell cycle re-entry, the supporting cells can still be reprogrammed by Myc/NICD and transdifferentiate to hair cells by Atoh1 over expression (FIGS. 6A-6H). Thus the Myc and NICD dosage is likely to play an important role, in which high activity induces proliferation and subsequent transdifferentiation, and low activity induces transdifferentiation.

Rejuvenation of adult inner ear stem cells: Inner ear stem cells have been isolated only from neonatal and early postnatal mouse (Oshima, K. et al. Differential distribution of stem cells in the auditory and vestibular organs of the inner ear. *J. Assoc. Res. Otolaryngol.* 8, 18-31 (2007)). In adult no inner ear stem cells have been isolated, an indication that the stem cells lose their potential to proliferate and regenerate. It was shown by using rtTa/tet-Myc/tet-NICD mice, in which Myc/NICD is induced by doxycycline, adult inner ear stem cells can be isolated as spheres. Further the spheres can differentiate to inner ear neurons, supporting cells and hair cells as neonatal mice (FIGS. 7A-7I). Thus Myc/NICD activation can be used to re-activate dormant adult inner ear stem cells, for regeneration of inner ear cell types for hearing recovery.

What is claimed is:

1. A chimeric molecule comprising (a) a supercharged protein, (b) an aurein peptide, and (c) a domain comprising a Myc protein, a Notch protein, a Notch Intracellular Domain (NICD) protein, Atonal Homolog 1 (Atoh1), or an Atoh1 activator.

2. The chimeric molecule of claim 1, wherein the supercharged protein is supercharged GFP (sGFP).

3. The chimeric molecule of claim 1, wherein the domain (c) is an Atoh1 activator.

4. The chimeric molecule of claim 1, wherein the aurein peptide is an aurein 1.2 peptide.

5. The chimeric molecule of claim 1, wherein the aurein peptide comprises an amino acid sequence having the sequence set forth in any one of SEQ ID NOs: 2-21.

6. The chimeric molecule of claim 1, wherein the domain (c) comprises an amino acid sequence having at least 80% identity to any one of the sequences set forth as NCBI Database Nos. NP_002458.2 (Myc), NP_060087.3 (human Notch 1), NP_077719.2 (Notch2), NP_000426.2 (Notch3), NP_004548.3 (Notch4), NP_005163.1 (Atoh1), and NP_660161.1 (Atoh7).

7. The chimeric molecule of claim 1, wherein the domain (c) comprises an amino acid sequence comprising the sequence set forth as NCBI Database Nos. NP_002458.2 (Myc), NP_005369.2 (N-myc), NP_060087.3 (human Notch 1), NP_077719.2 (Notch2), NP_000426.2 (Notch3), NP_004548.3 (Notch4), NP_005163.1 (Atoh1), and NP_660161.1 (Atoh7).

8. The chimeric molecule of claim 1, wherein the chimeric molecule is a fusion protein comprising $NH_2$-sGFP-aurein-Myc-COOH or $NH_2$-sGFP-aurein-NICD-COOH.

9. A composition comprising an effective amount of the chimeric molecule of claim 1.

10. A composition comprising an effective amount of (i) a chimeric molecule comprising supercharged GFP (sGFP) and aurein, and (ii) an Atoh1 activator.

11. The composition of claim 10, wherein the Atoh1 activator is an anti-sense oligonucleotide against hairy and Enhancer-of-split homologue 1 (Hes1) or 5 (Hes5).

12. The composition of claim 10, wherein the Atoh1 activator is a protein inhibitor of Hes1 or Hes5.

13. The composition of claim 10, wherein the Atoh1 activator is selected from β-catenin agonists; catenin pathway agonists; gamma secretase inhibitors (GSIs); gentamycin; transcription factors Eya1, Six1, and Sox2; and compounds of Formula (I):

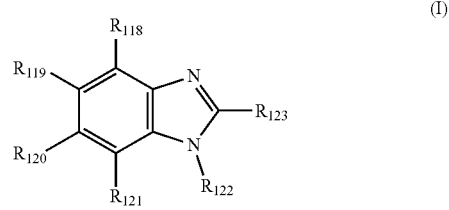

wherein:
each of $R_{118}$, $R_{119}$, $R_{120}$, and $R_{121}$ is, independently selected from H, halo, OH, CN, $NO_2$, $C_1$-$C_3$ alkyl, $C_1$-$C_3$ haloalkyl, alkoxy, and $C_1$-$C_8$ haloalkoxy;
$R_{122}$ is hydrogen or —Z—$R^a$; wherein:
Z is O or a bond; and IV is:
  (i) $C_1$-$C_6$ alkyl or $C_1$-$C_6$ haloalkyl, each of which is optionally substituted with from 1-3 $R^b$;
  (ii) $C_3$-$C_{10}$ cycloalkyl, $C_3$-$C_{10}$ cycloalkenyl, each of which is optionally substituted with from 1-5 $R^c$;
  (iii) $C_7$-$C_{11}$ aralkyl, or heteroaralkyl including 6-11 atoms, each of which is optionally substituted with from 1-5 $R^c$; or
  (iv) $C_6$-$C_{10}$ aryl or heteroaryl including 5-10 atoms, each of which is optionally substituted with from 1-5 $R^d$;
$R_{123}$ is:
  (i) hydrogen;
  (ii) $C_1$-$C_6$ alkyl or $C_1$-$C_6$ haloalkyl, each of which is optionally substituted with from 1-3 $R^b$;
  (iii) $C_6$-$C_{10}$ aryl or heteroaryl including 5-10 atoms, each of which is optionally substituted with from 1-5 $R^d$;
  (iv) $C_7$-$C_{11}$ aralkyl, or heteroaralkyl including 6-11 atoms, each of which is optionally substituted with from 1-5 $R^c$;
  (v) —($C_1$-$C_6$ alkyl)-$Z^1$—($C_6$-$C_{10}$ aryl), wherein $Z^1$ is O, S, NH, or $N(CH_3)$; the alkyl portion is optionally substituted with from 1-3 $R^b$; and the aryl portion is optionally substituted with from 1-5 $R^d$;
  (vi) —($C_1$-$C_6$ alkyl)-$Z^2$-(heteroaryl including 5-10 atoms), wherein $Z^2$ is O, S, NH, or $N(CH_3)$; the alkyl portion is optionally substituted with from 1-3 $R^b$; and the heteroaryl portion is optionally substituted with from 1-5 $R^d$; or
  (vii) —($C_1$-$C_6$ alkyl)-$Z^3$—($C_3$-$C_{10}$ cycloalkyl), wherein $Z^3$ is O, S, NH, or $N(CH_3)$; the alkyl portion is optionally substituted with from 1-3 $R^b$; and the cycloalkyl portion is optionally substituted with from 1-5 $R^c$;

$R^b$ at each occurrence is, independently:
  (i) $NH_2$; $NH(C_1$-$C_3$ alkyl); $N(C_1$-$C_3$ alkyl)$_2$; hydroxy; $C_1$-$C_6$ alkoxy; or $C_1$-$C_6$ haloalkoxy; or
  (ii) $C_3$-$C_7$ cycloalkyl, optionally substituted with from 1-3 substituents independently selected from $C_1$-$C_6$ alkyl, $NH_2$; $NH(C_1$-$C_3$ alkyl); $N(C_1$-$C_3$ alkyl)$_2$; hydroxy; $C_1$-$C_6$ alkoxy; or $C_1$-$C_6$ haloalkoxy;
$R^c$ at each occurrence is, independently:
  (i) halo; $NH_2$; $NH(C_1$-$C_3$ alkyl); $N(C_1$-$C_3$ alkyl)$_2$; hydroxy; $C_1$-$C_6$ alkoxy; $C_1$-$C_6$ haloalkoxy; or oxo; or
  (ii) $C_1$-$C_6$ alkyl or $C_1$-$C_6$ haloalkyl; and
$R^d$ at each occurrence is, independently:
  (i) halo; $NH_2$; $NH(C_1$-$C_3$ alkyl); $N(C_1$-$C_3$ alkyl)$_2$; hydroxy; $C_1$-$C_6$ alkoxy or $C_1$-$C_6$ haloalkoxy; nitro; —NHC(O)($C_1$-$C_3$ alkyl); or cyano; or
  (ii) $C_1$-$C_6$ alkyl or $C_1$-$C_6$ haloalkyl; or a pharmaceutically acceptable salt thereof.

14. The composition of claim 13, wherein the wherein the Atoh1 activator is LY411575.

15. The composition of claim 10, wherein the Atoh1 activator is selected from DSH/DVL1, DSH/DVL2, DSH/DVL3, WNT3A, WNT5A, WNT3A, and WNT35A.

16. The composition of claim 10, wherein the Atoh1 activator is selected from casein kinase 1 (CK1) inhibitors and glycogen synthase kinase 3-β (GSK3β) inhibitors.

17. The composition of claim 10 further comprising a cationic lipid.

18. A composition comprising an effective amount of a chimeric molecule comprising (a) supercharged GFP (sGFP), (b) aurein, and (c) a domain comprising Atoh1 or an Atoh1 activator.

19. The composition of claim 18, wherein the domain (c) is Atoh1.

20. The composition of claim 18, wherein the chimeric molecule is a fusion protein comprising $NH_2$-sGFP-aurein-Atoh1-COOH.

21. The composition of claim 18, wherein the aurein is an aurein 1.2 peptide.

22. A method comprising administering to the inner ear of a subject the composition of claim 9.

23. A method comprising administering to the inner ear of a subject the composition of claim 10.

* * * * *